United States Patent
Hata et al.

(10) Patent No.: US 8,383,395 B2
(45) Date of Patent: Feb. 26, 2013

(54) CELL CULTURE APPARATUS, CELL CULTURE METHOD, CELL CULTURE PROGRAM AND CELL CULTURE SYSTEM

(75) Inventors: Norihiko Hata, Yokohama (JP); Hidemasa Jinguji, Yokohama (JP); Atsutaka Noguchi, Yokohama (JP); Shiho Sato, Yokohama (JP); Kazutoshi Sato, Yokohama (JP); Naoko Ariyoshi, Yokohama (JP); Akihiro Hosoi, Yokohama (JP)

(73) Assignee: Medinet Co., Ltd., Yokohama-shi (JP)

( * ) Notice: Subject to any disclaimer, the term of this patent is extended or adjusted under 35 U.S.C. 154(b) by 1187 days.

(21) Appl. No.: 12/084,363

(22) PCT Filed: Nov. 1, 2006

(86) PCT No.: PCT/JP2006/321901
§ 371 (c)(1),
(2), (4) Date: Jul. 2, 2008

(87) PCT Pub. No.: WO2007/052716
PCT Pub. Date: May 10, 2007

(65) Prior Publication Data
US 2009/0042293 A1    Feb. 12, 2009

(30) Foreign Application Priority Data

Nov. 1, 2005   (JP) ................. 2005-318914
Nov. 1, 2005   (JP) ................. 2005-318915
Nov. 15, 2005  (JP) ................. 2005-330826
Sep. 5, 2006   (JP) ................. 2006-240729

(51) Int. Cl.
*C12M 3/00*    (2006.01)
*G06K 9/00*    (2006.01)

(52) U.S. Cl. .............. 435/286.1; 435/383; 435/289.1; 435/288.7; 382/133

(58) Field of Classification Search ............. 435/286.1, 435/289.1, 383, 288.7; 382/133
See application file for complete search history.

(56) References Cited

U.S. PATENT DOCUMENTS 5,726,009 A * 3/1998 Connors et al. ............ 435/4
6,008,010 A   12/1999 Greenberger et al.
(Continued)

FOREIGN PATENT DOCUMENTS

JP   62-113698 U   7/1987
JP   04-326993 A   11/1992
(Continued)

OTHER PUBLICATIONS

Extended European Search Report (EESR) dated May 21, 2012 (in English) in counterpart European Application No. 06822821.2.

(Continued)

*Primary Examiner* — William H Beisner
*Assistant Examiner* — Danielle Henkel
(74) *Attorney, Agent, or Firm* — Holtz, Holtz, Goodman & Chick, PC

(57) ABSTRACT

The invention intends to provide a cell culture apparatus which is able to realize an adequate culture according to the culture state of cells while alleviating the labor of an operator. The cell culture apparatus includes a culture bag for causing the cells to proliferate, a cell inoculation cassette (or culture bag as an antibody stimulating and proliferation culture vessel) for stimulating the cells by an inducer for the proliferation, a culture medium cassette for storing a culture medium supplied to the culture bag and the cell inoculation cassette, a CCD camera 88 for acquiring images of the cells in the cell inoculation cassette, and an image processing computer and an operation control computer for determining the culture state (proliferation capability and proliferation ability of the cells) of the cells from the images of the cells acquired by the CCD camera, and causing a culture operation to be carried out on the basis of the determination.

11 Claims, 41 Drawing Sheets

U.S. PATENT DOCUMENTS

| | | | |
|---|---|---|---|
| 6,855,542 B2 * | 2/2005 | DiMilla et al. | 435/289.1 |
| 7,491,526 B2 * | 2/2009 | Yanai et al. | 435/289.1 |
| 7,867,752 B1 | 1/2011 | Greenberger et al. | |
| 2003/0054335 A1 | 3/2003 | Taya et al. | |
| 2004/0241832 A1 * | 12/2004 | Muraki et al. | 435/287.1 |
| 2005/0170491 A1 | 8/2005 | Takagi et al. | |
| 2011/0195055 A1 | 8/2011 | Greenberger et al. | |

FOREIGN PATENT DOCUMENTS

| | | |
|---|---|---|
| JP | 2001-275659 A | 10/2001 |
| JP | 2002-218995 A | 8/2002 |
| JP | 2004-016194 A | 1/2004 |
| JP | 2004-208663 A | 7/2004 |
| JP | 2004-357523 A | 12/2004 |
| JP | 2005-073566 A | 3/2005 |
| WO | WO 98/20108 A1 | 5/1998 |
| WO | WO 02/42411 A1 | 5/2002 |
| WO | 2004/011593 A | 2/2004 |
| WO | WO 2004/011593 A | 2/2004 |

OTHER PUBLICATIONS

Japanese Office Action dated Jan. 27, 2012 (and English translation thereof) in counterpart Japanese Application No. 2007-542788.

Japanese Office Action dated Aug. 31, 2012 (and English translation thereof) in counterpart Japanese Application No. 2007-542788.

* cited by examiner

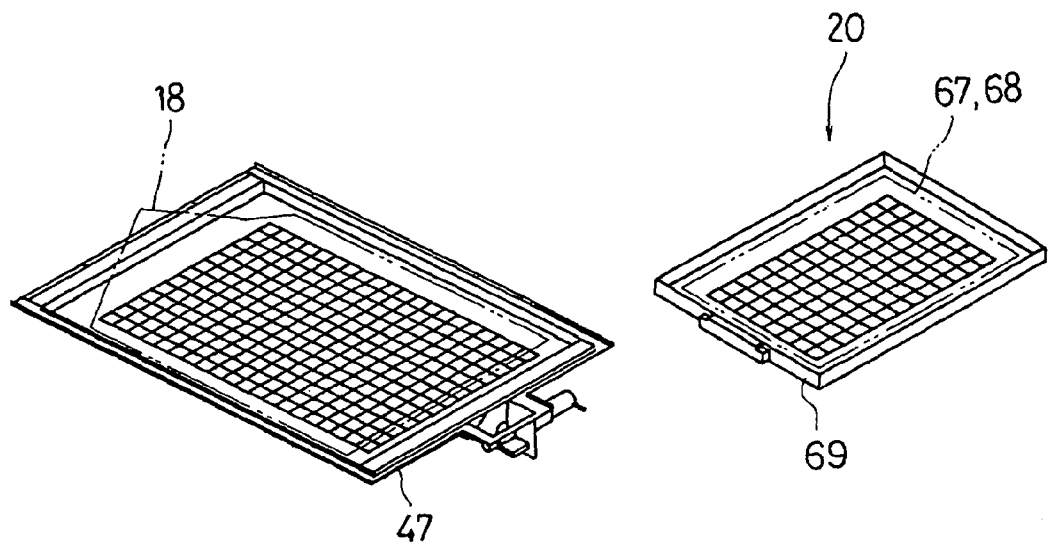
FIG.4A  FIG.4B
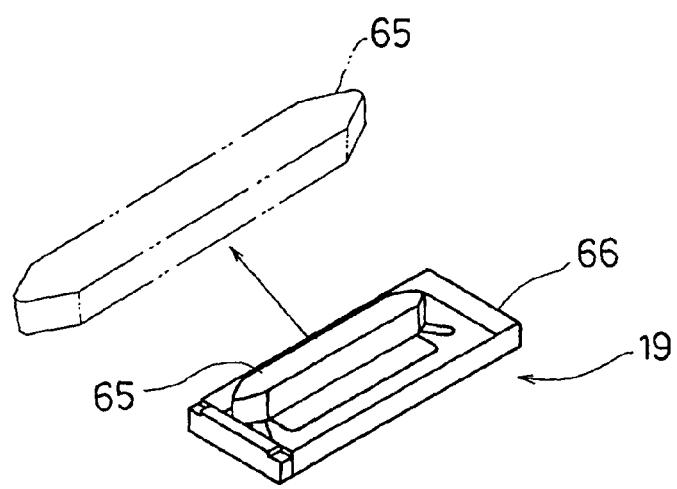
FIG.4C

CELL CULTURE APPARATUS, CELL CULTURE METHOD, CELL CULTURE PROGRAM AND CELL CULTURE SYSTEM

This application is a U.S. National Phase Application under 35 USC 371 of International Application PCT/JP2006/321901 filed Nov. 1, 2006.

BACKGROUND OF THE INVENTION

1. Field of the Invention

The present invention relates to a cell culture apparatus, a cell culture method, a cell culture program and a cell culture system for evaluating the culture state of a cell and culturing the cell.

2. Description of the Related Art

In the related art, cell culture, in particular, suspension cell culture used for an immune cell therapy is executed by human operation in most cases. For example, cells sampled from a patient are inoculated to a flask having an antibody (inducer) attached thereto together with a culture medium, and stored in an incubator. Then, the flask is taken out from the incubator every day to observe the culture state (for example, the state of proliferation) using a microscope or the like. When the proliferation is found, or when a predetermined time period has elapsed from the cell inoculation, the culture medium is added to the flask to culture the cell (for example, proliferation).

In the manual cell culture as described above, the daily operation is executed on the basis of a culture evaluation depending on the experience of a culture engineer, or the culture operation is executed homogenously for all the cells on the basis of a predetermined manual. Therefore, the culture (for example, proliferation) might not be sufficient depending on the sampled cells. In order to induce the proliferation ability of the cell which is different from patient to patient, to a maximum extent, an objective culture evaluation and the culture operation by the hour on the basis of this evaluation are necessary.

Part of such problem is solved in the culture of adherent cells as described in JP-A-2002-218995. In other words, in JP-A-2002-218995, the proliferation ability of the entire cell population is understood by observing the form of the individual adherent cells in a non-invasive and non-destructive manner through the images.

As an example which is used for the manual cell culture as described above, JP-A-2005-73566 discloses a cell culture system in which a plurality of canisters (storing units) are arranged in a single incubator (culture chamber) and culture vessels are stored in the canisters one by one for culturing cells. In this culture system, the culture environment is adapted to be the same for all the canisters in the single incubator.

However, in the case of the culture of suspension cells used for the immune cell therapy, devices for evaluating the culture state of the cells objectively or for culturing the cells on the basis of the evaluation do not exist.

In the manual cell culture including the cell culture system disclosed in JP-2005-73566, an operator who is engaged in the culture, is required to collect culture environment data in the incubator or the canisters and record the log of the culture operation such as change of the culture medium, which is a very complicated work. There is a probability that trouble in the cell culture cannot be known adequately.

SUMMARY OF THE INVENTION

In view of such circumstances as described above, it is an object of the invention to provide a cell culture apparatus, a cell culture method and a cell culture program which realize an adequate culture according to the state of the cell culture with an alleviated labor for an operator.

It is another object of the invention to provide a cell culture system, a cell culture method and a cell culture program which are able to collect and accumulate cell culture-related data which relates to the cell culture automatically, and are able to monitor and control the cell culture on the basis of the cell culture-related data.

A cell culture apparatus according to a first aspect of the invention includes a culture vessel for culturing cells; a culture medium storage unit for storing a culture medium supplied to the culture vessel; an image acquiring unit for acquiring images of the cells in the culture vessel; and a control unit for determining the culture state of the cells from the images of the cells acquired by the image acquiring unit and causing a culture operation to be carried out on the basis of the determination.

Preferably, the culture vessel includes a proliferation culture vessel for causing the cells to proliferate and a function expressing culture vessel for causing the cells to express the functions, and the image acquiring unit acquires the images of the cells in the function expressing culture vessel.

Preferably, the function expressing culture vessel is an inducer stimulating culture vessel for stimulating cells by an inducer for the proliferation, and the control unit determines the proliferation capability of the cells and the proliferation ability of the cells on the basis of the images of the cells in the inducer stimulating culture vessel and controls timing of transferring the cells from the inducer stimulating culture vessel to the proliferation culture vessel and the culture operations such as supply of the culture medium from the culture medium storage unit to the proliferation culture vessel.

Preferably, the function expressing culture vessel is a differentiation-inducing culture vessel for causing the cells to differentiate, and the control unit controls a differentiation-inducing operation on the basis of the images of the cells in the differentiation-inducing culture vessel.

Preferably, the culture medium storage unit has a cassette structure and is connected to the culture vessel.

Preferably, the function expressing culture vessel has a cassette structure, and is connected to the proliferation culture vessel and the culture medium storage unit.

Preferably, the culture medium storage unit, the function expressing culture vessel and the proliferation culture vessel make up a closed system.

Preferably, a liquid reservoir is selectively formed in the proliferation culture vessel, and the cell and the culture medium are stored in the liquid reservoir in an initial stage of culture in the proliferation culture vessel.

Preferably, the cells proliferated in the proliferation culture vessel are introduced into the function expressing culture vessel and the image acquiring unit acquires images of the introduced cells.

Preferably, the culture medium storage unit includes a used culture medium storage vessel which is able to store a used culture medium installed therein together with a culture medium storage vessel which is able to store a culture medium to be supplied to the culture vessel, and the used culture medium in the proliferation culture vessel is discharged to the used culture medium storage vessel and is stored therein.

Preferably, the culture medium storage unit is able to mount a cell collecting vessel for collecting the cells mounted thereto, and the cells condensed in the proliferation culture vessel are collected in the cell collecting vessel.

Preferably, the cells are suspension cells.

Preferably, the cells are used in an immune cell therapy.

A cell culture method according to a second aspect of the invention includes: acquiring images of cells in a culture vessel for culturing cells by an image acquiring unit; determining the culture state of the cells from the images of the cells acquired by the image acquiring unit; and carrying out a culture operation in the culture vessel on the basis of the determination.

Preferably, the culture vessel includes a proliferation culture vessel for causing the cells to proliferate and a function expressing culture vessel for causing the cells to express the functions, and the image acquiring unit acquires the images of the cells in the function expressing culture vessel.

Preferably, the function expressing culture vessel is an inducer stimulating culture vessel for stimulating cells by an inducer for the proliferation, and the proliferation capability of the cells and the proliferation ability of the cells are determined on the basis of the images of the cells in the inducer stimulating culture vessel, the timing of transferring the cells from the inducer stimulating culture vessel to the proliferation culture vessel is controlled and culture operations such as supply of the culture medium from the culture medium storage unit to the proliferation culture vessel is carried out.

Preferably, the function expressing culture vessel is a differentiation-inducing culture vessel for causing the cells to differentiate, and the differentiation-inducing operation is controlled on the basis of the images of the cells in the differentiation-inducing culture vessel.

Preferably, the cells and the culture medium are stored in a liquid reservoir in the proliferation culture vessel in an initial stage of culture in the proliferation culture vessel.

Preferably, the cells proliferated in the proliferation culture vessel is introduced into the function expressing culture vessel, and the image acquiring unit acquires images of the introduced cells.

Preferably, a used culture medium in the proliferation culture vessel is discharged to a used culture medium storage vessel in the culture medium storage unit.

Preferably, the cells condensed in the proliferation culture vessel are collected in the cell collecting vessel in the culture medium storage unit.

Preferably, the cells are suspension cells.

Preferably, the cells are used in an immune cell therapy.

A cell culture program stored in a computer for carrying out the cell culture according to a third aspect of the invention includes: a step of acquiring images of cells in a culture vessel for culturing cells by an image acquiring unit; a step of determining the culture state of the cells from the images of the cells acquired by the image acquiring unit; and a step of carrying out a culture operation in the culture vessel on the basis of the determination.

A cell culture program stored in a computer for culturing cells according to a fourth aspect of the invention includes; a step of acquiring images of cells in a function expressing culture vessel for causing the cells to express the functions thereof by an image acquiring unit; a step of determining the culture state of the cells from the images of the cells acquired by the image acquiring unit; and a step of carrying out a culture operation in at least one of the function expressing culture vessel and the proliferation culture vessel for causing the cells to proliferate on the basis of the determination.

According to the first aspect of the invention, preferably, the culture vessel is placed on a platform and a culture area is changed by moving part of the platform upward and downward.

Preferably, one of a simple feeding culture and a perfusion culture is selectable.

Preferably, one of an intermittent perfusion culture and a consecutive perfusion culture is selectable.

According to the second aspect of the invention, preferably, the culture vessel is placed on the platform and the culture area is changed by moving part of the platform upward and downward.

Preferably, one of the simple feeding culture and the perfusion culture is selectable.

Preferably, one of the intermittent perfusion culture and the consecutive perfusion culture is selectable.

A cell culture system for culturing cells and monitoring and controlling the culture according to a fifth aspect of the invention includes: an incubator having a plurality of culture units in which culture vessels for culturing cells are disposed respectively so as to be apart from each other for culturing the cells under culture environments independent for the individual culture unit; and a control unit for collecting and accumulating cell culture-related data relating to the cell culture for the individual culture unit in the incubator, monitoring the culture state of the cells for the individual culture unit on the basis of the cell culture-related data and controlling a culture operation of the cells.

Preferably, the control unit includes an operation control panel being installed in a culture room together with the incubator and having a function to control the culture in the respective culture units in the incubator, and a monitoring computer installed out of the culture room for receiving and displaying data in the operation control panel.

Preferably, the cell culture-related data is at least one of identification signs of the cells, the culture medium, the culture vessel, the incubator, the culture unit and an operator, culture environment data in the incubator and the culture unit, and image data of the cells in the culture vessel.

Preferably, a plurality of the incubators are installed, and the operation control panels are connected to the respective incubators and a single monitoring computer is connected to the plurality of operation control panels.

Preferably, a remote monitoring computer is connected to the monitoring computer via a public network.

Preferably, canisters in the incubators, which constitute the culture units, are isolated from each other so as to avoid incoming and outgoing of bacteria or the like.

Preferably, the canisters in the incubator, which constitute the culture units, each include a fan installed therein for introducing air in the incubator toward the canister, and the fans of all the canisters in the single incubator are adapted to stop when a door of the incubator is opened.

Preferably, the canisters in the incubator, which constitute the culture units, are adapted in such a manner that only one of doors of the canisters in the single incubator is opened at a time.

Preferably, the cells are suspension cells.

Preferably, the cells are used in an immune cell therapy.

A cell culture method according to a sixth aspect of the invention for culturing cells and monitoring and controlling the culture including: disposing a incubator having a plurality of culture units in which culture vessels for culturing cells respectively are disposed so as to be apart from each other for culturing the cells under culture environments independent for the individual culture units; collecting and accumulating cell culture-related data relating to the cell culture for the individual culture unit in the incubator, monitoring the culture state of the cells for the individual culture unit on the basis of the cell culture-related data; and controlling a culture operation of the cells.

Preferably, the cell culture-related data is at least one of identification signs of the cells, the culture medium, the culture vessel, the incubator, the culture unit and an operator, culture environment data in the incubator and the culture unit, and image data of the cells in the culture vessel.

Preferably, the cells are suspension cells.

Preferably, the cells are used in an immune cell therapy.

A cell culture program stored in a computer for culturing cells and monitoring and controlling the culture according to a seventh aspect of the invention including: a step of collecting and accumulating cell culture-related data relating to the cell culture individually for a plurality of culture units in a incubator, the culture unit each having a culture vessel for culturing cells disposed therein, the incubator having the plurality of culture units arranged therein so as to be apart from each other for culturing the cells under culture environments independent for the individual culture units; a step of monitoring the culture state of the cells for the individual culture unit on the basis of the cell culture-related data; and a step of controlling a culture operation of the cells for the individual culture unit on the basis of the cell culture-related data.

A cell culture apparatus according to an eighth aspect of the invention is characterized in that a plurality of culture vessels for culturing cells are connected in series, and the respective culture vessels are adapted to culture the cells in different culture environments, transfer the cultured cells to the culture vessel on the downstream side to culture the same.

Preferably, the two culture vessels are installed, and one of the culture vessels is a function expressing culture vessel having a culture environment for causing the cells to express the functions and the other culture vessel is a proliferation culture vessel having a culture environment for causing the cells to proliferate.

Preferably, the function expressing culture vessel is an inducer stimulating culture vessel having a culture environment for stimulating the cells by an inducer for the proliferation.

Preferably, the function expressing culture vessel is a differentiation-inducing culture vessel having a culture environment for causing the proliferated cells to differentiate.

Preferably, the cells are suspension cells.

Preferably, the cells are used in an immune cell therapy.

A cell culture method according to a ninth aspect of the invention includes: culturing cells in different culture environments in a plurality of culture vessels and transferring the cells cultured in one of the culture vessels to different culture vessels on the downstream side in one-to-one correspondence in sequence to carry out the culture.

Preferably, the plurality of culture vessels are two culture vessels and the cells are stimulated by the inducer for the proliferation in one of the two vessels and then the cells are proliferated in the other culture vessel.

Preferably, the plurality of culture vessels are two culture vessels and the cells are proliferated in one of the two culture vessels and then the cells are differentiated in the other culture vessel.

Preferably, the cells are suspension cells.

Preferably, the cells are used in an immune cell therapy.

A cell culture apparatus according to a tenth aspect of the invention includes: a culture vessel for culturing cells; and a platform for placing the culture vessel, and is characterized in that the platform includes a portion which is able to move upward and downward, and the upward and downward movement of the portion which is able to move upward and downward changes the area of the culture vessel placed thereon which is able to be used for the culture.

Preferably, the cells are suspension cells.

Preferably, the cells are used in an immune cell therapy.

Preferably, a culture medium storage unit for storing a culture medium to be supplied to the culture vessel is connected to the culture vessel.

Preferably, the culture medium storage unit and the culture vessel make up a closed system.

Preferably, the culture medium storage unit includes a used culture medium storage vessel which is able to store the used culture medium installed therein together with a culture medium storage vessel which is able to store culture medium to be supplied to the culture vessel, and the used culture medium in a proliferation culture vessel is discharged to the used culture medium storage vessel and is stored therein.

Preferably, an image acquiring unit for acquiring images of cells in the culture vessel and a control unit for determining the culture state of the cells from the images of the cells acquired by the image acquiring unit and causes a culture operation to be carried out on the basis of the determination are provided.

Preferably, the culture vessel includes the proliferation culture vessel for causing the cells to proliferate and a function expressing culture vessel for causing the cells to express the functions, and the image acquiring unit acquires images of the cells in the function expressing culture vessel.

Preferably, the function expressing culture vessel is an inducer stimulating culture vessel for stimulating the cells by an inducer for the proliferation, and the control unit determines the proliferation capability of the cells and the proliferation ability of the cells on the basis of the images of the cells in the inducer stimulating culture vessel and controls timing of changing the area which is available for the culture and the culture operations such as supply of the culture medium from the culture medium storage unit to the proliferation culture vessel.

According to the invention, the culture state of cells are determined from the images of the cells in the culture vessel, and the culture operation according to the culture state is carried out. Therefore, the culture state of the cells is determined in a non-contact state, and hence the cells are prevented from getting damaged, and the operator does not need to carry out the culture operation one by one, whereby the labor of the operator is alleviated. Furthermore, since the adequate culture operation according to the culture state of the cell is realized, an adequate culture operation is achieved. Since the adequate culture operation according to the culture state of the cells is achieved, the culture operation by the hour is enabled, and hence the culture term is shortened.

According to the invention, the culture medium storage unit has a cassette structure and is connected to the culture vessels (the function expressing culture vessel and the proliferation culture vessel). Therefore, the culture vessels are always maintained in an environment optimal for the culture, so that damage to the cells in the culture vessels in association with the change in environment is alleviated, and the aseptic operation for supplying the culture medium to the culture vessel in the clean bench or the like is omitted.

According to the invention, the culture storage unit, the function expressing culture vessel and the proliferation culture vessel make up a closed system. Therefore, the culture storage unit, the function expressing culture vessel and the proliferation culture vessel are maintained under the aseptic conditions.

According to the invention, the cells and the culture medium are stored in the liquid reservoir in the proliferation culture vessel in the initial stage of the culture in the proliferation culture vessel. Therefore, the efficient proliferation of the cells is achieved by maintaining the cell density per area to a density preferable to the proliferation.

According to the invention, the cells proliferated in the proliferation culture vessel are introduced into the function expressing culture vessel, and the images of the cells are acquired by the image acquiring unit. Therefore, the number of cells and the form of the cells are observed by acquiring the cells proliferated in the proliferation culture vessel as the images.

According to the invention, the used culture medium in the proliferation culture vessel is discharged and accumulated in the used culture medium storage vessel in the culture medium storage unit, and hence the cells in the proliferation culture vessel is condensed to increase the cell density. Therefore, the number of times of the operation of centrifugation for collecting the cells is reduced. Consequently, the labor for collecting the cells is saved, and the damage of the cells in association with the centrifugation is reduced.

According to the invention, all the cells condensed in the proliferation culture vessel are collected into the cell collecting vessel in the culture medium storage unit, and hence the cells are collected by mounting the cell collecting vessel directly to the centrifuge. Therefore, the labor for collecting the cells is saved.

According to the invention, the area of the liquid reservoir for storing the cells and the culture medium in the culture vessel is able to be changed by the predetermined area, and hence the cell density per area during the culture is maintained at a density preferable for the proliferation. Therefore, efficient proliferation of the cells is achieved.

According to the invention, the operation control panel and the monitoring computer collect and accumulate the cell culture-related data relating to the cell culture individually for the each culture unit in the incubator. Therefore, the culture log relating to the cells cultured in the arbitrary culture unit is adequately known. The operation control panel and the monitoring computer monitor the culture state of the cells on the basis of the cell culture-related data for the individual culture unit in the incubator. Therefore, trouble in the culture state may be monitored individually for the each culture unit. Furthermore, the operation control panel and the monitoring computer control the operation of cell culture such as the change of the culture medium (replacement of the culture medium cassette) and collection of the cells after having completed the culture (collection of the cells by the culture bag or the cell collecting bag) individually for the each culture unit (the canister and the culture cassette) in the incubator. Therefore, the operation schedule for the operation (work) carried out by the operator individually for the each culture unit in the incubator is easily prepared. The control unit includes the operation control panel being installed in the culture room together with the incubator and having a function to control the culture in the each culture unit (the canister and the culture cassette) in the incubator and the monitoring computer being installed in the monitor room other than the culture room and receiving and saving the data that the operation control panel has and making the same available for display (inspection). Therefore, the culture state of the cells in the culture unit in the incubator in the culture room may be observed, monitored and controlled in the monitor room other than the culture room by the monitoring computer. With this control, the log or the like is automatically recorded and stored, and occurrence of intentional alteration or erroneous recording is prevented.

According to the invention, the canisters in the incubator which constitutes the culture units are each isolated to avoid entry of the cells and/or bacteria by the air-intake filter and the exhaust filter. Therefore, the cells in the culture bag and the cell inoculation cassette stored in the each canister are prevented from being contaminated by bacteria. The blast fans of all the canisters in the single incubator are configured to stop when the main body door of the incubator is opened. Therefore, the sealed state of the each canister in the incubator is maintained even when the main body door of the incubator is opened, so that the independent culture environment for the each canister is preferably secured, so that the fluctuation of the culture environments in the canisters are restrained. Only one of the canister doors of the canisters in the single incubator is allowed to be opened. Therefore, there is no probability that the two or more canister doors of the canisters are opened at a time in the single incubator, so that the mix-up of the culture bags and the cell inoculation cassettes among the canisters is prevented, and the cross-contamination of the cells is avoided.

According to the invention, the antibody stimulation and the cell proliferation in the initial stage of culture in the cell culture bag are carried out in the same culture bag, and the area of the liquid reservoir for storing the cells and the culture medium in the culture bag is changed by a predetermined area. Therefore, efficient proliferation of the cells is achieved by maintaining the cell density per area during the proliferation to a density preferable for the proliferation.

BRIEF DESCRIPTION OF THE DRAWINGS

FIG. 4 is a perspective view showing a culture bag tray, a culture medium cassette and a cell inoculation cassette in FIG. 3, respectively;

DESCRIPTION OF THE PREFERRED EMBODIMENTS

Figure 1A:
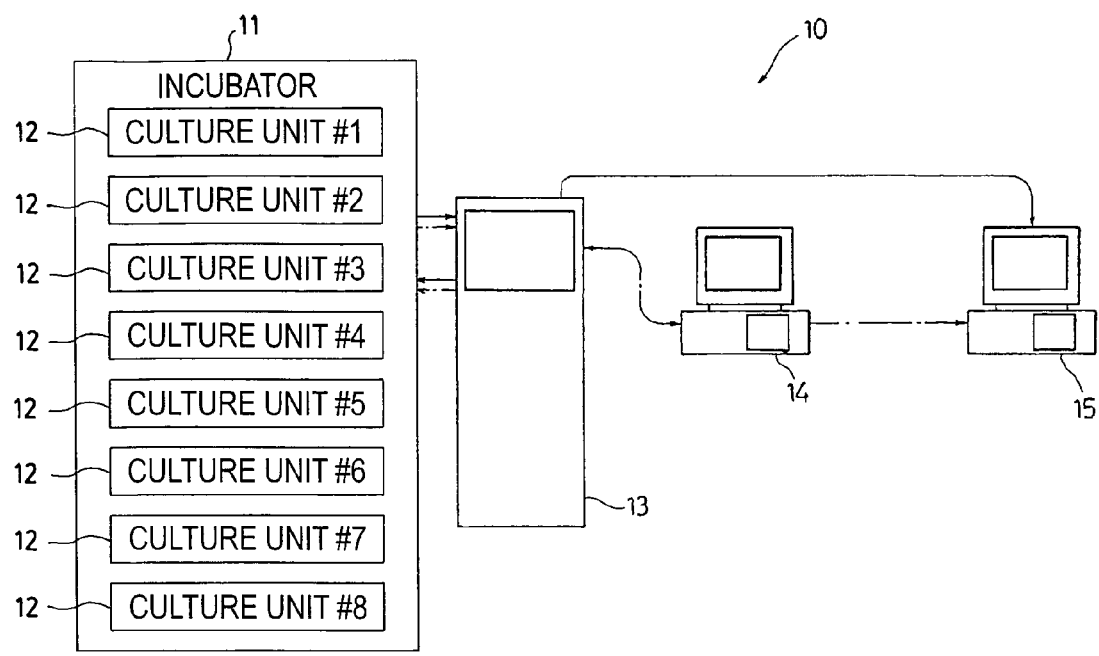
FIG. 1A is a configuration drawing showing a cell culture apparatus according to a first embodiment of the invention.

Referring to the drawings, best modes for carrying out the invention will be described below.

[A] First Embodiment

FIG. 1 to FIG. 20

Figure 1B:
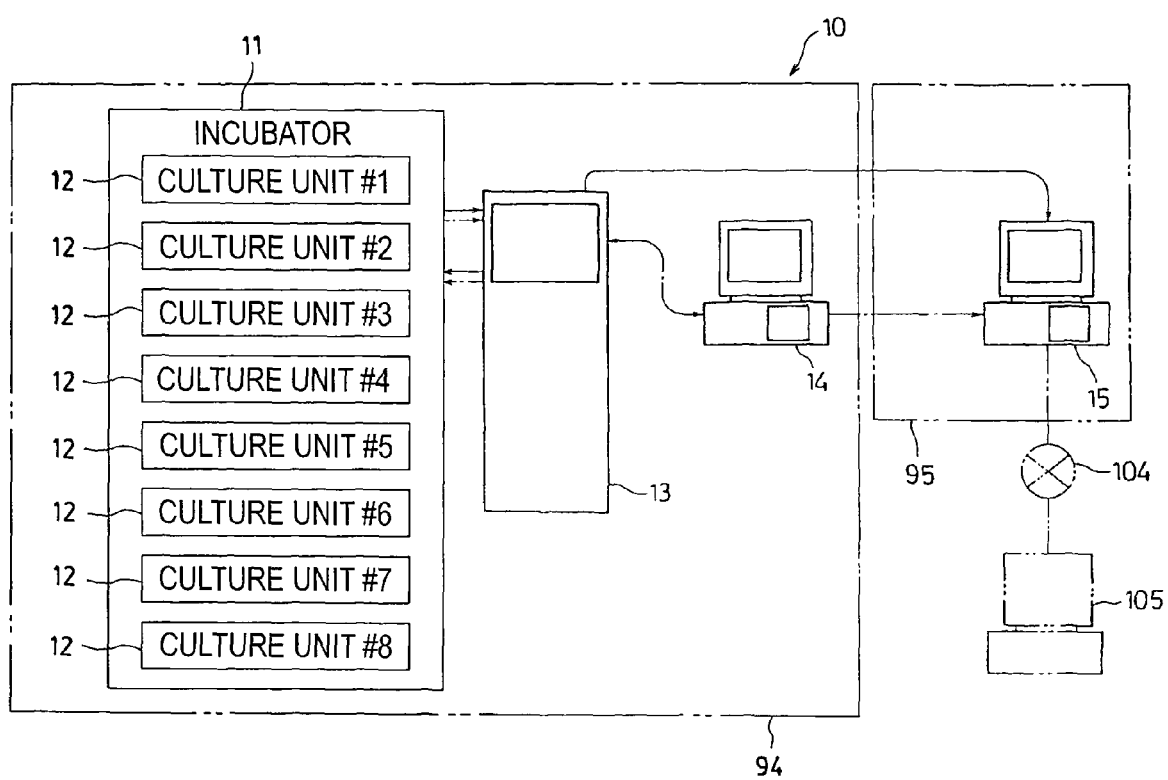
FIG. 1B is a configuration drawing showing a cell culture system according to the first embodiment of the invention.
Figure 2:
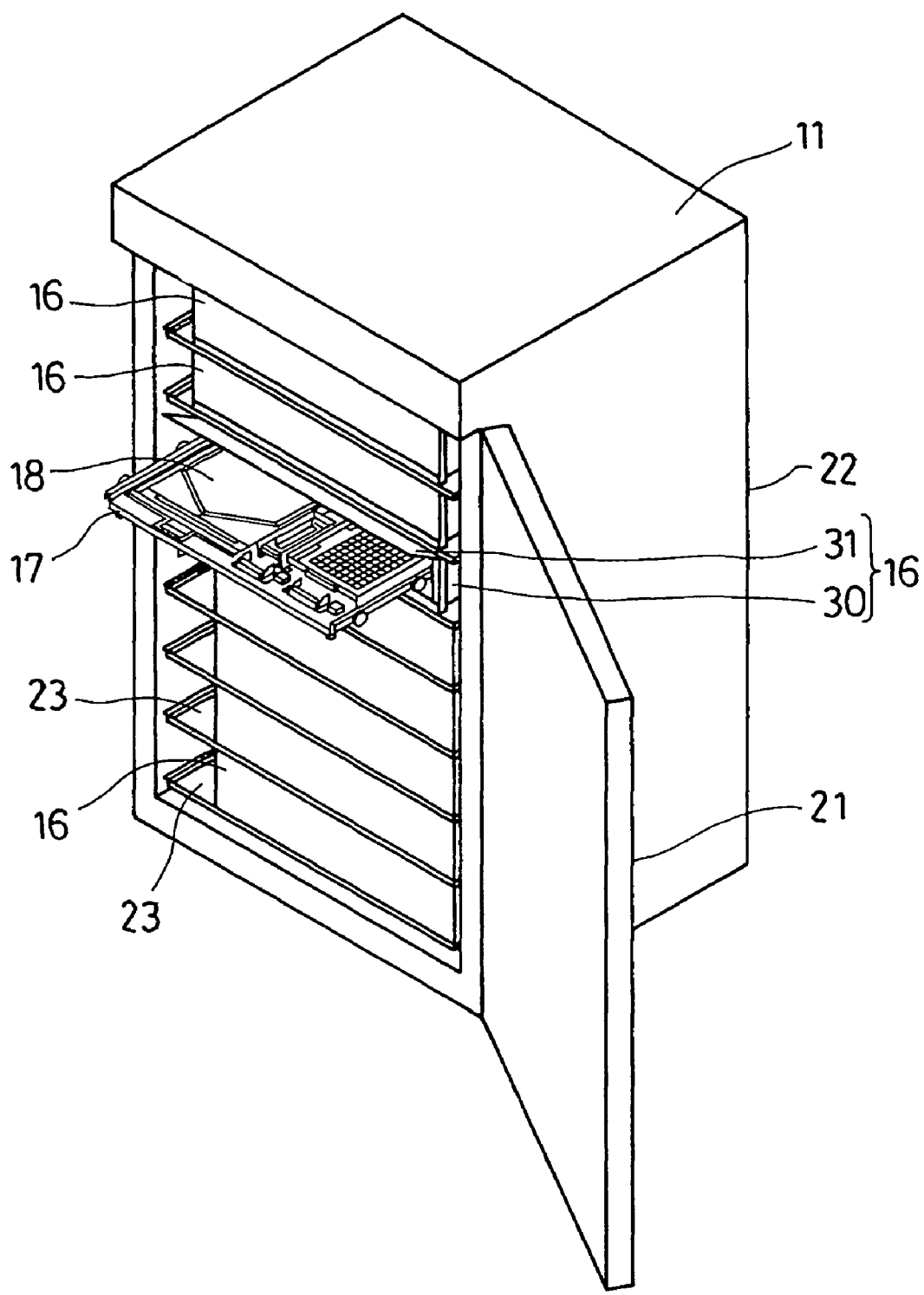
FIG. 2 is a perspective view illustrating an incubator in FIG. 1.
Figure 5:
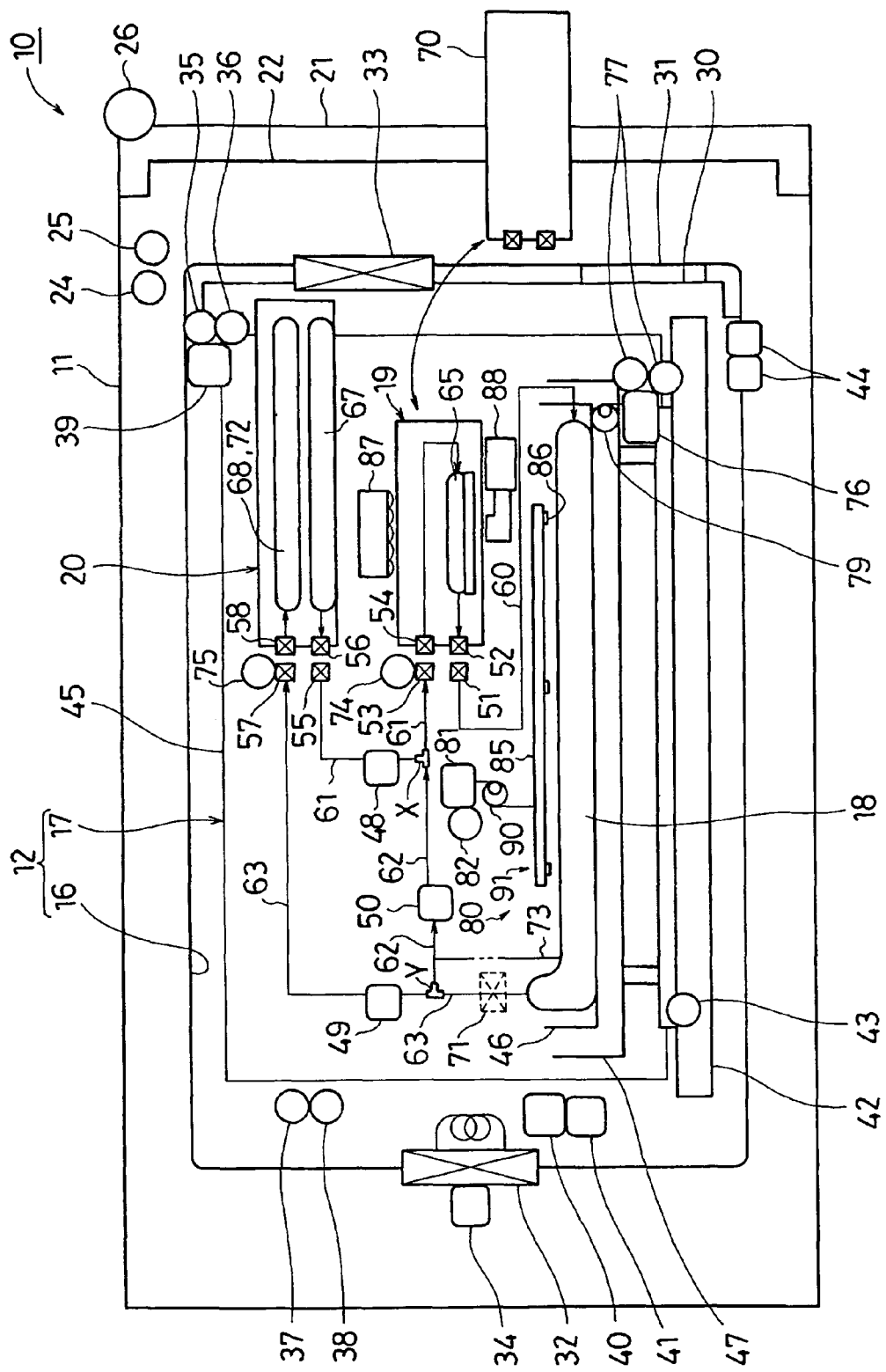
FIG. 5 is a layout drawing showing a configuration of a culture unit including a canister in the incubator in FIG. 2 and the culture cassette stored in the canister.

FIG. 1A is a configuration drawing showing a cell culture apparatus according to a first embodiment of the invention and FIG. 1B is a configuration drawing showing a cell culture system according to the first embodiment of the invention. FIG. 2 is a perspective view illuartaring an incubator in FIGS. 1A and 1B. FIG. 5 is a layout drawing showing a configuration of a culture unit including one canister in the incubator and a culture cassette stored in the canister.

A cell culture apparatus 10 shown in FIG. 1A is specifically adapted to culture suspension cells used for an immune cell therapy, and includes an incubator 11 provided with a plurality of (eight, for example) culture units 12, an operation control panel 13 for controlling an operation of the incubator 11 and the culture units 12, an image processing computer 14 for processing images of cells, and a monitoring computer 15 being connected to the operation control panel 13 and the image processing computer 14 for monitoring the incubator 11 and the culture units 12. The operation control panel 13 and the image processing computer 14 function as a control unit.

The cell culture apparatus 10 is also implemented as a cell culture system. The cell culture system 10 is specifically adapted to culture the suspension cells used for the immune cell therapy, and includes the incubator 11, the operation control panel 13, the image processing computer 14 and the monitoring computer 15 like the cell culture apparatus 10 shown above. As shown in FIG. 1B, the incubator 11, the operation control panel 13 and the image processing computer 14 are installed in a culture room (clean room) 94 suitable for the cell culture, and the monitoring computer 15 is installed in a monitor room 95 other than the culture room 94. The incubator 11 includes a plurality of (eight, for example) the culture units 12 in which a culture vessel for culturing cells (a proliferation culture vessel, an inducer stimulating culture vessel described later) arranged so as to apart from each other. In this incubator 11, cells in the culture vessels are cultured under culture environments independent for the individual culture units 12.

The operation control panel 13 controls the operation of the incubator 11 and the culture units 12, and monitor and control the cell culture for the individual culture units 12 in the incubator 11. The image processing computer 14 processes images of the cells under culture for the individual culture units 12 in the incubator 11, and functions as a control unit for controlling the culture operation. The monitoring computer 15 is connected to the operation control panel 13 and the image processing computer 14, receives and stores data from the operation control panel 13 and the image processing computer 14, makes the data available for display (inspection), and serves as a control unit for monitoring and controlling the cell culture.

The known suspension cells include peripheral blood mononuclear cells, LAK cells (Lymphokine Activated killer cells), neural stem cells, and ES cells. These types of suspension cells are referred simply to as "cells", hereinafter. These cells are stimulated and cultured with inducers which are suitable for the individual cells. The inducers differ from cell to cell. For example, the suitable inducer for LAK cells is anti-human CD3 antibody, the suitable inducer for the neural stem cells is epidermal growth factor such as EGF, and the suitable inducer for ES cells is fibroblast growth factor such as FGF-8b. The cell culture apparatus 10 is also applicable to a case of culturing adherent cells other than the suspension cells.

The culture unit 12 includes a plurality of (eight, for example) canisters 16 (FIG. 2 and FIG. 5) separated so as to be apart from each other in the incubator 11, and culture cassettes 17 (FIG. 2 and FIG. 3) to be stored in the canisters 16 individually. The culture cassette 17 includes, a culture bag 18 as a proliferation culture vessel, a cell inoculation cassette 19 as an inducer stimulating culture vessel, and a culture medium cassette 20 as a culture medium storage unit. Cells in the culture vessels (culture bag 18 and cell inoculation cassette 19) are cultured under the independent culture environments for the individual canisters 16.

As shown in FIG. 2, the incubator 11 includes a plurality of tiers of shelves 23 in an incubator body 22 having an openable-closable main body door 21 installed therein, and the canisters 16 are arranged on the shelves 23 one by one. The incubator 11 maintains the environment (temperature, humidity, and $CO_2$ concentration) in the incubator body 22 in an environment required for the cell culture in as state in which the main body door 21 is closed.

Figure 6:
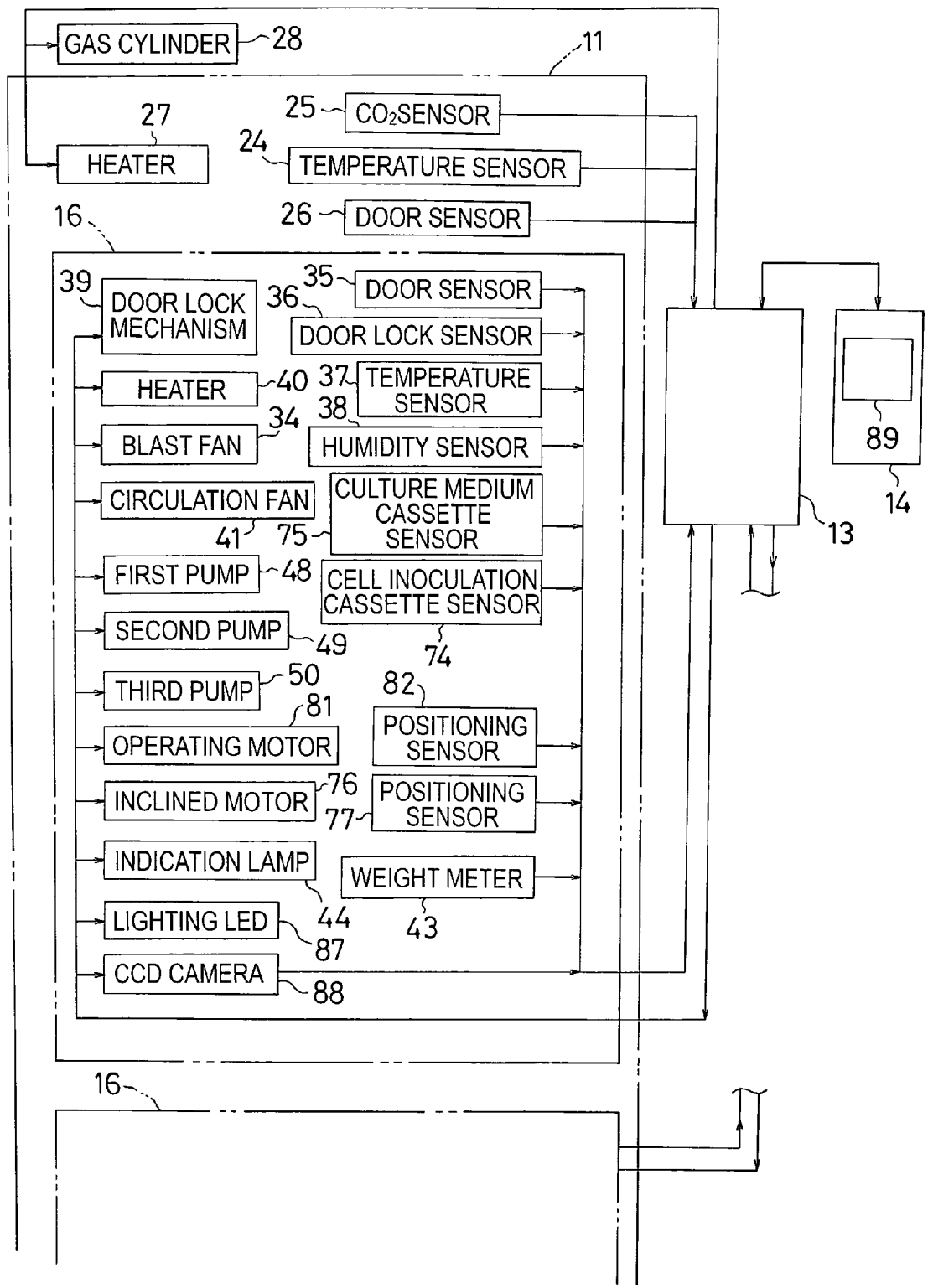
FIG. 6 is a block diagram showing a control system of the culture unit in FIG. 5.

Therefore, as shown in FIG. 5 and FIG. 6, a temperature sensor 24, a $CO_2$ sensor 25, a door sensor 26 and a heater 27 are arranged in the incubator body 22, and a gas cylinder 28 installed outside is coupled to the incubator body 22. Signals from the temperature sensor 24, the $CO_2$ sensor 25 and the door sensor 26 are transmitted to the operation control panel 13. The operation control panel 13 controls the heater 27 on the basis of the temperature signal from the temperature sensor 24, and controls the amount of the $CO_2$ gas supplied from the gas cylinder 28 to the incubator body 22 on the basis of the $CO_2$ concentration signal from the $CO_2$ sensor 25.

As shown in FIG. 5 and FIG. 6, the canister 16 has an openable-closable canister door 31 mounted to a canister body 30, and an air-intake filter 32 and an exhaust filter 33 are installed to the canister body 30 and a blast fan 34 is installed on the air-intake filter 32 side of the canister body 30.

The air-intake filter 32 and the exhaust filter 33 are filters for removing bacteria, and prevent entry of bacteria from the incubator body 22 into the canister 16 when air and $CO_2$ gas in the incubator body 22 is taken into the canister 16 by the operation of the blast fan 34. The operation of the blast fan 34 is controlled by the operation control panel 13 and, when a signal indicating that the main body door 21 of the incubator 11 is opened is transmitted from the door sensor 26 to the operation control panel 13, the operation of the blast fan 34 is stopped and the sealed state of the canister 16 is ensured.

The function of the air-intake filter 32 and the exhaust filter 33 to prevent entry of bacteria from the incubator body 22 into the canister 16, and the securement of the sealing property of the canister 16 due to the operation stop of the blast fan 34 bring the interiors of the individual canisters 16 to independent culture environment. Accordingly, cells in the culture cassette 17 stored in one single canister 16 in the incubator 11 are isolated from cells in other canisters 16, and cells in the culture cassette 17 stored in the canister 16 is prevented from being contaminated by bacteria. So-called cross-contamination, which is the contamination by cells of other patients, is also prevented.

The canister body 30 is further provided with a door sensor 35, a door lock sensor 36, a temperature sensor 37, a humidity sensor 38, a door lock mechanism 39, a heater 40 and a circulation fan 41. The operation control panel 13 controls the heater 40 on the basis of the temperature signal from the temperature sensor 37. The operation control panel 13 controls the operation of the circulation fan 41, and circulates air and $CO_2$ gas in the canister 16. The humidity sensor 38 detects the humidity in the canister 16, transmits the same to the operation control panel 13, and detects the trouble therein. In this manner, the interior of the canister 16 is maintained in an environment optimal for the cell culture.

The operation control panel 13 controls the operation of the door lock mechanism 39 so as to prevent two or more canister doors 31 from opening at the same time in the single incubator 11. Accordingly, erroneous transportation of cells or the culture medium between the different canisters 16 is prevented. The locking operation of the door lock mechanism 39 is detected by the door lock sensor 36, and is transmitted to the operation control panel 13. The opened or closed state of the canister door 31 is detected by the door sensor 35, and is transmitted to the operation control panel 13.

A stage 42 for supporting the culture cassette 17 to be stored in the canister 16 is provided at the lower portion in the canister body 30 shown in FIG. 5, a weight meter 43 is installed on the stage 42. The weight meter 43 is adapted to weigh the culture bag 18 of the culture cassette 17 stored in the canister 16 and, actually, measures the amount of culture medium to be supplied from the culture medium cassette 20 to the culture bag 18. The measured value of the weight meter 43 is also transmitted to the operation control panel 13. A indication lamp 44 is provided in the canister body 30. When culture is carried out automatically in some canisters 16, the indication lamps 44 of the corresponding canisters 16 are illuminated, for example, in red, and the indication lamps 44 of the canisters 16 to which the operation instruction is issued and the canister 16 in which the incubation cassette 17 is not mounted are illuminated in green. Accordingly, the culture environment independent from other canisters 16 is secured for the canisters 16 in which an automatic culture is carried out, so that the cross contamination or mix-up with specimen (cells) stored in other canisters 16 may be prevented.

The culture cassette 17 will now be described.

Figure 3:
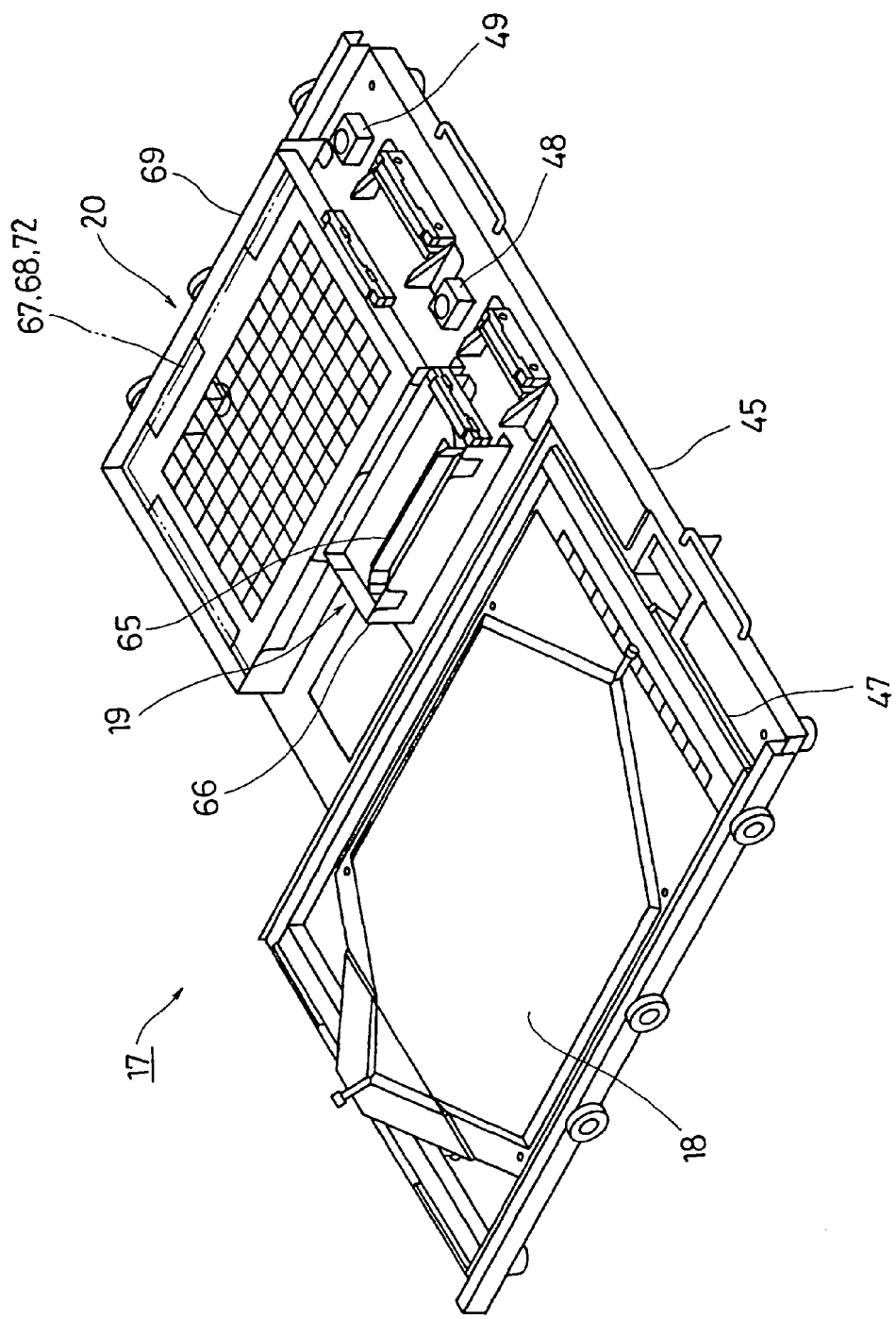
FIG. 3 is a perspective view showing the culture cassette stored in a canister in an incubator in FIG. 1.

As shown in FIG. 3 and FIG. 5, the culture cassette 17 is composed of the culture bag 18, the cell inoculation cassette 19, and the culture medium cassette 20 mounted to a large tray 45, and is a culture vessel in which the culture bag 18 and the cell inoculation cassette 19 culture cells. The cell inoculation cassette 19 is a function expressing culture vessel for causing the cells to express the function (for example, to cause the cells to proliferate, to cause the cells to differentiate (described later)), and is an inducer stimulating culture vessel for stimulating the cells by the inducer for proliferation in this embodiment. The culture bag 18 is a proliferation culture vessel for causing the cells to proliferate stimulated by the inducer in the cell inoculation cassette 19.

The culture bag 18 is a flexible disposable vessel for storing culture suspension in which cells are inoculated, is placed on a culture bag tray 47 shown in FIG. 4A, interposing a platform 46 (FIG. 5) between the culture bag 18 and the culture bag tray 47, and the culture bag tray 47 is detachably mounted to the large tray 45 shown in FIG. 3 and FIG. 5. The culture bag 18 is a bag formed of, for example, an oxygen permeable material. As shown in FIG. 5, a first pump 48, a second pump 49 and a third pump 50 are arranged on the large tray 45. One end of the culture bag 18 is connected to a seventh connector 57 via the second pump 49 using a tube 63. The other end of the culture bag 18 is connected to a first connector 51 using a tube 60. The first pump 48, the second pump 49 and the third pump 50 are preferably of a peristaltic-type pump from the convenience of replacement of a sterile tube.

In the large tray 45, one end of the tube 61 is connected to the third connector 53 and the other end thereof is connected to a fifth connecter 55. The tube 61 is disposed on a rotating portion, not shown, of the first pump 48. The tube 63 is connected to the seventh connector 57 at one end as described above and to the culture bag 18 at the other end. The tube 63 is disposed on a rotating portion, not shown, of the second pump 49. One end of the tube 62 is connected to the tube 61 via the connecter X and the other end thereof is connected to the tube 63 via connecter Y. The tube 62 is disposed on a rotating portion, not shown, of the third pump 50.

As shown in FIG. 4C, the cell inoculation cassette 19 is formed into a cassette structure by immobilizing the inducer on the inner side of the bottom surface of an inducer stimulation vessel 65, adding the culture medium into the inducer stimulation vessel 65, inoculating cells on the culture medium, and installing the inducer stimulation vessel 65 in a set frame 66. The operation to add the inducer, the culture medium and the cells into the inducer stimulation vessel 65 is carried out under aseptic conditions in a clean bench or a safety cabinet (hereinafter, referred to as clean bench etc. in this embodiment). The mixed liquid of the culture medium and cells is referred to as culture suspension.

As shown in FIG. 3, the cell inoculation cassette 19 is detachably mounted to the large tray 45. At this time, as shown in FIG. 5, the second connector 52 and the fourth connector 54 of the cell inoculation cassette 19 are coupled to the first connector 51 and the third connector 53 of the large tray 45 under the aseptic conditions, respectively. In other words, the first connector 51 and the second connector 52 are coupled, for example, by inserting a rubbery joint on one of those to a needle joint on the other one of those under the aseptic conditions. The coupling of the third connector 53 and the fourth connector 54 is the same.

By the coupling between the first connector 51 and the second connector 52, the cell inoculation cassette 19 and the culture bag 18 in the different culture environment, that is, the cell inoculation cassette 19 having a culture environment for stimulating cells by the inducer to cause the cells to express the proliferating function and the culture bag 18 having a culture environment for causing the cells to proliferate are connected using the tube 60. Therefore, the cells which are stimulated by the inducer in the cell inoculation cassette 19 and has started the proliferation may be transferred to culture bag 18 to cause the cells only to proliferate in the culture bag 18.

As shown in FIG. 4B, the culture medium cassette 20 is formed into a cassette structure with mounting a culture medium bag 67 as a culture medium storage vessel and a used culture medium bag 68 as a used culture medium storage vessel on a culture medium bag tray 69. The culture medium bag 67 is adapted to store the culture medium to be supplied to the culture bag 18 and the cell inoculation cassette 19. The used culture medium bag 68 is adapted to store the used culture medium (supernatant) discharged from the culture bag 18. With the culture medium cassette 20 having the cassette structure, change and supply of the culture medium are enabled only by mounting the culture medium cassette 20 to the culture cassette 17 in the canister 16 in a state of maintaining the culture bag 18 in the canister 16.

The culture medium cassette 20 is detachably mounted to the large tray 45 (FIG. 3). At this time, as shown in FIG. 5, a sixth connector 56 and an eighth connector 58 of the culture medium cassette 20 are coupled to the fifth connecter 55 and the seventh connector 57 of the large tray 45 under the aseptic conditions respectively in the same manner as the case of the first connector 51 and the second connector 52. By the coupling between the sixth connector 56 and the fifth connecter 55, the culture medium bag 67 and the cell inoculation cassette 19 are connected. By the coupling between the seventh connector 57 and the eighth connector 58, the used culture medium bag 68 and the culture bag 18 are connected.

With the connection among the culture bag 18, the cell inoculation cassette 19 and the culture medium cassette 20 as described above, a closed system in which the culture medium in the culture medium bag 67 in the culture medium cassette 20 is supplied to the culture bag 18 via the cell inoculation cassette 19 when the first pump 48 is activated, and the used culture medium in the culture bag 18 is discharged to the used culture medium bag 68 in the culture medium cassette 20 when the second pump 49 is activated is established. With the establishment of the closed system, the system (the culture bag 18, the cell inoculation cassette 19 and the culture medium cassette 20) is maintained under the aseptic conditions.

The cell inoculation cassette 19 described above is replaced by a dummy cassette 70 in a stage where there is no more cell therein. Accordingly, the inducer in the cell inoculation cassette 19 is prevented from being transferred to the interior of the culture bag 18. The culture medium cassette 20 is replaced by a new culture medium cassette 20 having the culture medium bag 67 filled with the culture medium and an empty used culture medium bag 68 in a stage where the culture medium bag 67 becomes empty. This replacement is carried out by the operator. The dummy cassette 70 simply has a function as a flow channel for allowing the culture medium to flow.

The culture (cell proliferation) in the culture bag 18 includes a feeding culture in which the first pump 48 is activated to supply (feed) the culture medium in the culture medium bag 67 in the culture medium cassette 20 to the culture bag 18 so that the proliferation of cells is achieved, a perfusion culture in which the first pump 48 and the second pump 49 are activated to discharge the used culture medium in the culture bag 18 to the used culture medium bag 68 in the culture medium cassette 20 and to supply the culture medium in the culture medium bag 67 to the culture bag 18 so that the proliferation of cells is achieved, a shaking culture using a shaking device 80 described later and a static culture in which the shaking operation is not carried out. The perfusion culture includes an intermittent perfusion culture in which discharge of the used culture medium and supply of the culture medium are carried out alternately, and a consecutive perfusion culture in which the discharge of the used culture medium and the supply of the culture medium are carried out simultaneously. In the consecutive perfusion culture, a filter 71 for preventing transfer of cells is normally disposed between the culture bag 18 and the second pump 49 in the tube 63 to prevent the cells in the culture bag 18 from being discharged to the used culture medium bag 68.

The third pump 50 is activated, for example, in the case of observing the cells proliferating in the culture bag 18 using the images. In other words, the cells in the culture bag 18 is introduced from the culture bag 18 to the cell inoculation cassette 19 or the dummy cassette 70 via the tube 63, the tube 62 and the tube 61 when the filter 71 is not disposed in the tube 63, and is shot by a CCD camera 88, described later, so that the number of proliferated cells or the like is observed. When the filter 71 is disposed in the tube 63, the upstream side of the third pump 50 is connected to the culture bag 18 via a bypass tube 73, and the cells in the culture bag 18 are introduced into the cell inoculation cassette 19 or the dummy cassette 70 via the bypass tube 73 and the tube 62, and are observed using the CCD camera 88.

The used culture medium in the culture bag 18 is discharged to the used culture medium bag 68 in the culture medium cassette 20 after having completed the proliferation of cells in the culture bag 18, and the cells in the culture bag 18 is condensed. The discharge of the used culture medium is carried out by activating the second pump 49 until the amount of the culture suspension in the culture bag 18 is reduced to about ½ to ⅓ in quantity by the control of the operation control panel 13 on the basis of the value measured by the weight meter 43. By the condensation of the cells in the culture bag 18, the number of times of centrifugation carried out by a centrifuge for the purpose of wash and condensation of cells, carried out later, is reduced.

In the culture medium cassette 20, it is also possible to replace the used culture medium bag 68 by a cell collecting bag 72 as a cell collecting vessel which is attachable to the centrifuge after having condensed the cells in the culture bag 18 as described above, and then supply the culture suspension in which the cells are condensed in the culture bag 18 (the culture medium and the cells) into the cell collecting bag 72 by activating the second pump 49 provided that the filter 71 is not disposed in the tube 63. Accordingly, collection of the cells in the bag which is attachable to the centrifuge may be carried out within the canister 16, which is a space in the closed system, so that the labor for collecting the cells is saved.

As shown in FIG. 5 and FIG. 6, the large tray 45 of the culture cassette 17 stored in the canister 16 is provided with a cell inoculation cassette sensor 74 which detects the fact that the cell inoculation cassette 19 or the dummy cassette 70 is mounted to the large tray 45 and a culture medium cassette sensor 75 for detecting the fact that the culture medium cassette 20 is mounted on the large tray 45. Signals from the sensors 74 and 75 are transmitted to the operation control panel 13. The operation control panel 13 confirms the fact that the cell inoculation cassette 19 or the dummy cassette 70 is mounted to the large tray 45 of the culture cassette 17 and the fact that the culture medium cassette 20 is mounted, and then activates the first pump 48, the second pump 49 and the third pump 50.

As shown in FIG. 5, the culture cassette 17 is stored within the canister 16, and the culture cassette 17 is supported on the stage 42 of the canister 16, and the stage 42 is provided with an inclined motor 76, a cam mechanism 79 and a positioning sensor 77 below a position where the culture bag tray 47 of the culture cassette 17 is installed. A part (elevating unit, not shown), of the platform 46 for placing the culture bag 18 on the culture bag tray 47 directly is adapted to be able to be moved upward and downward. The inclined motor 76 rotates the cam mechanism 79 to move the elevating unit of the platform 46 upward and downward. The position of the elevating unit is detected by the positioning sensor 77, and is transmitted to the operation control panel 13. The inclined motor 76 is controlled by the operation control panel 13 so as to move the elevating unit of the platform 46 downward in an initial stage of culture in the culture bag 18. Accordingly, a liquid reservoir 78 (FIGS. 8A and 8B, FIGS. 9A and 9B) is formed in the culture bag 18.

In the initial stage of culture in the culture bag 18, the culture suspension from the cell inoculation cassette 19 (the culture medium and the cells) is retained in the liquid reservoir 78, so that the cell density per area in the culture bag 18 is maintained at a density suitable for the proliferation and hence the cells efficiently proliferate in the initial stage of the culture. In the middle stage and the later stage of the culture in which the amount of the culture suspension in the culture bag 18 is increased to a level at least equal to a predetermined amount a (described later), the inclined motor 76 moves the elevating unit of the platform 46 upward via the cam mechanism 79 to bring the culture bag 18 into a horizontal state to eliminate the liquid reservoir 78.

Figure 7A:
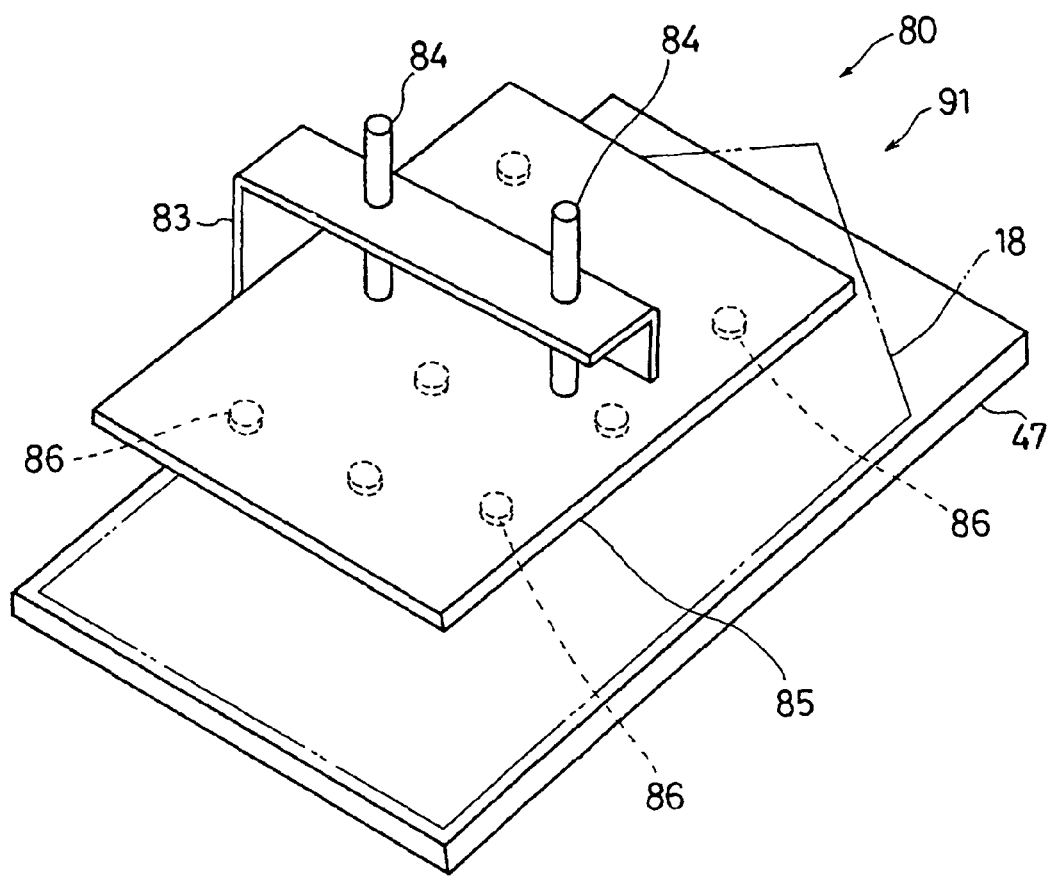
FIG. 7A is a perspective view of a shaking mechanism of a shaking device in FIG. 5.
Figure 7B:
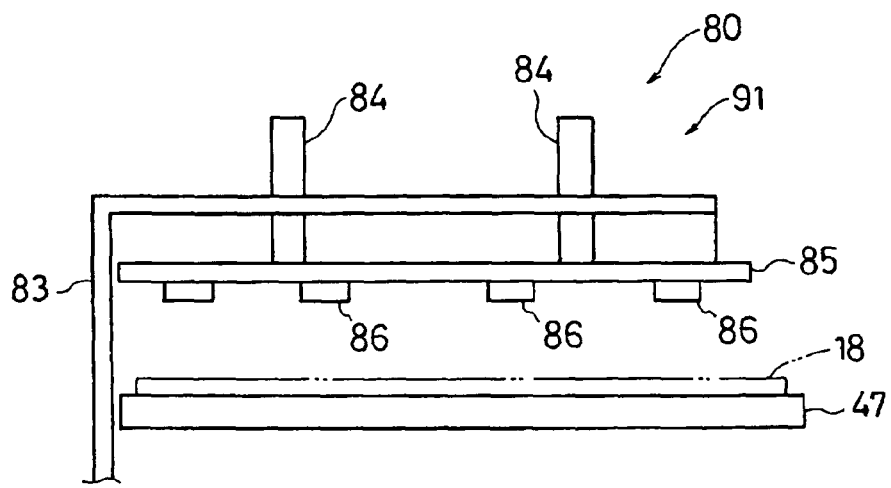
FIG. 7B is a side view of the shaking mechanism of the shaking device in FIG. 5.

As shown in FIG. 5, a shaking mechanism 91 of the shaking device 80 is provided in the canister 16 above the position where the culture bag tray 47 of the culture cassette 17 is installed as a pressing unit. The shaking device 80 includes the shaking mechanism 91, an operating motor 81, a cam mechanism 90 and a positioning sensor 82. As shown in FIG. 7, the shaking mechanism 91 includes an operating plate 85 disposed in an apparatus frame 83 so as to be capable of moving upward and downward via a guide rod 84, and a plurality of projections 86 provided on the bottom surface of the operating plate 85. When the operating plate 85 is moved upward and downward alternately on the basis of the action of the cam mechanism 90 (FIG. 5) by the operating motor 81, the projections 86 of the operating plate 85 presses the culture bag 18 positioned below the shaking mechanism 91 repeatedly, that is, repeats pressing and releasing with respect to the culture bag 18. Accordingly, the culture suspension in the culture bag 18 is stirred, and the cells in the culture bag 18 float and move in the culture suspension, so that the distribution of the cells and the concentration of the components of the culture medium in the culture bag 18 are homogenized, whereby the oxygen supply capacity is improved and hence the proliferation of the cells is promoted.

As shown in FIG. 6, the position of the operating plate 85 is detected by the positioning sensor 82, and is transmitted to the operation control panel 13, whereby the operating motor 81 is controlled by the operation control panel 13. The cell culture (shaking culture) in the culture bag 18 using the shaking device 80 described above may be carried out before the culture suspension is filled in the culture bag 18 to approximately a maximum level, or may be carried out after having filled therein to approximately the maximum level.

As shown in FIG. 5, an lighting LED 87 and the CCD camera 88 as an image acquiring unit are installed in the canister 16 above and below the position where the cell inoculation cassette 19 or the dummy cassette 70 of the culture cassette 17 is arranged, respectively. The lighting LED 87 illuminates the cell inoculation cassette 19 or the dummy cassette 70 from above. The CCD camera 88 shoots the cells in the cell inoculation cassette 19 or the dummy cassette 70 from below to acquire the image thereof. The illuminating operation of the lighting LED 87 and the shooting operation of the CCD camera 88 are controlled by the operation control panel 13 (FIG. 6), and images of the cells in the cell inoculation cassette 19 or the dummy cassette 70 are acquired at predetermined time intervals (every 6 hours, for example). The cell images shot at the predetermined time intervals are stored in an image memory circuit 89 of the image processing computer 14.

The image processing computer 14 carries out image processing, for example, binarization or multithresholding, for the cell images shot at the predetermined time intervals stored in the image memory circuit 89, so that an average value of the projected areas of the single cells and the increasing rate of the non-single cell, which is a cell aggregate formed of a plurality of single cells, are calculated as evaluation parameters of the cell culture. The average value of the projected areas of the single cells (the average projected area of the single cell) is calculated from the cell image taken when twenty-four hours has elapsed from the moment when the culture is started after having mounted the cell inoculation cassette 19 to the culture cassette 17 and stored the culture cassette 17 in the canister 16.

Determination of whether the cell is the non-single cell described above or not is achieved in such a manner that the cell having a projected area at least equal to 100 $\mu m^2$ is determined as the non-single cells since the projected area of the single cell in the initial stage of culture is smaller than 100 $\mu m^2$. The change of the ratio of the non-single cells with respect to all the cells is computed from follow-up images of the cells (for example, images of the cells after having elapsed 24 hours, 48 hours and 72 hours from the start of culture) to calculate the increasing rate of the non-single cell.

The image processing computer 14 calculates a lag time from the average projected area of the single cell and estimates the start time of the proliferation of the cells. The lag time means a time length of an induction phase required from inoculation of cells in the inducer stimulation vessel 65 in the cell inoculation cassette 19 until the proliferation is started. The image processing computer 14 determines whether the culture state of the cells, that is, whether the cell has a capability to proliferate by the stimulation from the inducer or not, from the timing when the cells has started to proliferate. Then, the image processing computer 14 transmits the result of determination of the cells (for example, "YES" when the cells have a capability to proliferate and "NO" when the cells have no capability to proliferate) to the operation control panel 13. When the operation control panel 13 receives a signal indicating that the capability of proliferation of the cells in the inducer stimulation vessel 65 in the cell inoculation cassette 19 is determined to be remarkably low, the operation control panel 13 displays the state of the corresponding cells. The cells demonstrating too long lag time are cells which are remarkably hard to get stimulated by the inducer, and hence are determined that the capability of proliferation is low.

The image processing computer 14 calculates a minimum doubling time of the cells from the increasing rate of the non-single cell. The doubling time in this specification means a time period required for the number of cells at a certain time instant to be increased to two times the number of cells. The image processing computer 14 determines the culture state of the cells, that is, the proliferation ability of the cells from the minimum doubling time and transmits the same to the operation control panel 13. Then, the operation control panel 13 that has received the signal from the image processing computer 14 decides the timing for moving the cells from the cell inoculation cassette 19 to the culture bag 18 or the feeding velocity for feeding the culture medium to the culture bag 18 on the basis of the proliferation ability of the cells. The cells demonstrating a too long minimum doubling time is determined to be cells having a remarkably low proliferation ability.

The operation control panel 13 and the image processing computer 14 functioning as control units include a CPU for executing computation or control, a storage device (memory) for storing a processing program or data, and a input/output circuit for the connection with the input devices such as a keyboard, a mouse or a touch panel for supplying data or commands and the output devices such as a monitor. The image processing computer 14 also includes the image memory circuit 89 for storing the image data from the CCD camera 88.

The storage device of the image processing computer 14, stores a program for processing (for example, binarization or multithresholding) the images of the cells in the cell inoculation cassette 19 shot at the predetermined time intervals by the CCD camera 88, calculating evaluation parameters for the cell culture (the average projected area of the single cell, the increasing rate of the non-singe cell), and determining the culture state of the cells (the proliferation capability of the cells, and the proliferation ability of the cells) from the evaluation parameters of the cell culture.

The storage device of the operation control panel 13 stores a equipment control program for controlling equipment (for example, the first pump 48 and the second pump 49) relating to the incubator 11, the canister 16 and the culture cassette 17 according to the culture state of the cells and carrying out the culture operation. The storage device of the operation control panel 13 also stores a program for controlling the equipment relating to the incubator 11, the canister 16 and the culture cassette 17 on the basis of the signals from respective sensors in the incubator 11, the canister 16 and the culture cassette 17, such as controlling the CCD camera 88 at predetermined time intervals and acquiring the images of the cells.

In the cell culture system 10, the storage device of the operation control panel 13, which is one of the operation control panel 13 and the monitoring computer 15 as the control units, stores a program for collecting and accumulating cell culture related-data relating to the cell culture for the each canister 16 in the incubator 11 and for the each culture cassette 17 stored in the canister 16, a program for monitoring the culture state of the cells for the each canister 16 and the each culture cassette 17 on the basis of the cell culture-related data, and a program for controlling the culture operation of the cells for the each canister 16 and for the each culture cassette 17 on the basis of the cell culture-related data.

The cell culture-related data in this specification is at least one of the identification codes which are readable by, for example, a barcode reader such as individual IDs of the cells, the culture medium, the inducer, the culture bag 18, the large tray 45, the culture medium bag 67, the culture medium cassette 20, the inducer stimulation vessel 65, the cell inoculation cassette 19, the cell collecting bag 72 and the operator, or individual addresses of the incubator 11 and the canister 16, culture environment data detected by the respective sensors in the incubator 11, the canister 16 and the culture cassette 17 (the temperature sensor 24, the door sensor 35, the culture medium cassette sensor 75 the weight meter 43, etc.) and indicating the operating state of the respective pieces of equipment (the first pump 48, the second pump 49, the blast fan 34, the operating motor 81, etc.), and the image data of the cells acquired by the image processing computer 14 (the image data from the CCD camera 88, the image data acquired after having applied with processing such as binarization to the images, the evaluation parameter calculated from the image data, etc.).

Therefore, the operation control panel 13 accumulates and collects the cell culture-related data at predetermined time intervals (every minute, for example) for the each canister 16 or the each culture cassette 17 in the incubator 11 on the basis of the above-described program. Accordingly, the culture log relating to the cells cultured by the arbitrary canister 16 and the culture cassette 17 in the incubator 11 is acquired automatically, not by the operator. Likewise, the operation control panel 13 observes the culture state of the cells on the basis of the culture-related data for the each canister 16 and the each culture cassette 17 in the incubator 11 to monitor whether there is a trouble or not. Likewise, the operation control panel 13 also controls the various culture operations such as replacement of the culture medium cassette 20 (change of the culture medium), replacement by the dummy cassette 70, and replacement by the cell collecting bag 72 for the each canister 16 and the each culture cassette 17 in the incubator 11, and prompts the operator to carry out these operations. With this control, the log is automatically recorded and stored, and occurrence of intentional alteration or erroneous recording is prevented.

The monitoring computer 15 receives the cell culture-related data, the culture log data, data relating to whether there is a trouble or not, and data relating to the culture operation of the each canister 16 and the each culture cassette 17 in the incubator 11 stored in the operation control panel 13 from the operation control panel 13 and store the same, and make the data available for display (inspection) on the monitor. Accordingly, the operator is able to observe, monitor and control the cell culture carried out in the incubator 11 in a monitor room 95 other than the culture room 94 in which the incubator 11 is installed. With this control, the log is automatically recorded and maintained, and occurrence of intentional alteration or erroneous recording is prevented.

Figure 18:
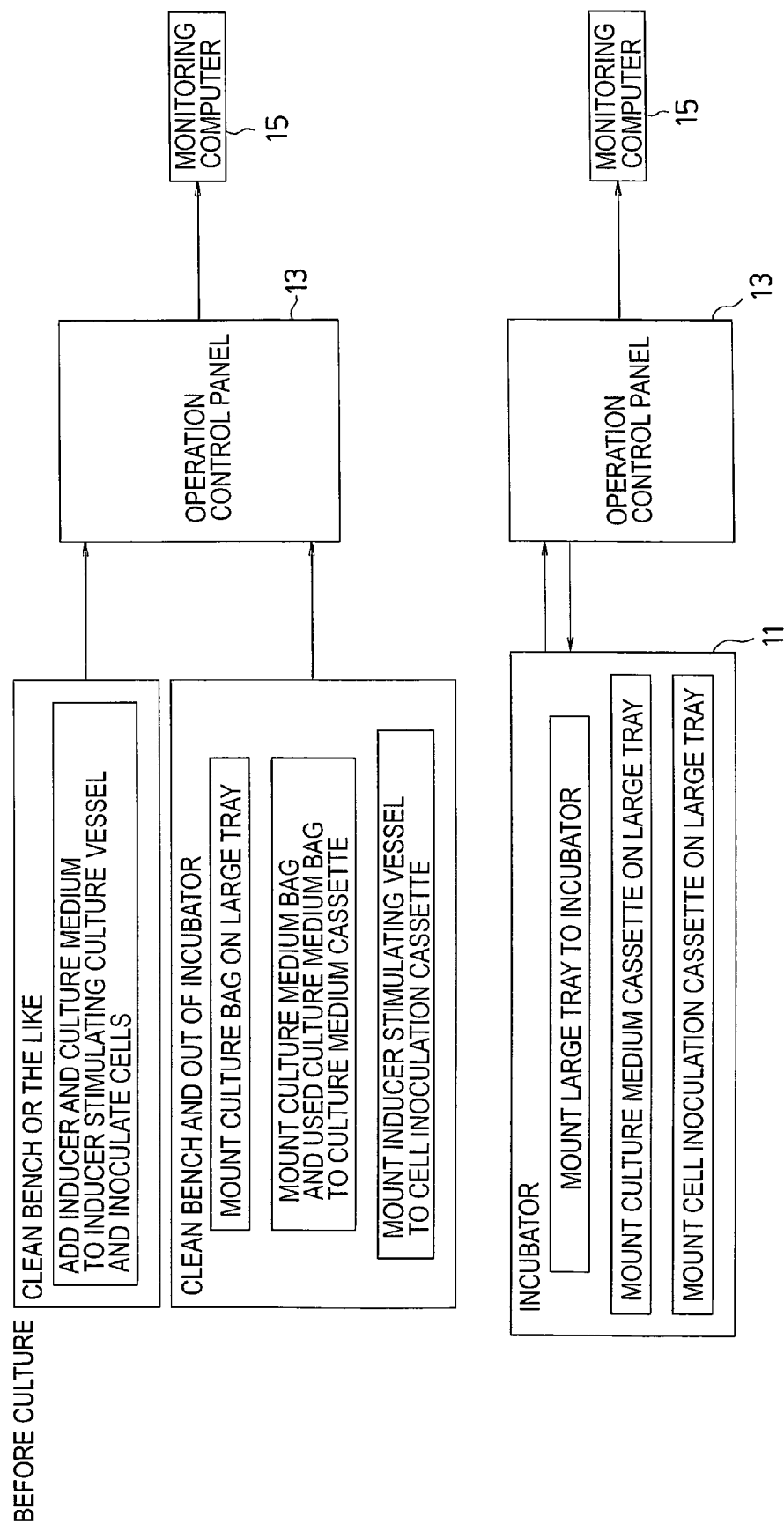
FIG. 18 is a drawing showing a flow of cell culture-related data before the cell culture in a cell culture system in FIG. 1.
Figure 19:
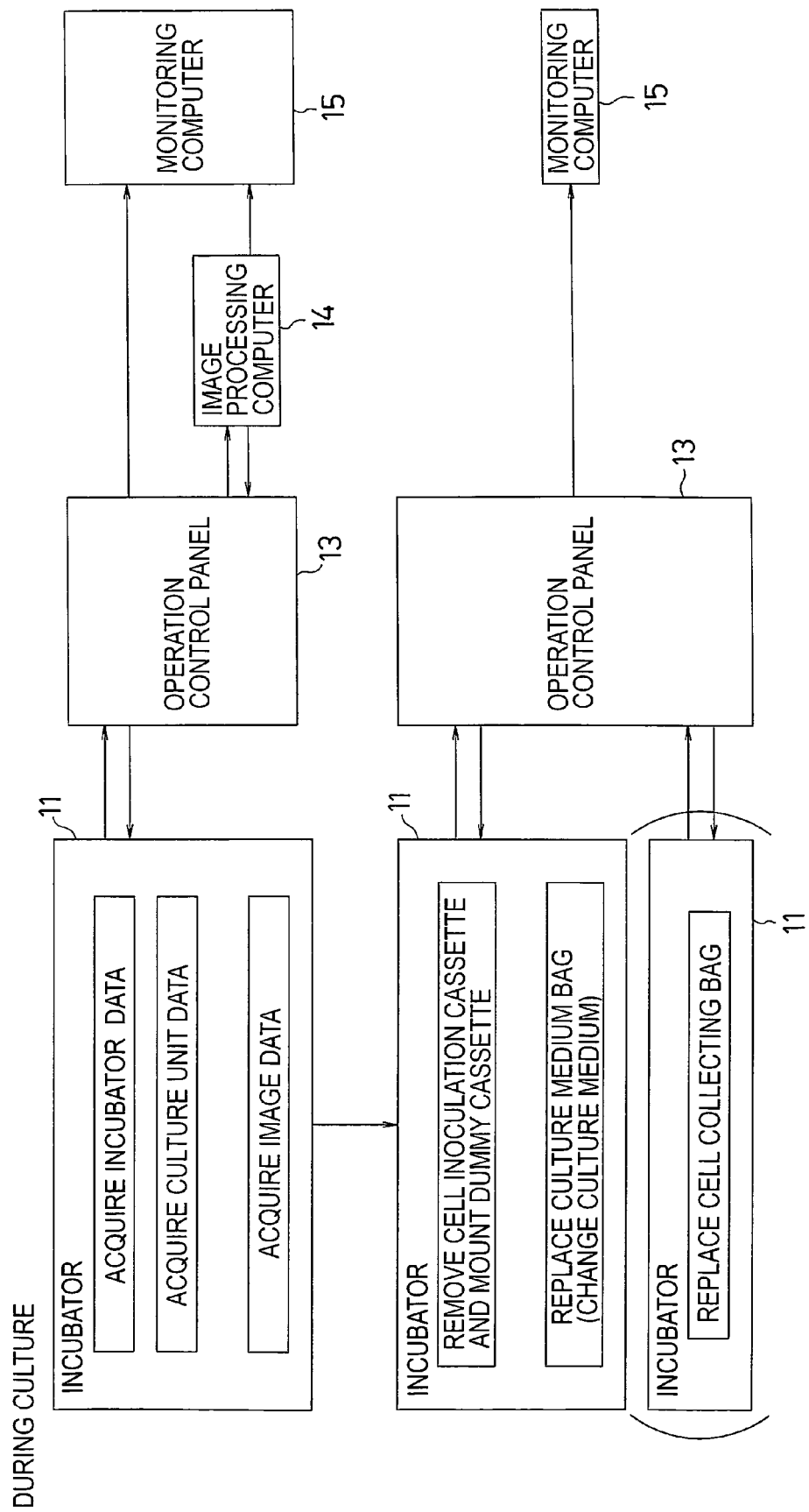
FIG. 19 is a drawing showing the flow of the cell culture-related data during the cell culture in the cell culture system in FIG. 1.

Referring now to FIG. 18 to FIG. 20, acquisition of the cell culture-related data before the cell culture, during the cell culture and after the cell culture will be described.

As shown in FIG. 18, when adding the inducer and the culture medium to the inducer stimulation vessel 65 to inoculate cells in a clean bench or the like before the cell culture, the operation control panel 13 acquires the ID of the inducer stimulation vessel 65, the IDs allocated to the storage vessels for the inducer and the culture medium, the ID of sample cells and the operator's ID together with the date and time of operation using the barcode reader and transmits the same to the monitoring computer 15. When mounting the inducer stimulation vessel 65 to the cell inoculation cassette 19, the operation control panel 13 acquires the ID of the inducer stimulation vessel 65, the ID of the cell inoculation cassette 19 and the operator's ID together with the date and time of operation using the barcode reader, and transmits the same to the monitoring computer 15. When mounting the culture bag 18 to the large tray 45, the operation control panel 13 acquires the ID of the culture bag 18, the ID of the large tray 45 and the operator's ID together with the date and time of operation using the barcode reader, and transmits to the monitoring computer 15. When mounting the culture medium bag 67 and the used culture medium bag 68 to the culture medium cassette 20, the operation control panel 13 acquires the ID of the culture medium bag 67, the ID of the culture medium cassette 20 and the operator's ID together with the date and time of operation, and transmits the same to the monitoring computer 15 using the barcode reader.

Likewise, when carrying the large tray 45 into the canister 16 in the incubator 11 before the cell culture, the operation control panel 13 acquires the addresses of the incubator 11 and the canister 16, the ID of the large tray 45 and the operator's ID together with the date and time of operation using the barcode reader, and transmits the same to the monitoring computer 15. When mounting the culture medium cassette 20 to the large tray 45 stored in the canister 16 in the incubator 11 before the cell culture, the operation control panel 13 acquires the addresses of the incubator 11 and the canister 16, the ID of the culture medium cassette 20 and the operator's ID together with the date and time of operation using the barcode reader, and transmits the same to the monitoring computer 15. When mounting the cell inoculation cassette 19 to the large tray 45 stored in the canister 16 in the incubator 11 before the cell culture, the operation control panel 13 acquires the addresses of the incubator 11 and the canister 16, the ID of the cell inoculation cassette 19 and the operator's ID together with the date and time of operation using the barcode reader, and transmits the same to the monitoring computer 15.

As shown in FIG. 19, during the cell culture, the operation control panel 13 acquires the date and time as well as the address of the incubator 11 together with the operating/stopping state of the incubator 11 and measured data from the various sensors (temperature sensor 24, etc.) in the incubator 11, and transmits the same to the monitoring computer 15. During the cell culture, the operation control panel 13 acquires the date and time and the address of the canister 16 together with the operating/stopping state of the incubator 11, the canister 16 and the culture cassette 17 in the canister 16, the operating/stopping states of various equipment (the blast fan 34, the first pump 48, etc.) in the canister 16 and the culture cassette 17, and measured data of the various sensors (the temperature sensor 37, the weight meter 43, etc.) of the canister 16 and the culture cassette 17, and transmits the same to the monitoring computer 15. Also, during the cell culture, the operation control panel 13 acquires the date and time and the address of the canister 16, the image data of the cells shot by the CCD camera 88, the processed data acquired by processing such as binarization the image data and the evaluation parameter from the image processing computer 14, and transmits the same to the monitoring computer 15. At this time, the operation control panel 13 outputs the control signal for controlling the various equipment to the incubator 11, the canister 16 and the culture cassette 17 as described above.

When the cell inoculation cassette 19 has no more cell left therein during the cell culture and hence is replaced by the dummy cassette 70, the operation control panel 13 acquires the addresses of the corresponding incubator 11 and the canister 16, the ID of the large tray 45, the ID of the cell inoculation cassette 19 and the operator's ID together with the date and time of operation, and is transmitted to the monitoring computer 15. When the culture medium bag 67 in the culture medium cassette 20 is emptied during the cell culture and hence is replaced by a new culture medium cassette 20 having the culture medium bag 67 filled with the culture medium (when replacing the culture medium), the operation control panel 13 acquires the addresses of the corresponding incubator 11 and the canister 16, the ID of the culture medium cassette 20, the ID of the culture medium bag 67 and the operator's ID together with the date and time of operation, and transmits the same to the monitoring computer 15.

Furthermore, when the cells are collected not in the culture bag 18, but in the cell collecting bag 72, the cells are condensed in the culture bag 18 during the cell culture, and the operation control panel 13 acquires the addresses of the corresponding incubator 11 and the canister 16, the ID of the large tray 45, the ID of the culture medium cassette 20, the ID of the cell collecting bag 72 and the operator's ID together with the date and time of operation and transmits the same to the monitoring computer 15 when the used culture medium bag 68 in the culture medium cassette 20 is replaced by the cell collecting bag 72. At the time of the replacement by the dummy cassette 70, the replacement of the culture medium cassette 20 (change of the culture medium), and replacement by the cell collecting bag 72, the operation control panel 13 activates the door lock mechanism 39 in the canister 16 of the corresponding incubator 11 to release the door lock, and confirms the replacement by the dummy cassette 70, the replacement of the culture medium cassette 20 (displacement of the culture medium), and the replacement by the cell collecting bag 72 by the signals from the cell inoculation cassette sensor 74 or the culture medium cassette sensor 75.

Figure 20A:
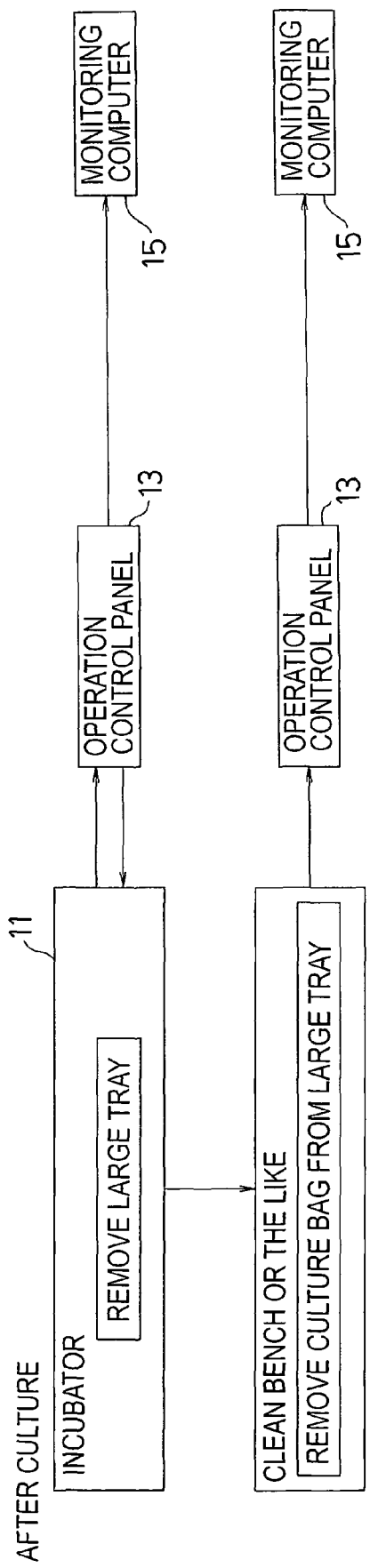
FIG. 20 is a drawing showing the flow of the cell culture-related data after the cell culture in the cell culture system in FIG. 1.

As shown in FIG. 20A, when collecting the cells in the culture bag 18 having completed the cell culture, the operation control panel 13 acquires the addresses of the corresponding incubator 11 and the canister 16, the ID of the large tray 45 and the operator's ID together with the date and time of operation when the large tray 45 is removed, and transmits the same to the monitoring computer 15. Subsequently, when taking the culture bag 18 out from the large tray 45 in the clean bench or the like, the operation control panel 13 acquires the ID of the large tray 45, the ID of the culture bag 18 and the operator's ID together with the date and time of operation, and transmits the same to the monitoring computer 15. When removing the large tray 45 and the culture bag 18, the operation control panel 13 activates the door lock mechanism 39 in the canister 16 of the corresponding incubator 11 to release the door lock.

Figure 20B:
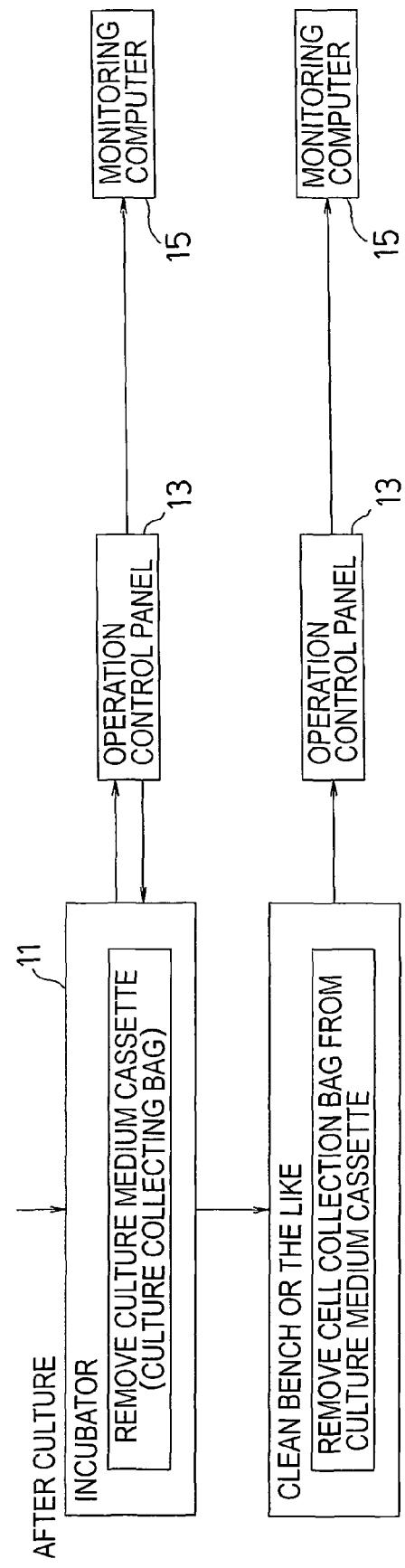

As shown in FIG. 20B, when the cells are collected in the cell collecting bag 72 after having completed the cell culture, the operation control panel 13 acquires the addresses of the corresponding incubator 11 and the canister 16, the ID of the culture medium cassette 20, the ID of the cell collecting bag 72 and the operator's ID together with the date and time of operation when removing the culture medium cassette 20 provided with the cell collecting bag 72, and transmits the same to the monitoring computer 15. Subsequently, when removing the cell collecting bag 72 from the culture medium cassette 20 in the clean bench or the like, the operation control panel 13 acquires the ID of the culture medium cassette 20, the ID of the cell collecting bag 72 and the operator's ID together with the date and time of operation, and transmits the same to the monitoring computer 15.

Referring now to process drawings from FIG. 8 to FIG. 11 and flowcharts shown in FIG. 12 to FIG. 17, a process followed by the operation control panel 13 and the image processing computer 14 to carry out the above-described program to culture the cells will be described. In this cell culture process, the operation control panel 13 and the image processing computer 14 set and control the culture environment independently for the each canister 16 in the incubator 11, and culture cells in the culture cassette 17 stored in the each canister 16.

Figure 11A:
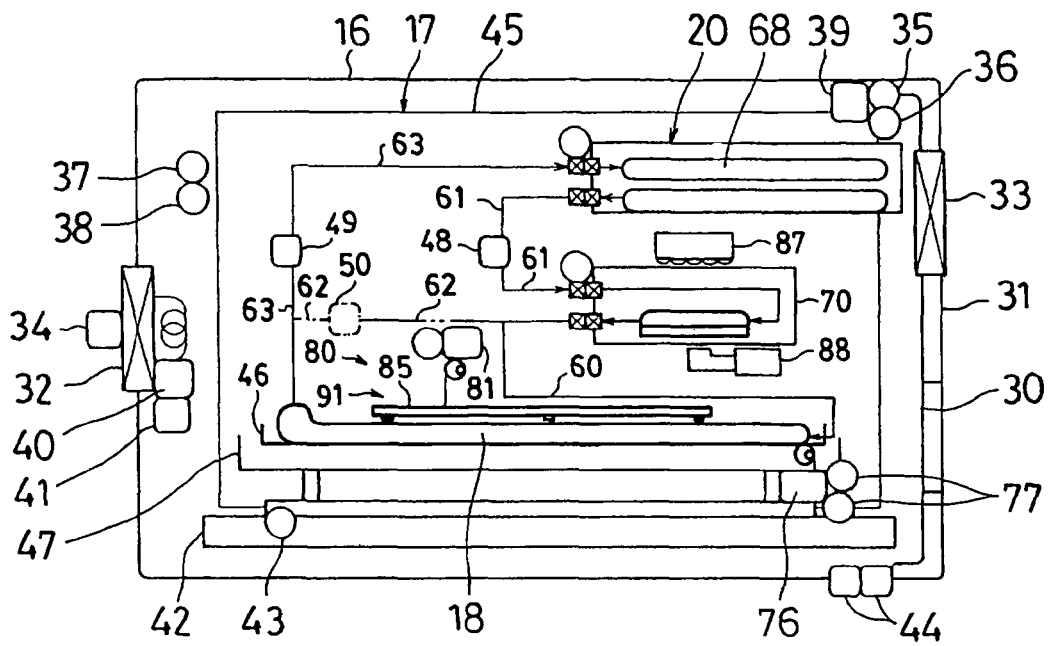
FIG. 11 is a procedure of the culture in the culture unit shown in FIG. 5 and is a process drawing following FIG. 10.
Figure 11B:
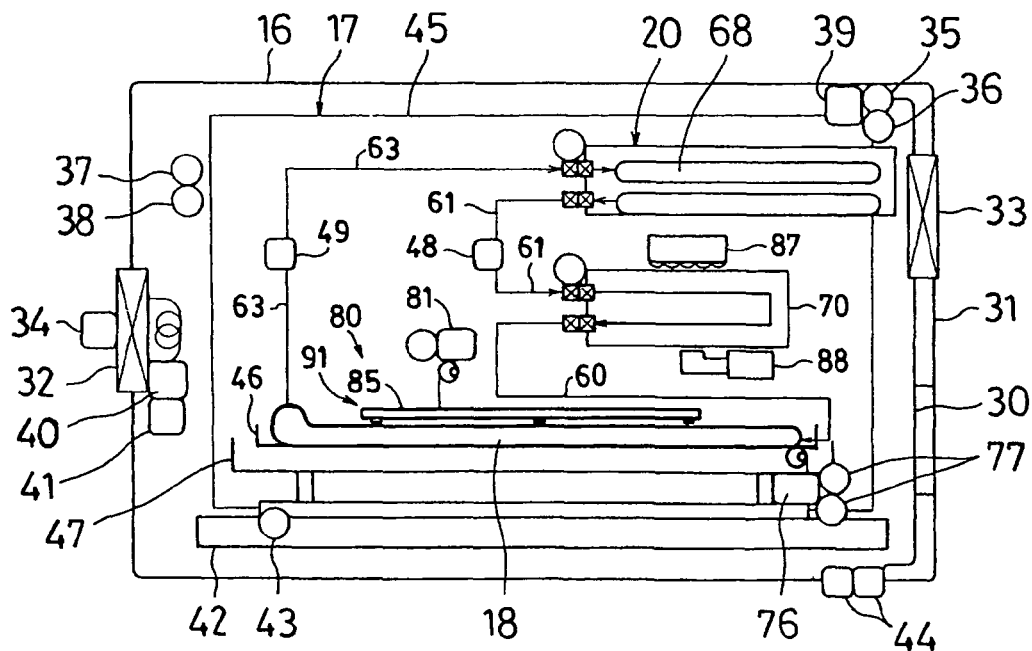
Figure 12:
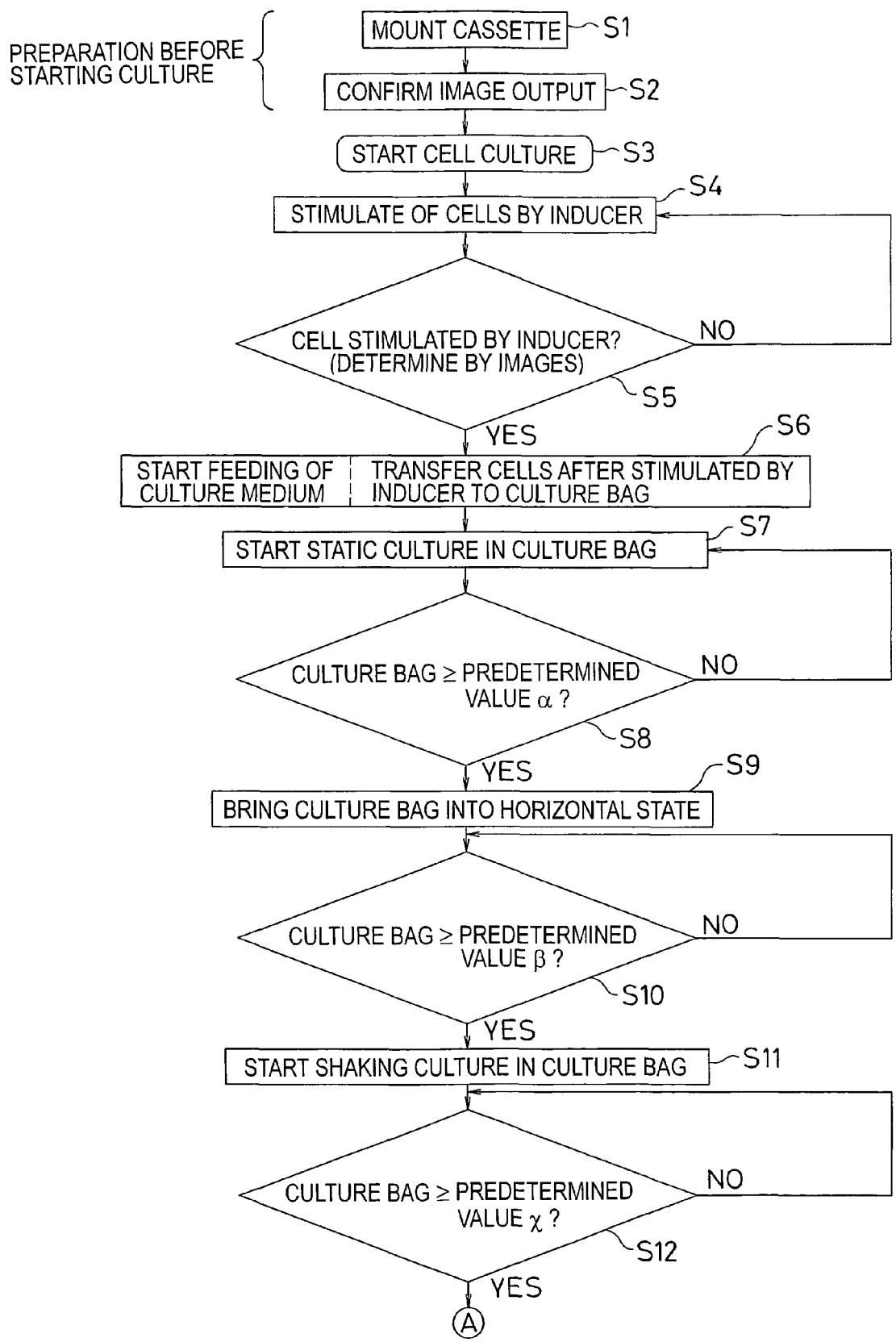
FIG. 12 is a flowchart showing process steps in an inducer stimulating intermittent perfusion culture process in the culture unit in FIG. 5.

FIG. 8 to FIG. 13 show an inducer stimulating intermittent perfusion culture process carried out in the case of collecting the cells in the culture bag 18. As shown in FIG. 8A and FIG. 12, the operator places the empty culture bag 18 on the culture bag tray 47 interposing the platform 46 between the culture bag 18 and the culture bag tray 47, mounts the culture bag tray 47 to the large tray 45, and connects the culture bag 18 to the first pump 48, the second pump 49 and the third pump 50.

Figure 8A:
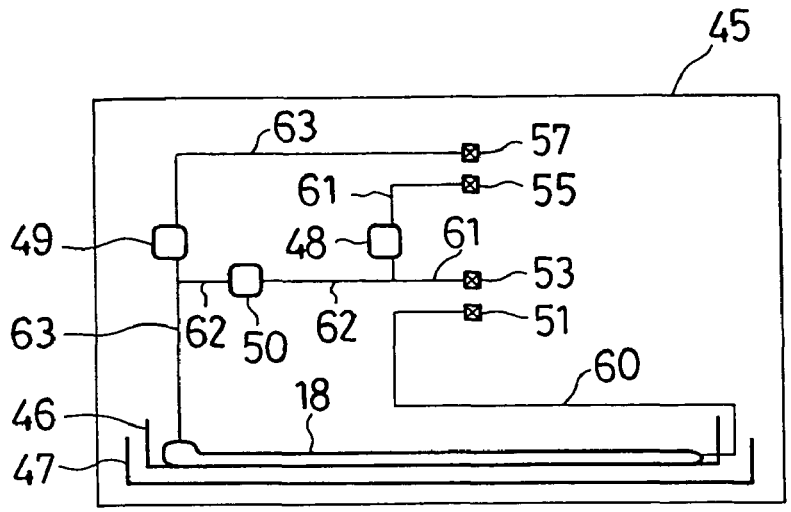
FIG. 8 is a process drawing showing a procedure of the culture in the culture unit shown in FIG. 5.
Figure 8B:
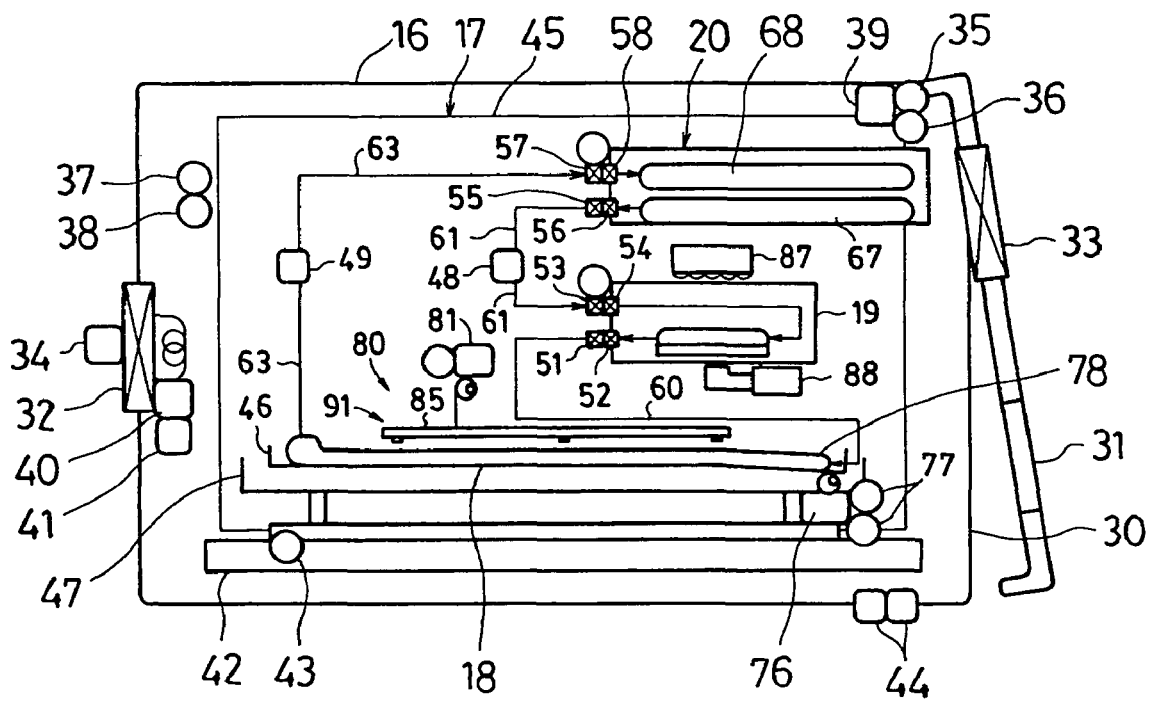

Subsequently, the operator puts the large tray 45 into the single canister 16 whose indication lamp 44 is illuminated, for example, in green, in the incubator 11, and makes the stage 42 to support the same. Then, the operator immobilizes the inducer in the inducer stimulation vessel 65 in the clean bench or the like, puts the culture medium therein, and mounts the cell inoculation cassette 19 to which cells are inoculated to the large tray 45 in the canister 16, as shown in FIG. 8B. Subsequently, the operator mounts the culture medium cassette 20 having the culture medium bag 67 to which the culture medium is put in the clean bench or the like to the large tray 45 in the canister 16 (S1 in FIG. 12).

Subsequently, the operator confirms the output of the image from the CCD camera 88 in the canister 16 in which the culture cassette 17 having the culture bag 18, the cell inoculation cassette 19 and the culture medium cassette 20 mounted to the large tray 45 is stored (S2 in FIG. 12). Before or after the confirmation of the image output, the operator activates the inclined motor 76 of the canister 16 to move the elevating unit of the platform 46 downward and form the liquid reservoir 78 in the culture bag 18. The operator then measures the weight of the empty culture bag 18 by the weight meter 43 of the canister 16.

Figure 9A:
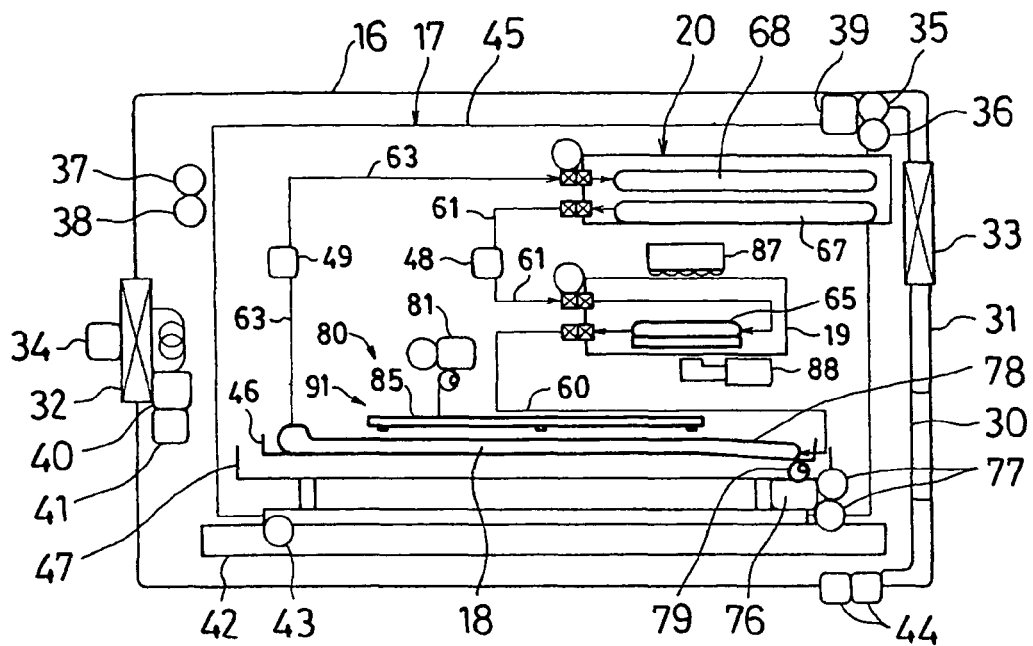
FIG. 9 is a procedure of the culture in the culture unit shown in FIG. 5 and is a process drawing following FIG. 8.

Then, as shown in FIG. 9A, the operator closes the canister door 31 and starts the cell culture in the corresponding canister 16 (S3 in FIG. 12). Accordingly, in the inducer stimulation vessel 65 in the cell inoculation cassette 19, the cells are stimulated by the inducer for proliferation (S4 in FIG. 12). The CCD camera 88 of the corresponding canister 16 takes images of the cells in the inducer stimulation vessel 65 in the cell inoculation cassette 19 at predetermined time intervals (every six hours, for example), and the image processing computer 14 calculates the evaluation parameter of the cell culture from the picked-up images. In addition, the image processing computer 14 calculates a lag time from the evaluation parameter to determine whether there is a capability that the cells proliferate by the stimulation from the inducer or not, and further calculates the minimum doubling time to determine the proliferation ability of the cells (S5 in FIG. 12).

Figure 9B:
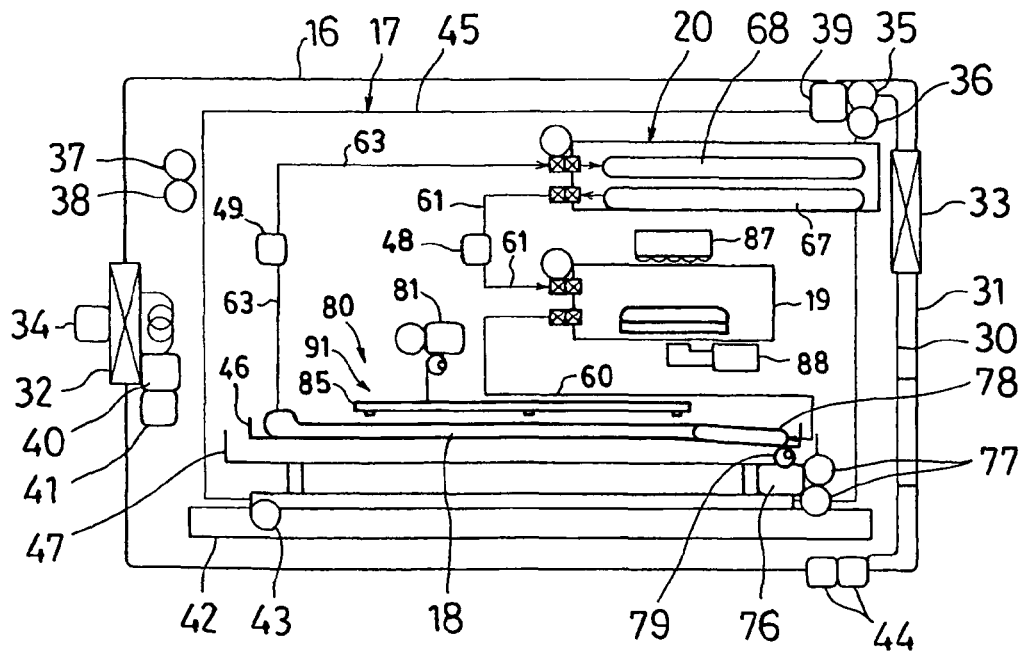

When the operation control panel 13 receives a signal determining that the proliferation capability cannot be confirmed even a predetermined time length (72 hours, for example) has elapsed since the cells are stimulated by the inducer in the inducer stimulation vessel 65 in the cell inoculation cassette 19 from the image processing computer 14, the operation control panel 13 displays so. When the operation control panel 13 receives a signal determining that the cells in the inducer stimulation vessel 65 in the cell inoculation cassette 19 has a probability to proliferate from the image processing computer 14, the operation control panel 13 decides the timing to transfer the cells to the culture bag 18 or the feeding velocity of the culture medium into the culture bag 18 on the basis of the proliferation ability of the cells. The operation control panel 13 activates the first pump 48 on the basis of these decision and, as shown in FIG. 9B, to feed the culture medium in the culture medium bag 67 of the culture medium cassette 20 to the cell inoculation cassette 19, transfers the cells in the inducer stimulation vessel 65 in the cell inoculation cassette 19 to the culture bag 18, and feeds the culture medium in the culture medium bag 67 to the culture bag 18 (S6 in FIG. 12).

Figure 10A:
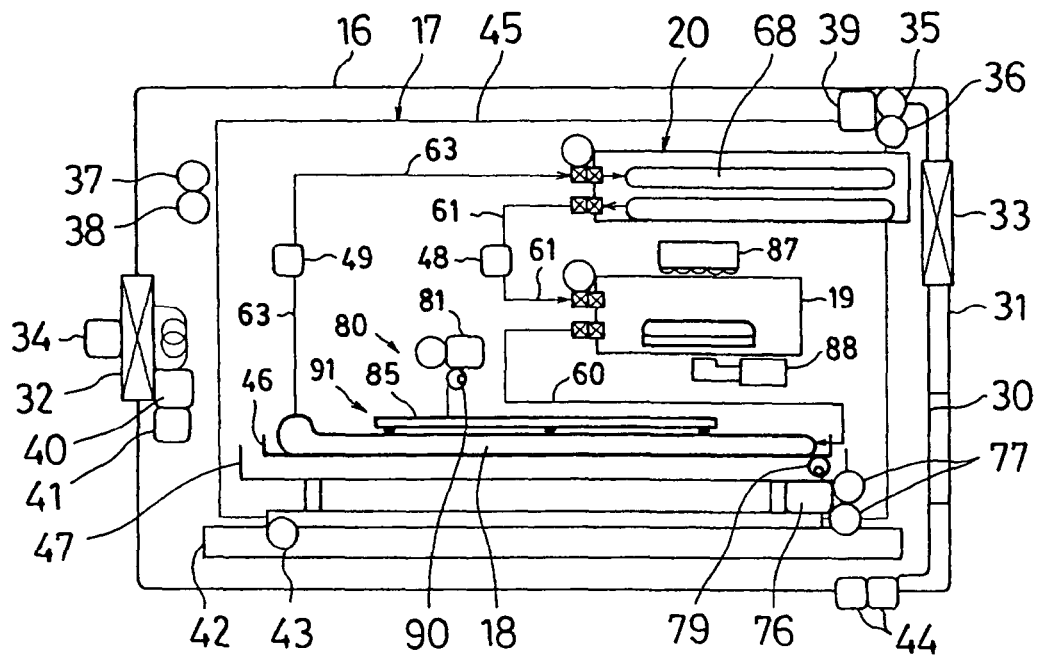
FIG. 10 is a procedure of the culture in the culture unit shown in FIG. 5 and is a process drawing following FIG. 9.

By the operation of the first pump 48, the static culture of the cells in the liquid reservoir 78 of the culture bag 18 is started (S7 in FIG. 12). The operation control panel 13 follows the program to carry out the feeding culture while feeding the culture medium, and to determine whether the weight of the culture suspension in the culture bag 18 measured by the weight meter 43 is increased to a level at least equal to a predetermined value α or not (S8 in FIG. 12). The operation control panel 13 activates the inclined motor 76 at a timing when the predetermined value α is reached, moves the elevating portion of the platform 46 upward via the cam mechanism 79 and, as shown in FIG. 10A, brings the culture bag 18 into a horizontal state to eliminate the liquid reservoir 78 (S9 in FIG. 12).

Figure 10B:
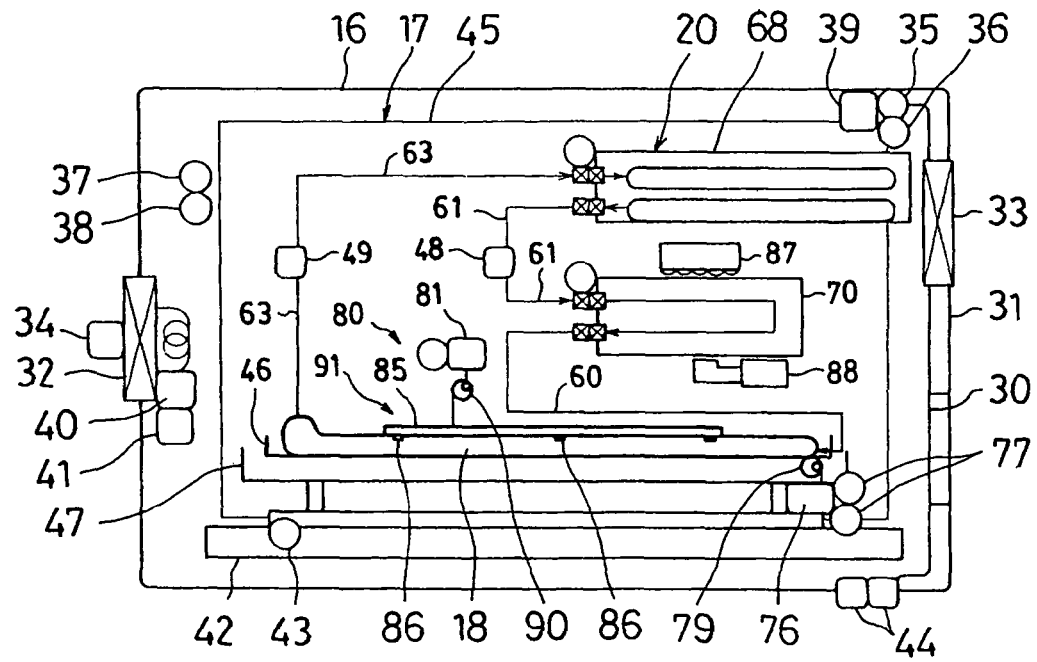

Then, the operation control panel 13 determines whether the weight of the culture suspension in the culture bag 18 measured by the weight meter 43 is increased to a level at least equal to a predetermined value β (S10 in FIG. 12) or not, and activates the operating motor 81 at a timing when the predetermined value β is reached. Accordingly, as shown in FIG. 10B, the shaking device 80 is activated, and the shaking culture in which the operating plate 85 in the shaking mechanism 91 of the shaking device 80 presses the culture bag 18 repeatedly is started (S11 in FIG. 12). The operation control panel 13 continues to determine whether the weight of the culture suspension in the culture bag 18 measured by the weight meter 43 is increased to a level at least equal to a predetermined value χ (S12 in FIG. 12) or not. When the predetermined value χ is reached, the first pump 48 is stopped, feeding of the culture medium from the culture medium bag 67 in the culture medium cassette 20 to the culture bag 18 is stopped, and the operating motor 81 is stopped to stop the shaking culture in the culture bag 18 (S13 in FIG. 13).

Figure 13:
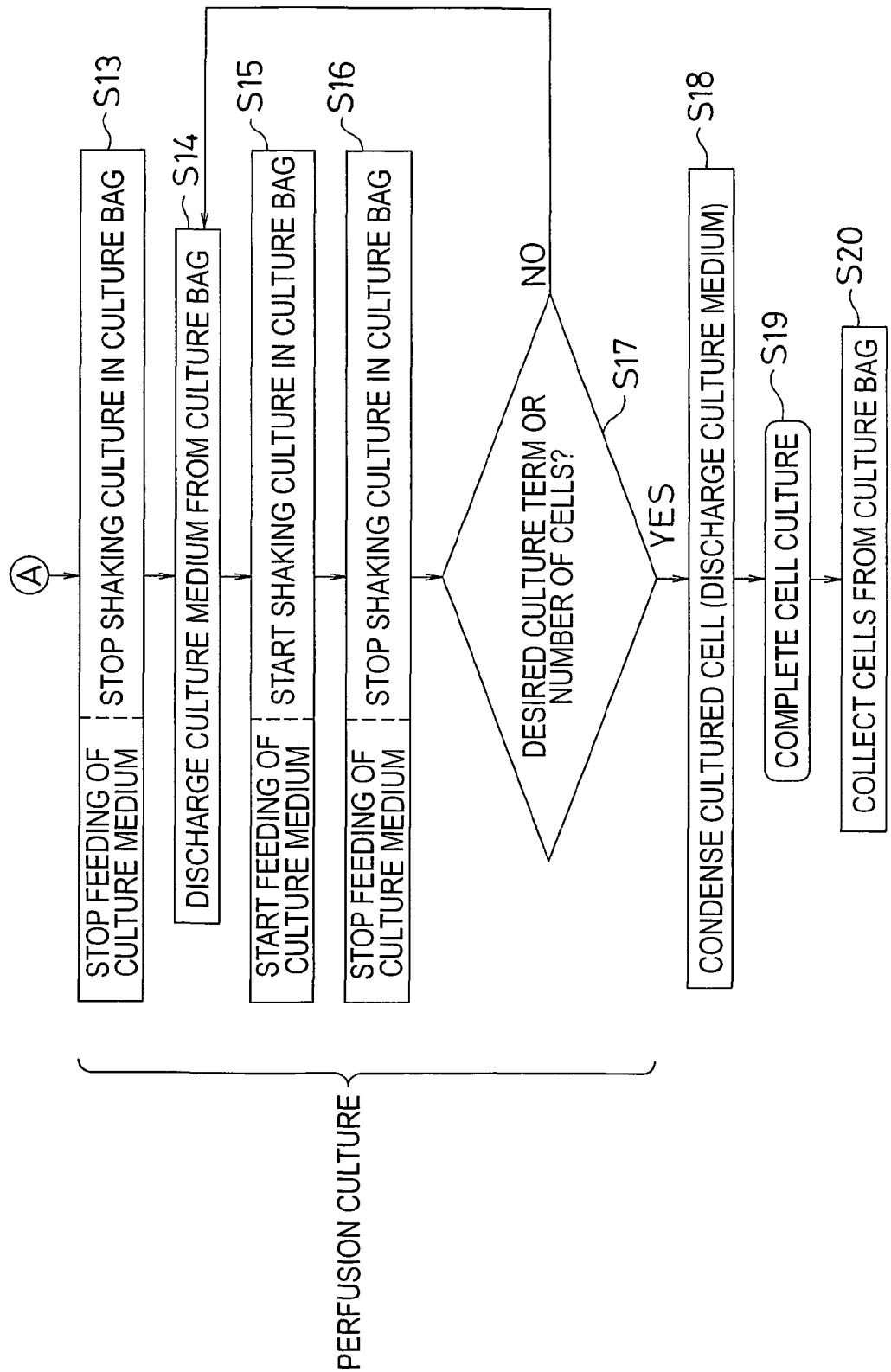
FIG. 13 is a flowchart showing steps following the process steps in FIG. 12.

The operation control panel 13 activates the second pump 49 after the cells are settled in the culture bag 18 to discharge the used culture medium in the culture bag 18 (supernatant in the culture bag 18) to the used culture medium bag 68 in the culture medium cassette 20 as shown in FIG. 11A (S14 in FIG. 13). Then, the operation control panel 13 activates the first pump 48 and feeds the culture medium from the culture medium bag 67 in the culture medium cassette 20 to the culture bag 18, and activates the operating motor 81 to carry out the shaking culture in the culture bag 18 by the shaking device 80 (S15 in FIG. 13). After having elapsed a predetermined time length, the operation control panel 13 stops the first pump 48, stops the feeding of the culture medium from the culture medium bag 67 in the culture medium cassette 20 to the culture bag 18, and stops the operating motor 81 to stop the shaking culture in the culture bag 18 (S16 in FIG. 13).

The operation control panel 13 determines whether the desired culture term depending on the date and time of usage of the cells to proliferate is reached or not, or the image processing computer 14 determines whether the cells in the culture bag 18 reaches the desired number of cells or not (S17 in FIG. 13). When determining whether the cells in the culture bag 18 reaches the desired number of cells or not, the operation control panel 13 activates the third pump 50 (FIG. 11A), transfers a part of the cells in the culture bag 18 to the cell inoculation cassette 19 or the dummy cassette 70 (the dummy cassette 70 in most cases), and makes the CCD camera 88 to take an image of the cells. The image processing computer 14 processes the image of the cells, determines whether the number of cells is at least equal to a specified value or not, and transmits the same to the operation control panel 13. When the culture term or the number of cells is not reached, the operation control panel 13 repeats the processing operation from Step S14 to Step S17.

The Steps S13 to S17 are steps for the intermittent perfusion culture in which discharge of the used culture medium in the culture bag 18 and supply (feed) of new culture medium to the culture bag 18 are carried out alternately.

In Steps S9 to S17, the presence or absence of the cells in the inducer stimulation vessel 65 in the cell inoculation cassette 19 is confirmed by the CCD camera 88 and, when there is no cell in the inducer stimulation vessel 65, the operation control panel 13 prompts the operator to replace the cell inoculation cassette 19 by the dummy cassette 70 so as to prevent the inducer from flowing from the inducer stimulation vessel 65 into the culture bag 18. When replacing the cell inoculation cassette 19 by the dummy cassette 70, the operation control panel 13 stops feeding of the culture medium from the culture medium cassette 20 to the culture bag 18 and the shaking culture by the shaking device 80 temporarily until the replacement of the cell inoculation cassette 19 by the dummy cassette 70 is completed.

Then, in Steps S9 to S17, when the operation control panel 13 determines that there is no more culture medium in the culture medium bag 67 in the culture medium cassette 20 from the measured value of the weight meter 43, the operation control panel 13 prompts the operator to replace the culture medium cassette 20 by a new culture medium cassette 20. When replacing the culture medium cassette 20 by the new culture medium cassette 20 as well, the operation control panel 13 stops feeding of the culture medium from the culture medium cassette 20 to the culture bag 18 and the shaking culture by the shaking device 80 temporarily until the replacement of the culture medium cassette 20 is completed.

At the time point when the desired culture term is reached or when the desired number of cells is reached in Step S17, the operation control panel 13 stops shaking. When the cells are settled, the operation control panel 13 activates the second pump 49 as shown in FIG. 11B, discharges the used culture medium in the culture bag 18 to the used culture medium bag 68 of the culture medium cassette 20 and condenses the cells until the culture suspension in the culture bag 18 is reduced to about ½ to ⅓ on the basis of the measured value by the weight meter 43 (S18 in FIG. 12).

The operation control panel 13 then stops the second pump 49 to complete the cell culture (S19 in FIG. 12). After having completed the culture, the cells in the culture bag 18 are transferred to a vessel for the centrifuge in the clean bench or the like by the operator, and then the cells are collected by the centrifugation (S20 in FIG. 12).

Figure 14:
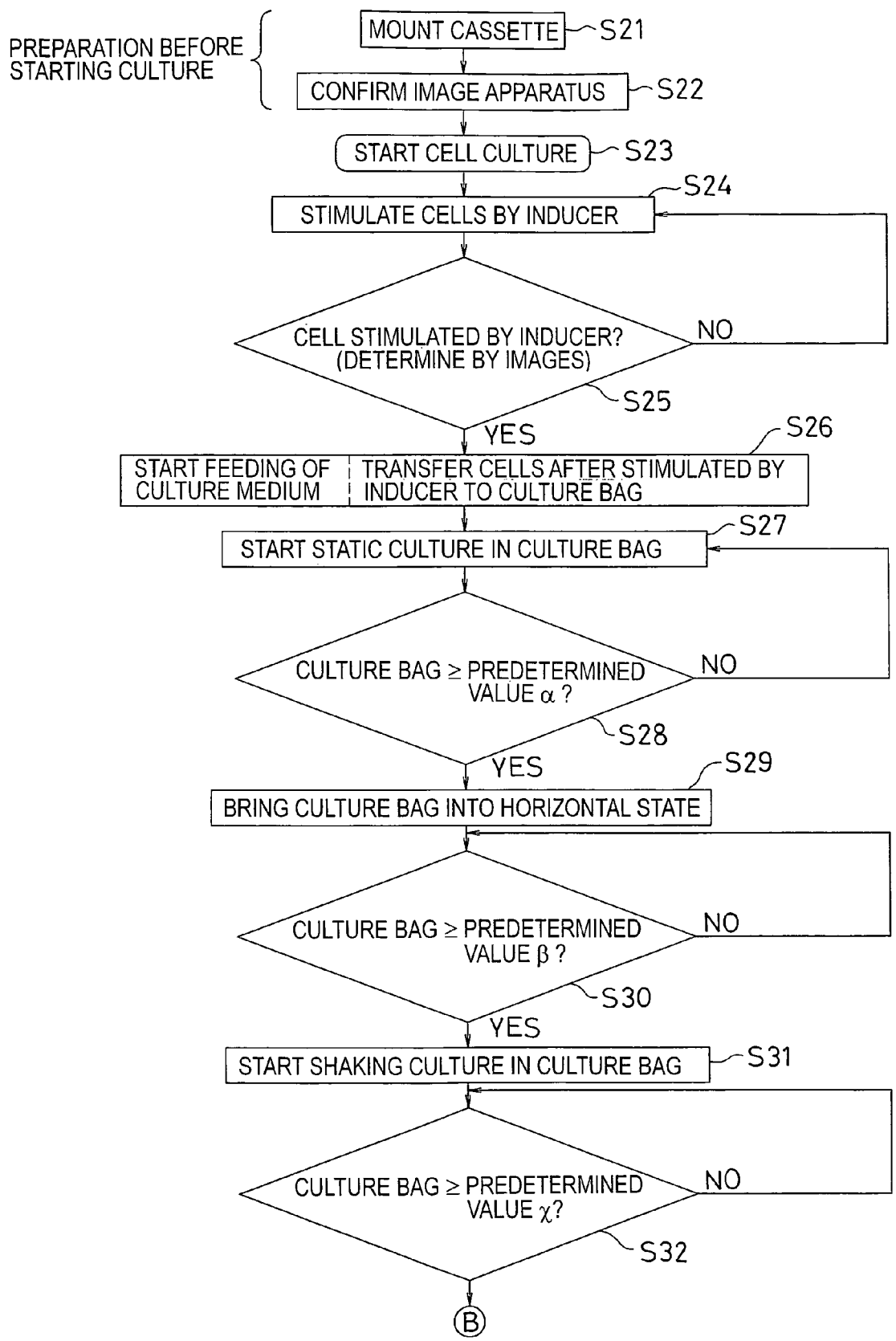
FIG. 14 is a flowchart showing process steps in the inducer stimulating intermittent perfusion culture process (including a cell collecting step using a cell collecting bag) in the culture unit in FIG. 5.

Subsequently, a case in which the process of collecting the cells by the cell collecting bag 72 (FIG. 5) in the inducer stimulating intermittent perfusion culture process is include will be shown in FIG. 14 and FIG. 15. Therefore, Steps S21 to S38 in the process shown in FIG. 14 and FIG. 15 are the same as Steps S1 to S18 in FIG. 12 and FIG. 13, and hence description is omitted.

Figure 15:
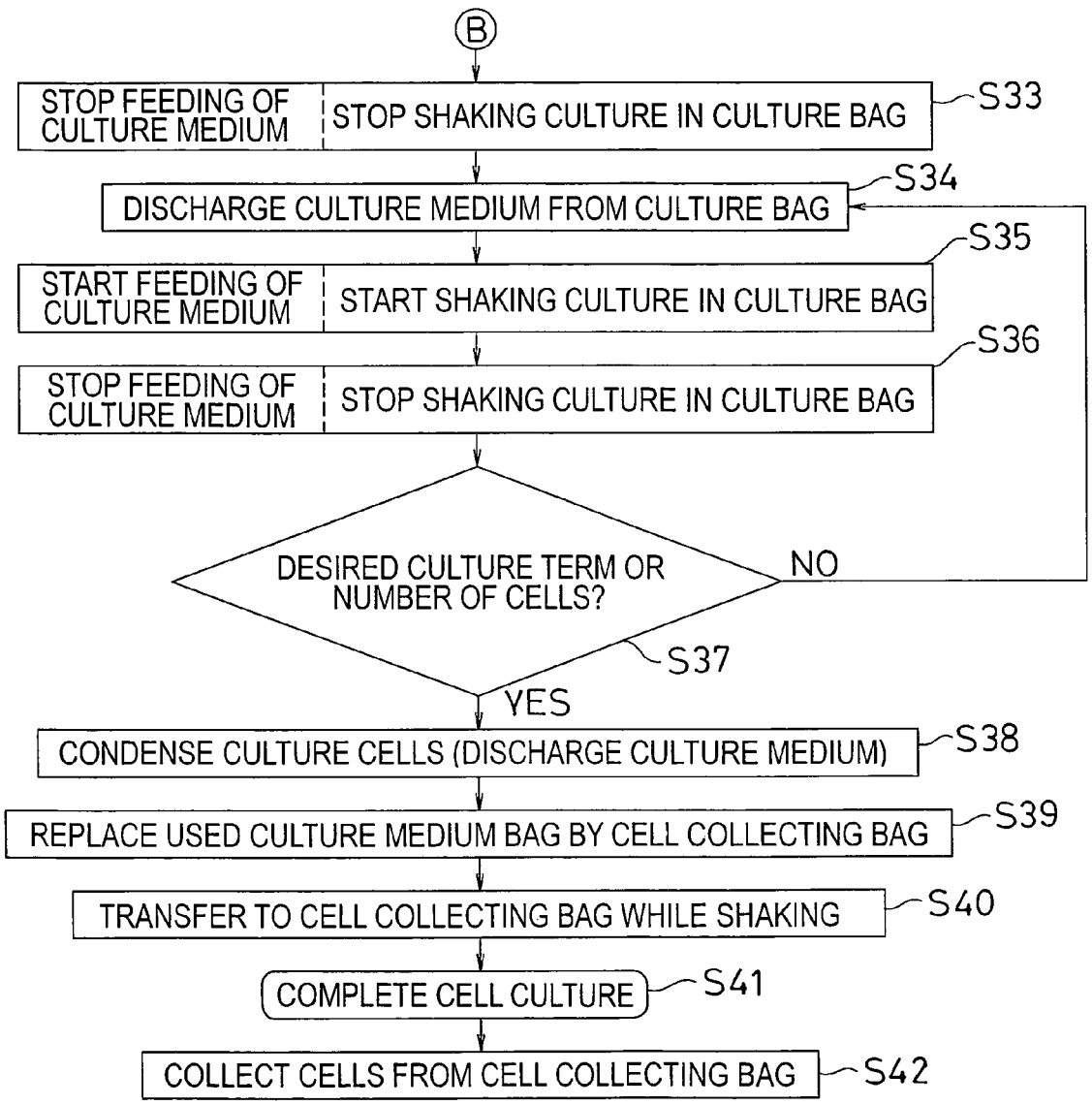
FIG. 15 is a flowchart showing steps following the process steps in FIG. 14.

In Step S38 shown in FIG. 15, after having condensed the cells in the culture bag 18 by the activation of the second pump 49, the operation control panel 13 stops the second pump 49, and prompts the operator to replace the used culture medium bag 68 in the culture medium cassette 20 by the cell collecting bag 72 (FIG. 5) (S39 in FIG. 13). The cell collecting bag 72 is a bag which may be used for the centrifugation by being mounted to the centrifuge.

After having replaced the used culture medium bag 68 in the culture medium cassette 20 by the cell collecting bag 72, the operation control panel 13 activates the second pump 49 and the operating motor 81, and transfers the cells in the culture bag 18 to the cell collecting bag 72 mounted to the culture medium cassette 20 together with the culture medium while shaking the interior of the culture bag 18 by the shaking device 80 (S40 in FIG. 15). The operation control panel 13 then stops the second pump 49 and the operating motor 81 and stops the cell culture (S41 in FIG. 15). After having completed the culture, the operator mounts the cell collecting bag 72 to the centrifuge and collects the cells by the centrifugation (S42 in FIG. 15).

Figure 16:
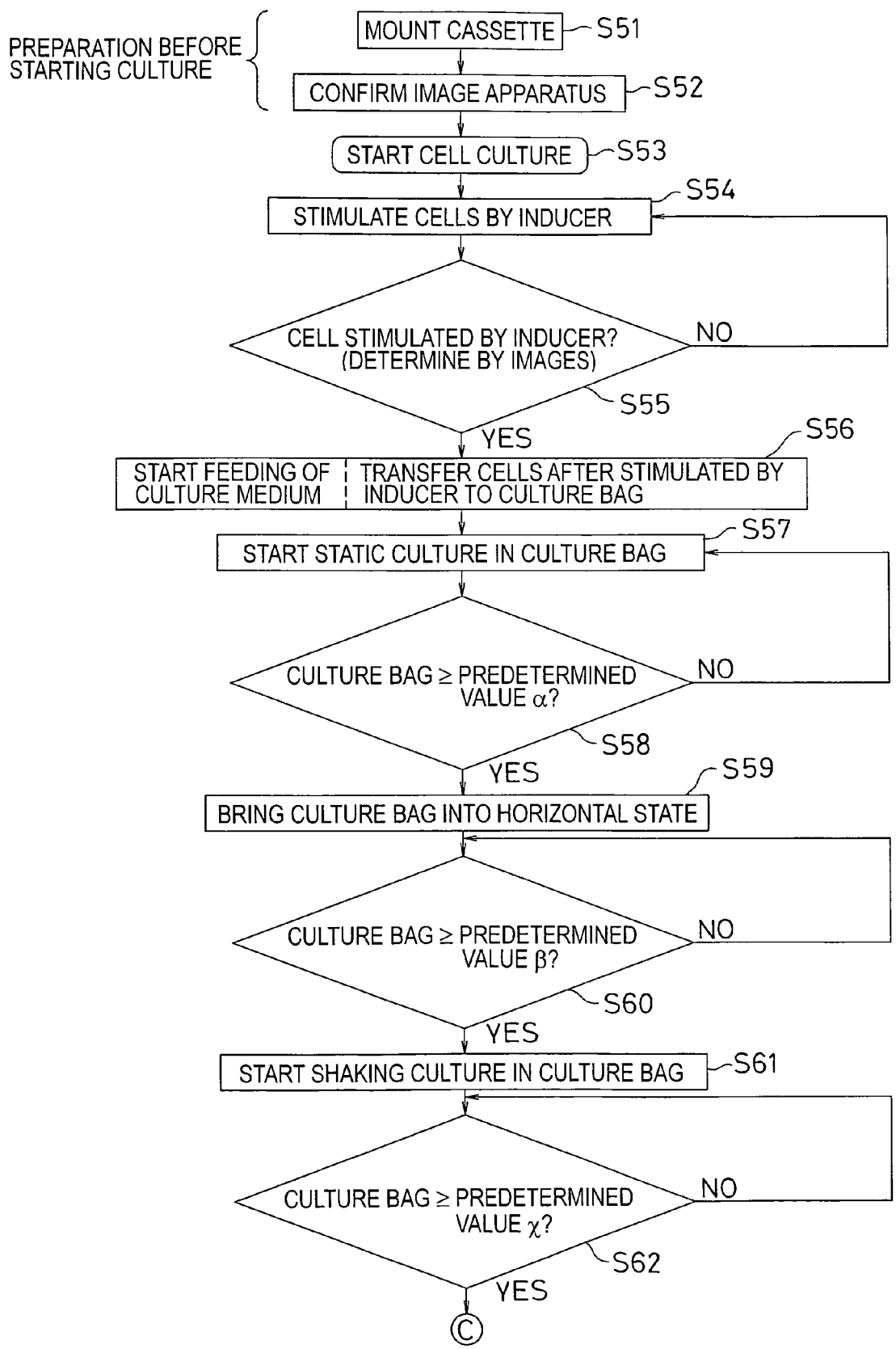
FIG. 16 is a flowchart showing process steps in an inducer stimulating consecutive perfusion culture process in the culture unit in FIG. 5.
Figure 17:
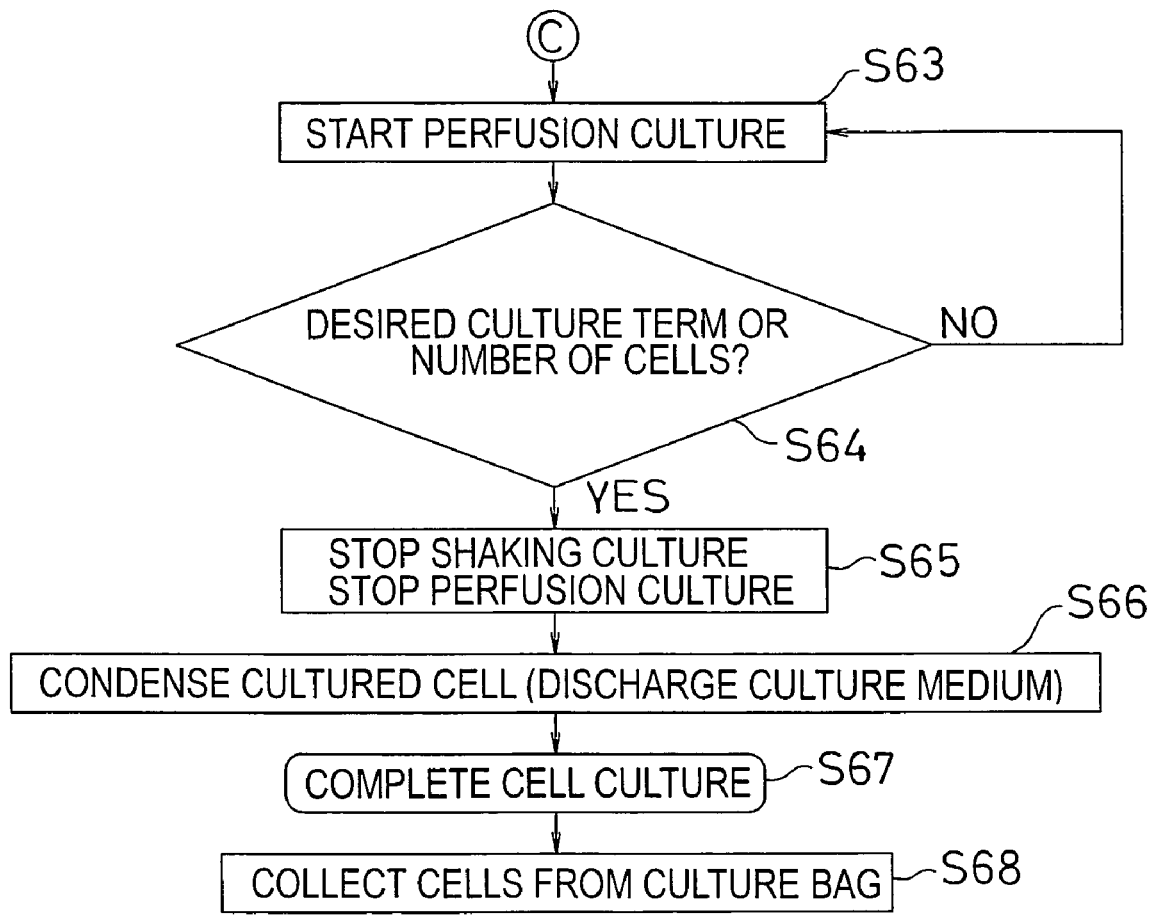
FIG. 17 is a flowchart showing steps following the process steps in FIG. 16.

Referring now to FIG. 16 and FIG. 17, the inducer stimulating consecutive perfusion culture process will be described. Steps S51 to S62 in the inducer stimulating consecutive perfusion culture process shown in FIG. 16 and FIG. 17 are the same as Steps S1 to S12 in the inducer stimulating intermittent perfusion culture process in FIG. 12 and FIG. 13, and hence description is omitted. In the inducer stimulating consecutive perfusion culture process, the filter 71 is disposed between the culture bag 18 and the second pump 49.

The operation control panel 13 activates the second pump 49 and discharges the used culture medium in the culture bag 18 to the used culture medium bag 68 in the culture medium cassette 20 at a moment when the weight of the culture suspension in the culture bag 18 is increased to a level at least equal to the predetermined value X (S62 in FIG. 16) during the shaking culture by the shaking device 80 in the culture bag 18 (S61 in FIG. 16) while feeding the culture medium from the culture medium bag 67 in the culture medium cassette 20 into the culture bag 18 (S56 in FIG. 16). Accordingly, the consecutive perfusion culture which carries out feeding of the culture medium to the culture bag 18 and discharge of the used culture medium from the culture bag 18 simultaneously is started in the culture bag 18 (S63 in FIG. 17). At this time, the cells in the culture bag 18 are prevented from flowing by the filter 71 and hence do not flow into the used culture medium bag 68. The shaking culture by the shaking device 80 is carried out simultaneously during the consecutive perfusion culture.

The operation control panel 13 determines whether the desired culture term depending on the date and time of usage of the cells to proliferate is reached or not, or the image processing computer 14 determines whether the cells in the culture bag 18 reaches the desired number of cells or not (S64 in FIG. 17). When determining whether the cells in the culture bag 18 reaches the desired number of cells or not, the operation control panel 13 activates the third pump 50, transfers a part of the cells in the culture bag 18 to the cell inoculation cassette 19 or the dummy cassette 70 (the dummy cassette 70 in most cases), and makes the CCD camera 88 to take an image of the cells. The image processing computer 14 processes the image of the cells, determines whether the number of cells is at least equal to a specified value or not, and transmits the same to the operation control panel 13. When the culture term or the number of cells as described above is not reached, the operation control panel 13 repeats the consecutive perfusion culture in Step S63.

In Steps S59 to S64, the presence or absence of the cells in the inducer stimulation vessel 65 in the cell inoculation cassette 19 is confirmed by the CCD camera 88 and, when there is no cell in the inducer stimulation vessel 65, the operation control panel 13 prompts the operator to replace the cell inoculation cassette 19 by the dummy cassette 70 so as to prevent the inducer from flowing from the inducer stimulation vessel 65 into the culture bag 18. When replacing the cell inoculation cassette 19 by the dummy cassette 70, the operation control panel 13 stops feeding of the culture medium from the culture medium cassette 20 to the culture bag 18 and the shaking culture by the shaking device 80 temporarily until the replacement of the cell inoculation cassette 19 by the dummy cassette 70 is completed.

Then, in Steps S59 to S64, when the operation control panel 13 determines that there is no more culture medium in the culture medium bag 67 in the culture medium cassette 20 from the measured value of the weight meter 43, the operation control panel 13 prompts the operator to replace the culture medium cassette 20 by a new culture medium cassette 20. When replacing the culture medium cassette 20 by the new culture medium cassette 20 as well, the operation control panel 13 stops feeding of the culture medium from the culture medium cassette 20 to the culture bag 18 and the shaking culture by the shaking device 80 temporarily until the replacement of the culture medium cassette 20 is completed.

The operation control panel 13 stops the first pump 48, the second pump 49 and the operating motor 81 and stops the perfusion culture and the shaking culture at a moment when the desired culture term in Step S64 is reached, or when the desired number of cells is reached (S65 in FIG. 17).

The operation control panel 13 then activates the second pump 49 to discharge the used culture medium in the culture bag 18 to the used culture medium bag 68 in the culture medium cassette 20 and condense the cells until the amount of the culture suspension in the culture bag 18 is reduced to about ½ to ⅓ on the basis of the measured value by the weight meter 43 (S66 in FIG. 17). To stop the shaking device in the condensing process is to prevent the large number of cells from flowing into the tube, and from clogging the filter.

The operation control panel 13 then stops the second pump 49 to complete the cell culture (S67 in FIG. 17). After having completed the culture, the cells in the culture bag 18 are transferred into the vessel for the centrifuge in the clean bench or the like by the operator and then the cells are collected by the centrifugation (Step S68 in FIG. 17).

In this configuration, according to the embodiment shown above, the following effects (1) to (8) are achieved.

(1) The image processing computer 14 processes the image of the cells in the cell inoculation cassette 19 picked up by the CCD camera 88 to acquire the evaluation parameters (the average projected area of the single cell, the increasing rate of the non-single cell) of the cell culture, and to determine and evaluate the culture state of the corresponding cells (the proliferation capability of the cells and the proliferation ability of the cells). The operation control panel 13 carries out the culture operation according to the culture state (the timing of transfer of the cells from the cell inoculation cassette 19 to the culture bag 18, the feeding of the culture medium at the predetermined feeding velocity from the culture medium cassette 20 to the culture bag 18, etc.). Consequently, since the culture state of the cells is determined in a non-contact, non-invasive state, the cells are prevented from getting damaged, and the risk of contamination and the loss of the cells due to the sampling are avoided.

The labor of the operator is alleviated as the operator needs not to carry out the culture operation one by one. And it is not necessary to open and close the main body door 21 of the incubator 11 and the canister door 31 of the canister 16 for observing the culture state. Therefore, the culture environment in the incubator 11 and the canister 16 is maintained in a desirable state.

In addition, the cells of one patient may be inoculated to the cell inoculation cassette 19 in the culture cassette 17 which is stored in the single canister 16, and the culture operation according to the culture state of the cells may be carried out on the individual bases. Therefore, the culture operation suitable for each patient is achieved, and the cross-contamination is avoided. Since the culture operation suitable for the culture state of the cells is achieved, the culture operation by the hour is enabled, and the culture is accelerated to shorten the culture term.

(2) The culture medium cassette 20 has a cassette structure, and is connected to the culture bag 18 and the cell inoculation cassette 19, which is also has a cassette structure. Therefore, the culture bag 18, in particular, is constantly retained in the canister 16 which provides an environment suitable for the culture. The change of the culture medium is enabled only by opening and closing the main body door 21 of the incubator 11 and the canister door 31 of the canister 16, and the number of times of opening and closing operation of the both doors 21 and 31 may be reduced. Therefore, fluctuation of the culture environment in the incubator 11 and the canister 16 may be restrained. Consequently, damages to the cells in the culture bag 18 in association with the environment change is reduced, and aseptic manipulation for supplying the culture medium to the culture bag 18 in the clean bench or the like may be omitted.

(3) The culture medium cassette 20, the cell inoculation cassette 19 and the culture bag 18 are connected to form a closed system. Therefore, the culture medium cassette 20, the cell inoculation cassette 19 and the culture bag 18 are maintained under the aseptic conditions.

(4) The culture suspension is stored in the liquid reservoir 78 of the culture bag 18 in the initial stage of the culture in the culture bag 18, and hence the cell density per area may be maintained at a suitable density. Therefore, the cells may proliferate efficiently in the initial stage of culture.

(5) When the cells proliferated in the culture bag 18 is introduced into the cell inoculation cassette 19 or the dummy cassette 70 and the images of the cells are acquired by the CCD camera 88, the number of cells and the form of the cells are observed by acquiring the cells proliferated in the culture bag 18 as the images without sampling.

(6) The used culture medium in the culture bag 18 is discharged and stored in the used culture medium bag 68 in the culture medium cassette 20, and hence the cells in the culture bag 18 may be condensed to increase the cell density. Therefore, the number of times of the operation of centrifugation for collecting the cells may be reduced. Consequently, the labor for collecting the cells is saved, and the damage of the cells in association with the centrifugation is reduced.

(7) When all the cells condensed in the culture bag 18 are collected to the cell collecting bag 72 mounted to the culture medium cassette 20, the cells may be collected by mounting the cell collecting bag 72 directly to the centrifuge. Therefore, the labor for collecting the cells may be saved.

(8) The culture suspension in the culture bag 18 is stirred by repeatedly pressing the flexible culture bag 18 having the culture medium to which the cells are inoculated stored therein by the projections 86 of the operating plate 85 in the shaking mechanism 91 of the shaking device 80. Therefore, the distribution of the cells and the concentration of the components of the culture medium in the culture bag 18 are homogenized, and the oxygen supply capacity is improved, so that the proliferation of the cells is accelerated and the efficiency of the cell culture is improved.

Since the cells are simply suspended in the culture suspension stirred by being pressed repeatedly by the operating plate 85 of the shaking device 80, the cells are prevented from getting damaged.

(9) The operation control panel 13 and the monitoring computer 15 collect and accumulate the cell culture-related data relating to the cell culture individually for the each culture unit 12 in the incubator 11 (the canister 16 and the culture cassette 17). Therefore, the culture log relating to the cells cultured in the arbitrary culture unit 12 is adequately known.

The operation control panel 13 and the monitoring computer 15 monitor the culture state of the cells on the basis of the cell culture-related data for the individual culture unit 12 in the incubator 11 (the canister 16 and the culture cassette 17). Therefore, trouble in the culture state may be monitored individually for the each culture unit 12.

Furthermore, the operation control panel 13 and the monitoring computer 15 control the operation of cell culture such as the change of the culture medium (replacement of the culture medium cassette 20) and collection of the cells after having completed the culture (collection of the cells by the culture bag 18 or the cell collecting bag 72). Therefore, the operation schedule for the operation (work) carried out by the operator individually for the each culture unit 12 in the incubator 11 is easily prepared.

(10) The control unit includes the operation control panel 13 being installed in a culture room 94 together with the incubator 11 and having a function to control the culture in the each culture unit 12 (the canister 16 and the culture cassette 17) in the incubator 11 and the monitoring computer 15 being installed in a monitor room 95 other than the culture room 94 and receiving and saving the data that the operation control panel 13 has and making the same available for display (inspection). Therefore, the culture state of the cells in the culture unit 12 in the incubator 11 in the culture room 94 may be observed, monitored and controlled in the monitor room 95 other than the culture room 94 using the monitoring computer 15. With this control, the log or the like is automatically recorded and stored, and occurrence of intentional alteration or erroneous recording is prevented.

(11) The canisters 16 in the incubator 11 which constitutes the culture units 12 are each isolated to avoid entry of the cells and/or bacteria by the air-intake filter 32 and the exhaust filter 33. Therefore, the cells in the culture bag 18 and the cell inoculation cassette 19 stored in the each canister 16 are prevented from being contaminated by bacteria.

(12) The blast fans 34 of all the canisters 16 in the single incubator 11 are configured to stop when the main body door 21 of the incubator 11 is opened. Therefore, the sealed state of the each canister 16 in the incubator 11 is maintained even when the main body door 21 of the incubator 11 is opened, so that the independent culture environment for the each canister 16 is preferably secured, and the fluctuation of the culture environments in the canisters 16 are restrained.

(13) Only one of the canister doors 31 of the canisters 16 in the single incubator 11 is allowed to be opened. Therefore, there is no probability that the two or more canister doors 31 of the canisters 16 are opened in the single incubator 11, so that the mix-up of the culture bags 18 and the cell inoculation cassettes 19 among the canisters 16 is prevented, and the cross-contamination of the cells is avoided.

[B] Second Embodiment

FIG. 21 to FIG. 24

Figure 21:
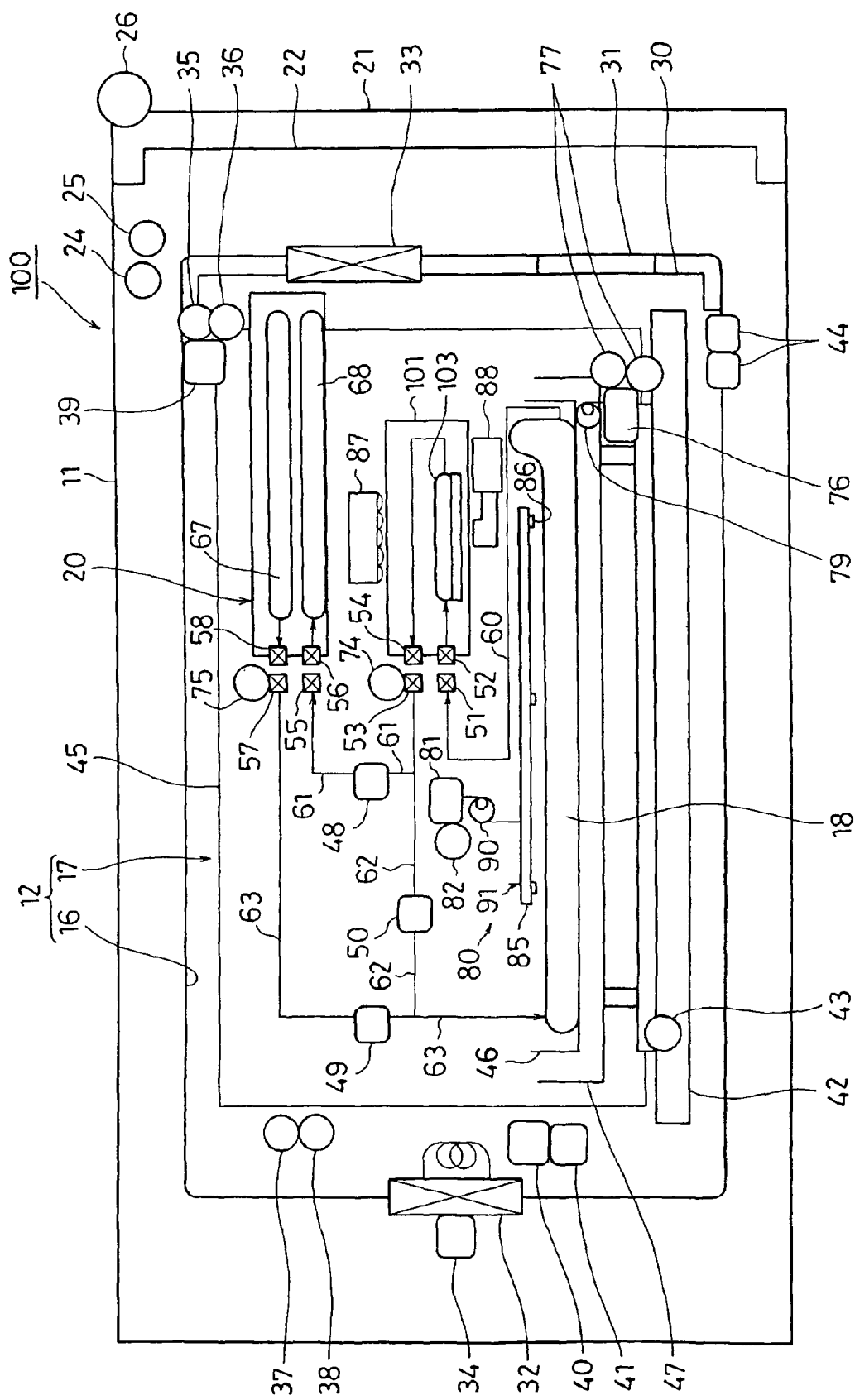
FIG. 21 is a layout drawing showing a configuration of the culture unit (the differentiation-inducing state) according to a second embodiment of the cell culture apparatus according to the invention.
Figure 22:
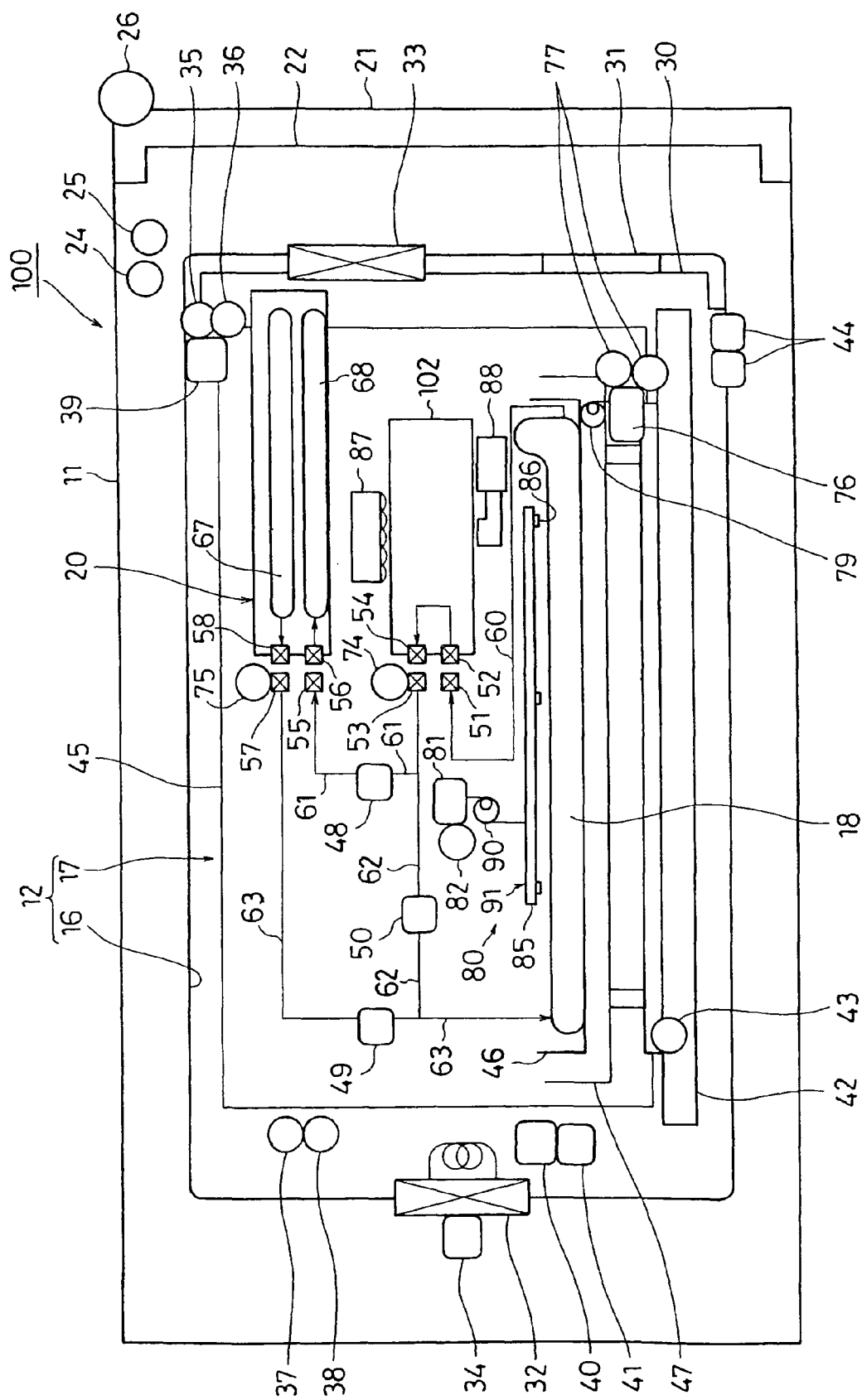
FIG. 22 is a layout drawing showing a configuration in a state before the differentiation induction of the culture unit in FIG. 21.

FIG. 21 is a layout drawing showing a configuration (differentiation-inducing state) of the culture unit of the cell culture apparatus according to a second embodiment of the invention. FIG. 22 is a layout drawing showing the configuration of the culture unit in FIG. 21 in a state before the differential inducement). In the second embodiment, the same parts as in the first embodiment are designated by the same reference numerals and description is omitted.

A cell culture apparatus 100 according to the second embodiment is an apparatus in which the cell inoculation cassette 19 (FIG. 5) in the cell culture apparatus 10 in the first embodiment is replaced by a differentiation-inducing cassette 101 as a differentiation-inducing culture vessel in which differentiation-inducing factor is added in advance. Then, the cell culture apparatus 100 activates the second pump 49 to introduce the culture medium from the culture medium bag 67 in the culture medium cassette 20 to the culture bag 18 to cause the cells to proliferate, and then activates the first pump 48 to introduce the proliferated cells to the differentiation-inducing cassette 101 to give a role to the corresponding cells, that is, differentiates the corresponding cells. The term "differentiation" in this specification means to give a role to the cells as cells of a heart, or to give a role to the same as cells of liver. As shown in FIG. 22, a dummy cassette 102 is arranged instead of the differentiation-inducing cassette 101 before the cells proliferated in the culture bag 18 are differentiated in the differentiation-inducing cassette 101, and the used culture medium in the culture bag 18 is discharged to the used culture medium bag 68 in the culture medium cassette 20 via the dummy cassette 102 by the activation of the first pump 48. The dummy cassette 102 functions as a flow path which simply allows the culture medium to flow, as in the case of the dummy cassette 70 (FIG. 5).

In the second embodiment, as shown in FIG. 21, the CCD camera 88 takes images of the cells differentiated in the differentiation-inducing cassette 101 at predetermined time intervals. A program for carrying out the shooting is stored in a storage device of the operation control panel 13. The image processing computer 14 carries out processing such as binarization or multithresholding on the images of the cells, and acquires the form of the cells as evaluation parameters. A program for carrying out the acquisition of the evaluation parameter is stored in the storage device of the image processing computer 14. The image processing computer 14 determines whether the corresponding cells are differentiated or not from the change of the form of the cells with time. The operation control panel 13 controls the differentiation-inducing operation by the differentiation-inducing cassette 101 upon reception of the signal from the image processing computer 14. For example, the operation control panel 13 continues the differentiation-inducing operation when the image processing computer 14 determines that the corresponding cells have a capability of differentiation. If not, the message saying so is displayed. The program for carrying out the determination of differentiation described above is stored in the storage device in the image processing computer 14, and a program for carrying out the differentiation-inducing operation is stored in the storage device in the operation control panel 13.

In the same manner as in the first embodiment, a program for acquiring the cell culture-related data, a program for monitoring the culture state of the cells and a program for controlling the culture operation of the cells are further stored in the storage device of the operation control panel 13 for the each canister 16 and the culture cassette 17 in the incubator 11. The operation control panel 13 collects and accumulates the cell culture-related data for the each canister 16 and the each culture cassette 17 in the incubator 11, monitors whether there is a trouble or not, and controls the culture operation such as the replacement of the culture medium cassette 20 (the change of the culture medium), and the replacement of the dummy cassette 102 by the differentiation-inducing cassette 101 in the same manner as in the first embodiment on the basis of the programs described above. The monitoring computer 15 receives the cell culture-related data, the culture log data, data relating to whether there is a trouble or not, and data relating to the culture operation from the operation control panel 13 for the each canister 16 and the each culture cassette 17 in the incubator 11, and stores the same to make these data available for display (inspection) in the same manner as in the first embodiment.

Although the acquisition of the cell culture-related data is achieved in the same manner as in the first embodiment, it is different in the case of the differentiation-inducing cassette 101. In other words, before the cell culture (see FIG. 18), when adding the differentiation-inducing factor to a differentiation-inducing vessel 103 (FIG. 21) in the differentiation-inducing cassette 101 in the clean bench or the like, the operation control panel 13 acquires the ID of the differentiation-inducing vessel 103, the ID of the differentiation-inducing factor and the operator's ID together with the date and time of operation and transmits the same to the monitoring computer 15. Then, when mounting the differentiation-inducing vessel 103 to the differentiation-inducing cassette 101, the operation control panel 13 acquires the ID of the differentiation-inducing vessel 103, the ID of the differentiation-inducing cassette 101 and the operator's ID together with the date and time of operation and transmits the same to the monitoring computer 15. During the cell culture (see FIG. 19), when removing the dummy cassette 102 and replacing the same by the differentiation-inducing cassette 101, the operation control panel 13 acquires the addresses of the incubator 11 and the canister 16, the ID of the differentiation-inducing cassette 101, the ID of the large tray 45 and the operator's ID together with the date and time of operation and transmits the same to the monitoring computer 15.

Figure 23:
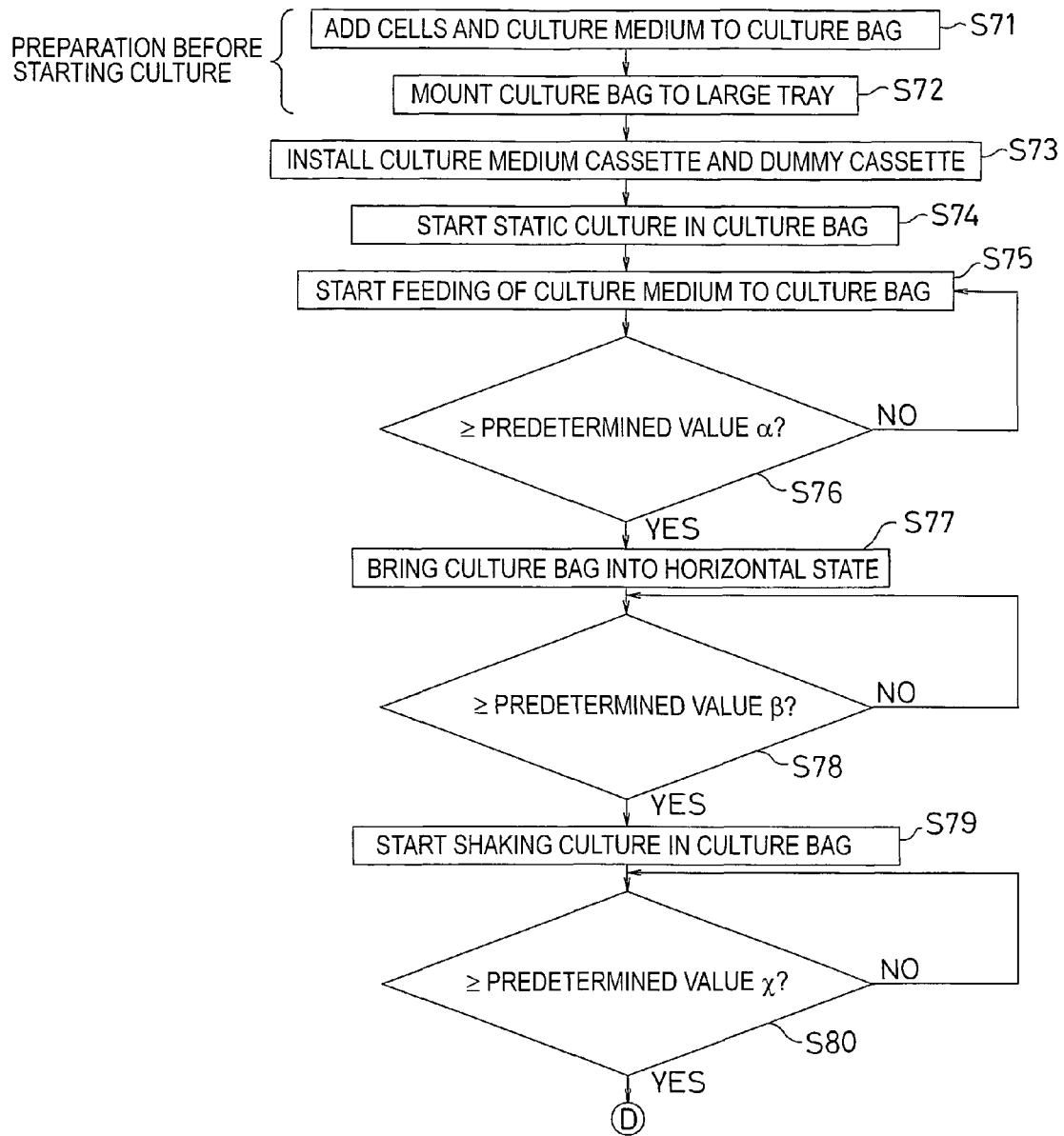
FIG. 23 is a flowchart showing process steps of a differentiation-inducing intermittent perfusion culture process in the culture unit in FIG. 21 and FIG. 22.
Figure 24:
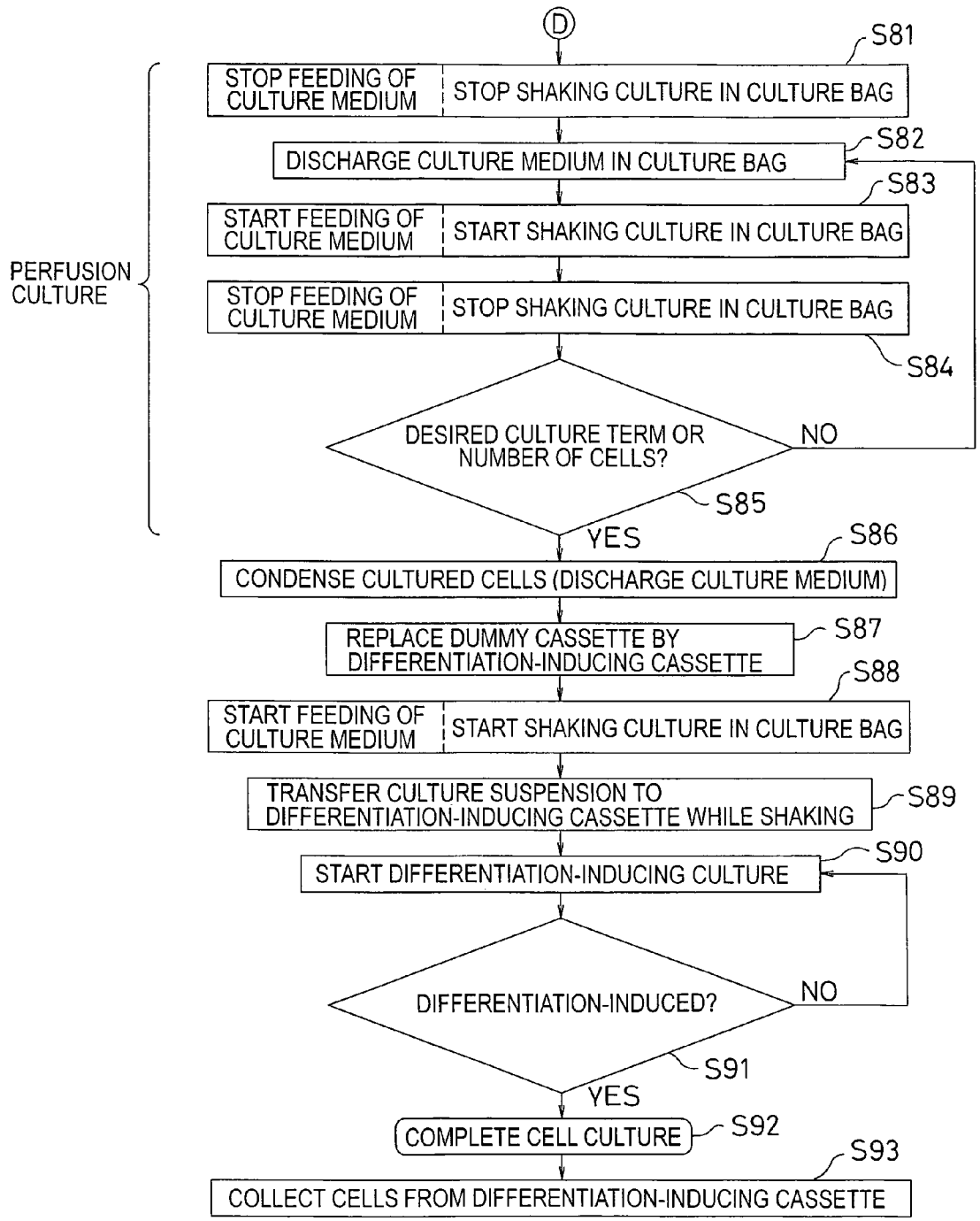
FIG. 24 is a flowchart showing steps following the process steps in FIG. 23.

Referring now to FIG. 23 and FIG. 24, a differentiation-inducing intermittent perfusion culture process carried out by the cell culture apparatus 100 will be described.

First of all, the operator adds a culture medium and cells to the culture bag 18 in the clean bench or the like (S71 in FIG. 23), places the culture bag 18 on the culture bag tray 47 via the platform 46, and attaches the culture bag tray 47 to the large tray 45 (S72 in FIG. 23). Then, the operator carries the large tray 45 into the single canister 16 illuminated by the indication lamp 44, for example, in green in the incubator 11.

Then, the operator mounts the culture medium cassette 20 to the large tray 45 in the canister 16, and mounts the dummy cassette 102 (FIG. 22) (S73 in FIG. 23). Then, the operator closes the canister door 31 of the canister 16 and the static culture of the cells in the culture bag 18 is started (S74 in FIG. 23). When carrying out the static culture, in a case in which the amount of the culture suspension in the culture bag 18 is small, the operator activates the inclined motor 76 to move the elevating unit of the platform 46 downward, and form the liquid reservoir 78 (FIG. 8) in the culture bag 18.

After having started the static culture, the operation control panel 13 activates the second pump 49, and feeds the culture medium from the culture medium bag 67 in the culture medium cassette 20 to the culture bag 18 (S75 in FIG. 23). The operation control panel 13 confirms whether the culture suspension in the culture bag 18 is increased to a level at least equal to the predetermined value ax or not from the measured value of the weight meter 43 (S76 in FIG. 23), and when the measured value of the weight meter is increased to a value at least equal to the predetermined value $\alpha$, the operation control panel 13 activates the inclined motor 76 to move the elevating unit of the platform 46 upward, and brings the culture bag 18 into the horizontal state to eliminate the liquid reservoir 78 (S77 in FIG. 23).

Subsequently, the operation control panel 13 determines whether the weight of the culture suspension in the culture bag 18 weighted by the weight meter 43 is increased to a level at least equal to the predetermined value $\beta$ or not (S78 in FIG. 23). At a timing when a weight is increased to value at least equal to the predetermined value $\beta$, the operation control panel 13 activates the operating motor 81 to activate the shaking device 80 to start the shaking culture (S79 in FIG. 23). Then, the operation control panel 13 continues to determine whether the weight of the culture suspension in the culture bag 18 measured by the weight meter 43 is increased to a value at least equal to the predetermined value χ or not (S80 in FIG. 23). At a timing when a weight is increased to a value at least equal to the predetermined value χ, the operation control panel 13 stops the second pump 49 to stop feeding of the culture medium from the culture medium bag 67 in the culture medium cassette 20 to the culture bag 18, stop the operating motor 81 and stop the shaking culture in the culture bag 18 (S81 in FIG. 23).

The operation control panel 13 activates the first pump 48 after having settled the cells in the culture bag 18 to discharge the used culture medium in the culture bag 18 to the used culture medium bag 68 in the culture medium cassette 20 (S82 in FIG. 24). Then, the operation control panel 13 activates the second pump 49 to feed the culture medium from the culture medium bag 67 in the culture medium cassette 20 to the culture bag 18, activates the operating motor 81 to carry out the shaking culture in the culture bag 18 by the shaking device 80 (S83 in FIG. 24). After having elapsed a predetermined time length, the operation control panel 13 stops the second pump 49, stops feeding of the culture medium from the culture medium bag 67 in the culture medium cassette 20 to the culture bag 18, stops the operating motor 81 and stops the shaking culture in the culture bag 18 (S84 in FIG. 24).

The operation control panel 13 determines whether the desired culture term depending on the date and time of usage of the cells to proliferate is reached or not, or the image processing computer 14 determines whether the desired number of cells is reached in the culture bag 18 or not (S85 in FIG. 24). When determining whether the desired number of cells is reached in the culture bag 18 or not, the operation control panel 13 activates the third pump 50 to transfer part of the cells in the culture bag 18 to the dummy cassette 102 and make the CCD camera 88 to take an image of the cells. The image processing computer 14 processes the image of the cells, determines whether the number of cells is at least equal to a specified value or not, and transmits the same to the operation panel 13. When the culture term or the number of cells is not reached, the operation control panel 13 repeats the operation from Steps S82 to S85.

The Steps S81 to S85 are steps of intermittent perfusion culture process in which discharge of the used culture medium in the culture bag 18 and supply (feed) of new culture medium into the culture bag 18 are carried out alternately.

In Steps S77 to S85, when the operation control panel 13 determines that there is no more culture medium in the culture medium bag 67 in the culture medium cassette 20 from the measured value of the weight meter 43, the operation control panel 13 prompts the operator to replace the culture medium cassette 20 by a new culture medium cassette 20. When replacing the culture medium cassette 20 by the new culture medium cassette 20 as well, the operation control panel 13 stops feeding of the culture medium from the culture medium cassette 20 to the culture bag 18 and the shaking culture by the shaking device 80 temporarily until the replacement of the culture medium cassette 20 is completed.

At the time point when the desired culture term is reached or when the desired number of cells is reached in Step S85, the operation control panel 13 activates the first pump 48 to discharge the used culture medium in the culture bag 18 to the used culture medium bag 68 in the culture medium cassette 20 and condense the cells until the culture suspension in the culture bag 18 is reduced to about ½ to ⅓ on the basis of the measured value by the weight meter 43 (S86 in FIG. 24).

Then, after having stopped the first pump 48 by the operation control panel 13, the operator replaces the dummy cassette 102 by the differentiation-inducing cassette 101 as shown in FIG. 21 (S87 in FIG. 24).

After having completed the replacement of the dummy cassette 102 by the differentiation-inducing cassette 101, the operation control panel 13 activates the control unit 29 to feed the culture medium in the culture medium bag 67 in the culture medium cassette 20 to the culture bag 18, and activates the operating motor 81 to carry out the shaking culture in the culture bag 18 by the shaking device 80 (S88 in FIG. 24). Then, the operation control panel 13 activates the first pump 48 to transfer the culture suspension in the culture bag 18 to the differentiation-inducing cassette 101 while continuing the shaking culture in the culture bag 18 and feeding of the culture medium from the culture medium cassette 20 (S89 in FIG. 24). Accordingly, the differentiation-inducing culture is started in the differentiation-inducing cassette 101 (S90 in FIG. 24).

The operation control panel 13 causes the CCD camera 88 to take images of the cells in the differentiation-inducing cassette 101 during the differentiation-inducing culture at predetermined time intervals (every six hours, for example). The image processing computer 14 processes the picked-up image, acquires the form of the cells as evaluation parameters, and determines whether the cells are differentiated in the differentiation-inducing cassette 101 or not from the change of the form of the cells with time (S91 in FIG. 24).

The operation control panel 13 stops the second pump 49, the first pump 48 and the operating motor 81 to stop the differentiation-inducing culture to complete the cell culture upon reception of the signal determining that the cells are differentiated from the image processing computer 14 in Step S91 (S92 in FIG. 24). After having completed the culture, the operator collects the cells in the differentiation-inducing cassette 101 by the cell collecting operation in the clean bench or the like (S93 in FIG. 24).

In this configuration, according to the second embodiment, the same effects as (2) to (6) and (8) in the first embodiment are achieved (provided that the cell inoculation cassette 19 is replaced by the differentiation-inducing cassette 101) and the following effect (9) is achieved.

(9) Since the culture state of the cells (whether the cells are differentiated or not) is determined by processing the images of the cells in the differentiation-inducing cassette 101 and acquiring the evaluation parameters (the form of the cells) of the cell culture, and the culture operation according to the culture state (the timing of culture medium feeding from the culture medium cassette 20 to the culture bag 18 at a predetermined feeding velocity, or the cell transfer from the culture bag 18 to the differentiation-inducing cassette 101) is carried out, the culture state of the cells is determined by a non-contact, non-invasive state. Therefore, the cells are prevented from getting damaged, the risk of contamination and the loss of the cells by sampling are avoided, and the labor of the operator is alleviated. Furthermore, since the cells of a single patient proliferate in the culture bag 18 in the culture cassette 17 and are differentiated in the differentiation-inducing cassette 101 which is stored in the single canister 16, the cell culture is adequately carried out for the individual patients, and the cross-contamination is avoided.

According to the cell culture apparatuses 10 and 102 in the first and second embodiments, the following effect (10) is achieved.

(10) The cell culture apparatuses 10 and 100 are both adapted to transfer the cells cultured in one of the plurality of culture vessels for culturing the cells in different environments to another culture vessel on the downstream side. In other words, in the cell culture apparatus 10, the cells are stimulated by the inducer for the proliferation in the cell inoculation cassette 19, which is one of the culture vessels, and then the cells are transferred from the cell inoculation cassette 19 to the culture bag 18 as still another culture vessel for causing the cells to proliferate. In the cell culture apparatus 100, the cells proliferate in the culture bag 18, which is one of the culture vessels, and then the cells are transferred from the culture bag 18 to the differentiation-inducing cassette 101, which is still another culture vessel for differentiating the cells. In this manner, according to the cell culture apparatuses 10 and 100, a variety of forms of the cell culture is achieved.

Although the invention has been described on the basis of the embodiments shown above, the invention is not limited thereto.

For example, in the description of the both embodiments shown above, the image processing computer 14 processes the images taken by the CCD camera 88 and calculates the evaluation parameters, and determines the culture state of the cells (the proliferation capability of the cells, the proliferation ability of the cells) from the evaluation parameters. However, the function of the image processing computer 14 may be carried out by the operation control panel 13.

The cell images may be taken in the culture bag 18 by the CCD camera 88. When the shaking culture by the shaking device 80 is not carried out in the inducer stimulating consecutive perfusion culture process (FIG. 16 and FIG. 17), it is not necessary to dispose the filter 71 between the second pump 49 and the culture bag 18.

In the description of the both embodiments shown above, the shaking device 80 is used to stir the culture suspension for causing the cells to proliferate. However, it is also possible to shake the culture bag 18 in the vertical direction or to swing the same in the lateral direction to mix the culture suspension and homogenize the distribution of cells and the concentration of the components of the culture medium or to enhance the oxygen supply capacity.

In the description in the both embodiments, the operation control panel 13 and the image processing computer 14 control the individual canisters in the one incubator. However, it is also possible to prepare a plurality of the incubatores of the same type and control the individual canisters in the incubators by the operation control panel 13 and the image processing computer 14.

[C] Third Embodiment

FIG. 25

Figure 25:
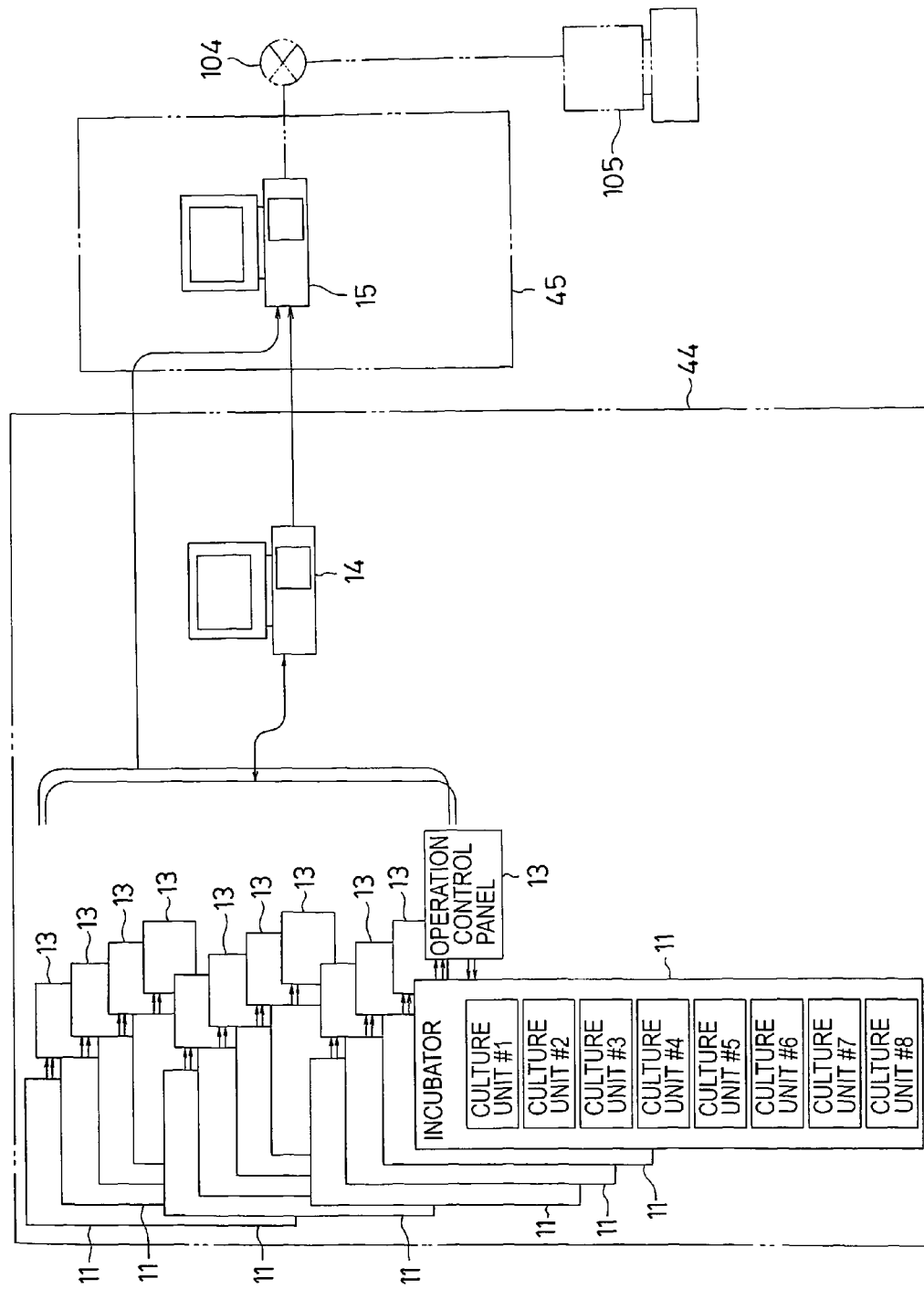
FIG. 25 is a configuration drawing showing a third embodiment of the cell culture system according to the invention.

In the description in the first and second embodiments, one each of the operation control panel 13 and the image processing computer 14 control the operation of the individual canisters 16 in the single incubator 11, and one each of the operation control panel 13 and the monitoring computer 15 monitor and control the cell culture. However, as in a third embodiment shown in FIG. 25, it is also possible to install a plurality of the incubators 11, arrange one each of the operation control panel 13 in the each incubator 11, and connect the single image processing computer 14 and the single monitoring computer 15 to the each operation control panel 13, so that the cell culture carried out in the each canister 16 of the plurality of incubators 11 is monitored and controlled by the monitoring computer 15. With this control, the log or the like is automatically recorded and stored, and occurrence of intentional alteration or erroneous recording is prevented.

In the first and second embodiments (FIG. 1), or in the third embodiment (FIG. 25), it is possible to connect a remote monitor computer 105 to the single monitoring computer 15 using a public network 104. In this case, the abnormal culture in the specific canister 16 of the specific incubator 11 is advantageously known quickly at a remote location using the remote monitor computer 105.

[D] Fourth Embodiment

FIG. 26 to FIG. 38

Figure 26:
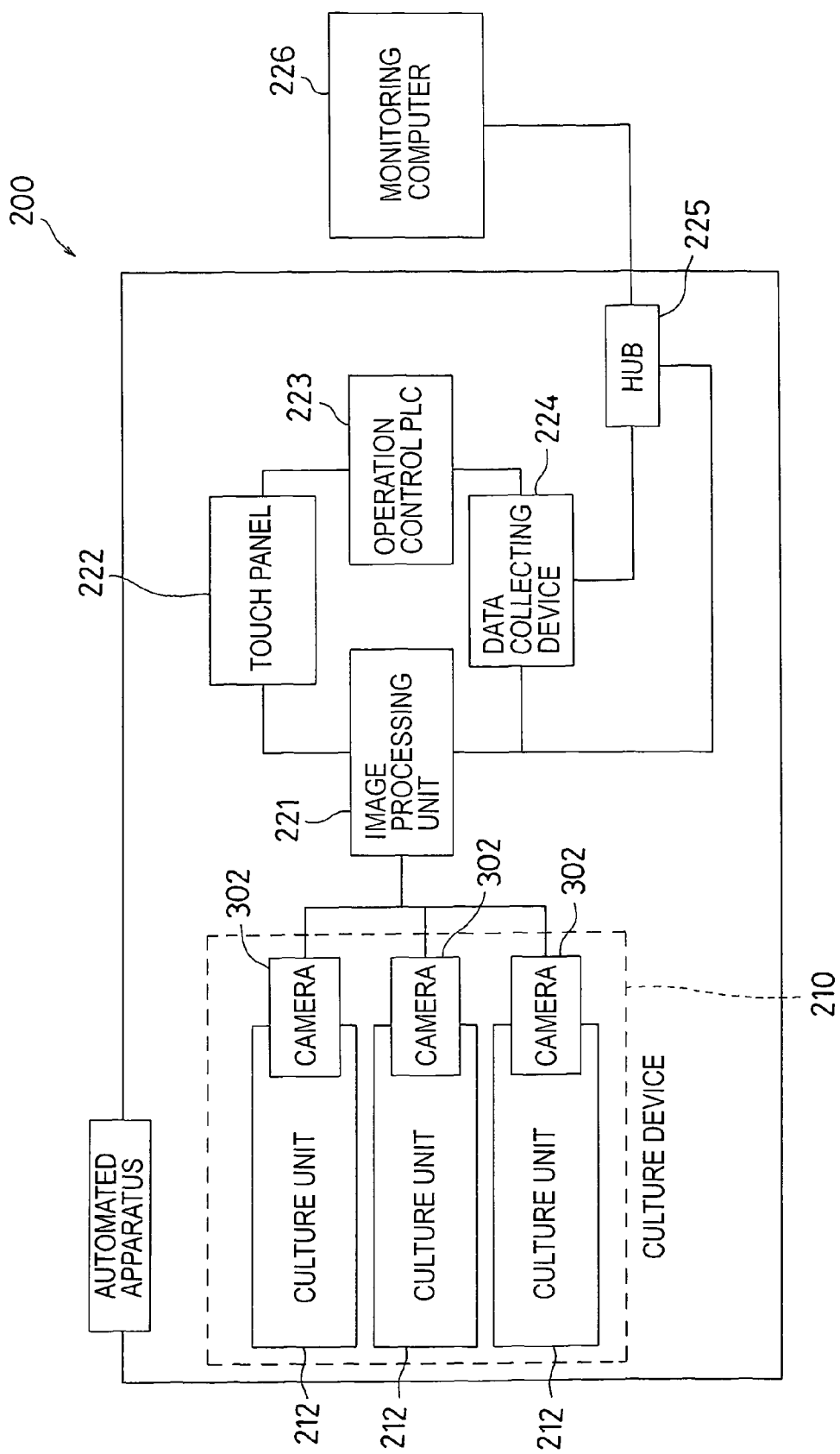
FIG. 26 is a configuration drawing showing a fourth embodiment of the cell culture apparatus according to the invention.
Figure 27:
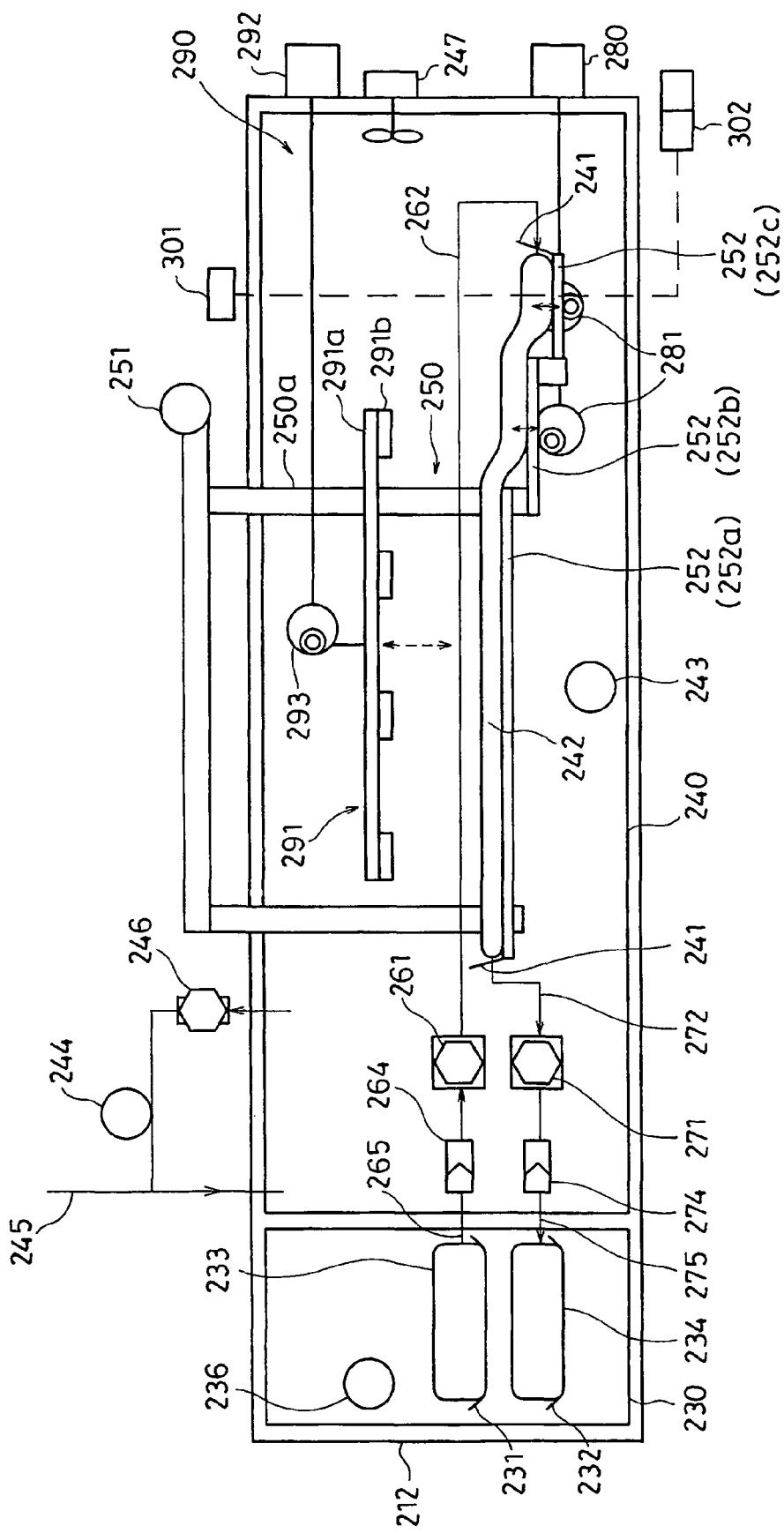
FIG. 27 is a layout drawing showing a configuration of the culture unit including a culture chamber and a low-temperature chamber spatially independent from each other, a culture bag tray stored in the culture chamber, and a culture medium bag/waste water bag tray stored in the low-temperature chamber in the cell culture apparatus according to the fourth embodiment.

FIG. 26 is a configuration drawing showing the cell culture apparatus according to a fourth embodiment of the invention. FIG. 27 is a layout of a cell culture apparatus 200 according to the fourth embodiment showing a configuration of a culture unit 212 including a single spatially independent culture chamber 240 and low temperature chamber 230, a culture bag tray 241 stored in the culture chamber 240, a culture medium bag tray 231 and waste water bag tray 232 stored in the low temperature chamber 230.

The cell culture apparatus 200 shown in FIG. 26 is specifically adapted to culture suspension cells used for the immune cell therapy, and includes a culture device 210 provided with a plurality of (three, for example) the culture units 212, an operation control PLC (programmable logic controller) 223 for controlling the operation of the plurality of culture units 212, an image processing unit 221 for processing cell images, a data collecting device 224 for collecting all the data, a touch panel 222 for displaying information of and entering the control of the operation control PLC 223 and the image processing unit 221, and a monitoring computer 226 being connected to the operation control PLC 223, the image processing unit 221 and a data collecting device 224 via a hub 225 for monitoring the cell culture apparatus 200 and the culture unit 212. The operation control PLC 223 and the image processing unit 221 function as control units. The plurality of culture units 212 are each provided with an observation camera (CCD camera) 302.

The known suspension cells include peripheral blood mononuclear cells, LAK cells (Lymphokine Activated killer cells), neural stem cells and ES cells. These types of suspension cells are referred simply to as "cells", hereinafter. The cell culture apparatus 200 is also applicable to a case of culturing adherent cells (mesenchymal stem cells, for example) other than the suspension cells.

The cell culture apparatus 200 has a structure in which a plurality of (three, for example) spatially and structurally independent culture units 212 stacked one on top of another, and the each culture unit 212 is divided into the low temperature chamber 230 and the culture chamber 240 as shown in FIG. 27. The cell culture apparatus 200 includes a culture bag tray 241, a culture medium bag tray 231 and a waste water bag tray 232 stored therein. A culture bag 242 as an antibody stimulating and proliferation culture vessel is placed on the culture bag tray 241 as described later in detail, and a culture medium bag (new culture medium bag) 233 as a culture medium storage unit and a waste water bag (waste culture medium bag) 234 as a waste water bag tray are placed on the culture medium bag tray 231 and the waste water bag tray 232, respectively.

The culture unit 212 includes an openable and closable doors (not shown) for the culture chamber 240 and the low temperature chamber 230. The culture unit 212 maintains the environment (temperature and $CO_2$ concentration) in the culture chamber 240 to an environment required for culturing the cells in the state in which the door is closed, and the environment (temperature) in the low temperature chamber 230 to an environment optimal for preserving the culture medium.

Therefore, the culture unit 212 includes temperature sensors 236 and 243, a $CO_2$ sensor 244, a door sensor (not shown) and a heater (not shown) disposed therein. A gas cylinder (not shown) installed outside is coupled to the cell culture apparatus 200 (the culture unit 212) via a $CO_2$ supply system 245. Signals from the temperature sensors 236 and 243, the $CO_2$ sensor 244 and the door sensor are transmitted to the operation control PLC 223. The operation control PLC 223 controls the heater on the basis of the temperature signals from the temperature sensors 236 and 243, and controls the amount of $CO_2$ gas supplied from the gas cylinder into the individual culture units 212 on the basis of the $CO_2$ concentration signal from the $CO_2$ sensor 244. The $CO_2$ in the room is discharged by a predetermined constant value by a circulation pump 246.

The operation of a stirring fan 247 is controlled by the operation control PLC 223 and, when the signal indicating the fact that the door of the culture unit 212 is opened is transmitted from the door sensor to the operation control PLC 223, the operation of the stirring fan 247 is stopped and the environmental change in the culture unit 212 is alleviated.

The cell culture apparatus 200 has a dry heat sterilization function, and is able to sterilize the interior of the apparatus and the individual trays in a state in which the culture bag tray, the culture medium bag tray and the waste water bag tray are set therein, so that the proliferation of bacteria in the culture unit 212 is prevented. The individual culture units 212 have an independent space structure, the each culture unit 212 is isolated from the cells in other culture units 212 and the culture bag 242, the culture medium bag 233 and the waste water bag 234 stored in the culture unit 212 are connected in the clean bench or the like and then is installed in the culture unit 212. Therefore, the culture bag 242 stored in the culture unit 212 is secured in a closed system (non-open system), and contamination that the cells in the culture bag 242 is contaminated by bacteria is prevented.

The culture unit 212 further includes the door sensor (not shown), the door lock sensor (not shown), the temperature sensors 236 and 243, a door lock mechanism (not shown), the heater (not shown) and the stirring fan 247 disposed therein. The operation control PLC 223 controls the heater on the basis of the temperature signal from the temperature sensors 236 and 243. The operation control PLC 223 controls the operation of the stirring fan 247 to circulate the air and $CO_2$ gas in the culture chamber 240. In this manner, the interior of the culture chamber 240 is maintained in an environment optimal for culturing the cells.

The operation control PLC 223 controls the action of the door lock mechanism so that two or more doors of the culture units 212 are not opened simultaneously in one single cell culture apparatus 200. Accordingly, erroneous installation of the cells or the culture medium among the different culture units 212 is prevented. The locking action of the door lock mechanism is detected by the door lock sensor and is transmitted to the operation control PLC 223. The opened or closed states of the doors of the culture units 212 are detected by the door sensor and transmitted to the operation control PLC 223.

A frame 250 for supporting the culture bag tray 241 to be stored in the culture chamber 240 is provided in the lower portion in the culture unit 212 shown in FIG. 27, and a weight meter 251, which supports the frame 250, is installed on the frame 250 above the culture unit 212. The weight meter 251 is adapted to measure the weight of the culture bag 242 of the culture bag tray 241 stored in the culture chamber 240, and actually, measures the amount of culture medium supplied from the culture medium bag 233 to the culture bag 242 and the amount of waste water discharged from the culture bag 242 to the waste water bag 234. The measured values of the weight meter 251 are also transmitted to the operation control PLC 223. The main body of the culture unit 212 is provided with an indication lamp (not shown) for indicating the presence or absence of the culture bag 242 in the culture unit 212. The operation control PLC 223 illuminates the indication lamp, for example, in red, when the culture bag 242 is stored in the culture chamber 240, and illuminates the indication lamp, for example, in green, when the culture bag 242 is not stored in the culture chamber 240.

The culture bag tray 241 will be described here.

The culture bag 242 is mounted on the culture bag tray 241 as shown in FIG. 27, and the culture bag 242 is a culture vessel to culture the cells. The culture bag 242 is a function expressing culture vessel for causing the cells to express the function (for example, to cause the cells to proliferate, to cause the cells to differentiate), and is an antibody stimulating culture vessel for stimulating the cells by the antibody for proliferation in this embodiment. It also functions as a proliferation culture vessel for causing cells to proliferate stimulated by the antibody in the same culture bag 242.

The culture bag 242 is a flexible vessel for storing the culture medium in which the cells are inoculated, and is placed on the culture bag tray 241 via a platform 252. The culture bag 242 is a bag formed of, for example, oxygen permeable material.

The culture unit 212 will now be described.

In the culture chamber 240, a supply pump 261 and an exhaust pump 271 are arranged as shown in FIG. 27. The culture bag 242 is connected at one end thereof to a coupling of a supply system 264 via the supply pump 261 using a tube 262. The culture bag 242 is also connected at the other end to an exhaust system coupling 274 via the exhaust pump 271 using a tube 272.

In the culture unit 212, the culture bag 242 is connected to the coupling of a supply system 264 via the tube 262, and is connected to the culture medium bag 233 via a tube 265. The culture bag 242 is connected to the exhaust system coupling 274 via the tube 272 and is connected to the waste water bag 234 via a tube 275.

The culture bag 242 is configured into a cassette structure, as shown in FIG. 27, which is immobilized with the antibody on the inner side of the part of the bottom surface, connected to the supply pump 261 of the culture bag 242, added the culture medium in the culture bag 242, inoculated the cells on the culture medium and installed on the culture bag tray 241. The operation to immobilize the antibody and add the culture medium and the cells in the culture bag 242 is carried out under the aseptic conditions in the clean bench or the like.

The culture environment for causing the proliferation function of the cells to express, that is, by stimulating the cells by the antibody and the culture environment for causing the cells to proliferate are established in the same culture bag 242 by making part of immobilized antibody in the culture bag 242. Therefore, by supplying the culture medium to the cells which are stimulated by the antibody in a part of the culture bag 242 and started to proliferate, an efficient proliferation is enabled in the same culture bag 242.

The culture medium bag 233 as a culture medium storage vessel and the waste water bag 234 as a used culture medium storage vessel are placed on the culture medium bag tray 231 and the waste water bag tray 232, respectively, and each are configured into a cassette structure. The culture medium bag 233 is adapted to store the culture medium to be supplied to the culture bag 242. The waste water bag 234 is adapted to store the used culture medium (supernatant) discharged from the culture bag 242. With the cassette structure of the culture medium bag tray 231, the change and supply of the culture medium is enabled only by mounting the culture medium bag tray 231 into the low temperature chamber 230 in the culture unit 212 in a state in which the culture bag 242 is maintained in the culture chamber 240.

The culture bag tray 241 is detachably mounted to the culture unit 212. At this time, the a coupling of a supply system 264 of the culture bag 242 is coupled to a joint of the culture medium bag 233, and the exhaust system coupling 274 is coupled to a joint of the waste water bag 234 respectively under the aseptic conditions. In other words, the coupling of a supply system 264 and the joint of the culture medium bag 233 are coupled by, for example, inserting a rubbery joint on one of those to a needle joint on the other one of those under the aseptic conditions. Coupling between the exhaust system coupling 274 and the waste water bag 234 is also the same. The work to couple the culture bag 242 with the culture medium bag 233 and the waste water bag 234 is carried out in the clean bench or the like under the aseptic conditions.

With the connection among the culture bag 242, the culture medium bag 233 and the waste water bag 234 as described above, a closed loop in which the culture medium in the culture medium bag 233 on the culture medium bag tray 231 is supplied to the culture bag 242 by the activation of the supply pump 261, and the used culture medium in the culture bag 242 is discharged to the waste water bag 234 on the waste water bag tray 232 by the activation of the exhaust pump 271 is established. With the configuration of this closed loop, the system (the culture bag 242, the culture medium bag 233 and the waste water bag 234) is maintained under the aseptic conditions.

The culture (cell proliferation) in the culture bag 242 includes the static culture (simple feeding) in which the supply pump 261 is activated to supply (feed) the culture medium in the culture medium bag 233 on the culture medium bag tray 231 to the culture bag 242 to cause the cells to proliferate, the perfusion culture in which the supply pump 261 and the exhaust pump 271 are activated to discharge the used culture medium in the culture bag 242 to the waste water bag 234 on the waste water bag tray 232 and supply the culture medium in the culture medium bag 233 to the culture bag 242 to cause the cells to proliferate, and the shaking culture using a shaking device 290 described later. Among these, the perfusion culture includes the intermittent perfusion culture in which discharge of the used culture medium and supply of the culture medium are carried out alternately, and the consecutive perfusion culture in which the discharge of the culture medium and the supply of the culture medium are carried out simultaneously. In the consecutive perfusion culture, a filter for preventing transfer of cells is normally disposed in the tube 272 between the culture bag 242 and the exhaust pump 271 to prevent the cells in the culture bag 242 from being discharged to the waste water bag 234.

After having completed the proliferation of the cells in the culture bag 242, the used culture medium in the culture bag 242 is discharged to the waste water bag 234 of the waste water bag tray 232, and the cells in the culture bag 242 is condensed. The discharge of the used culture medium is carried out by the activation of the exhaust pump 271, and is carried out until the amount of the culture medium and the cells in the culture bag 242 is reduced to about ½ to ⅓ in quantity by the control of the operation control PLC 223 on the basis of the measured value by the weight meter 251. By the condensation of the cells in the culture bag 242, the number of times of centrifugation carried out by a centrifuge carried out later is reduced.

In the waste water bag tray 232, it is also possible to replace the waste water bag 234 by a cell collecting bag as a cell collecting vessel which is attachable to the centrifuge after having condensed the cells in the culture bag 242 as described above, and then supply the culture suspension (culture medium and cells) in which the cells are condensed in the culture bag 242 into the cell collecting bag by activating the exhaust pump 271, provided that the filter is not disposed in the tube 272. Accordingly, collection of the cells in the bag which is attachable to the centrifuge may be carried out within the culture unit 212, which is a space in the closed system, so that the labor for collecting the cells is saved.

Figure 28:
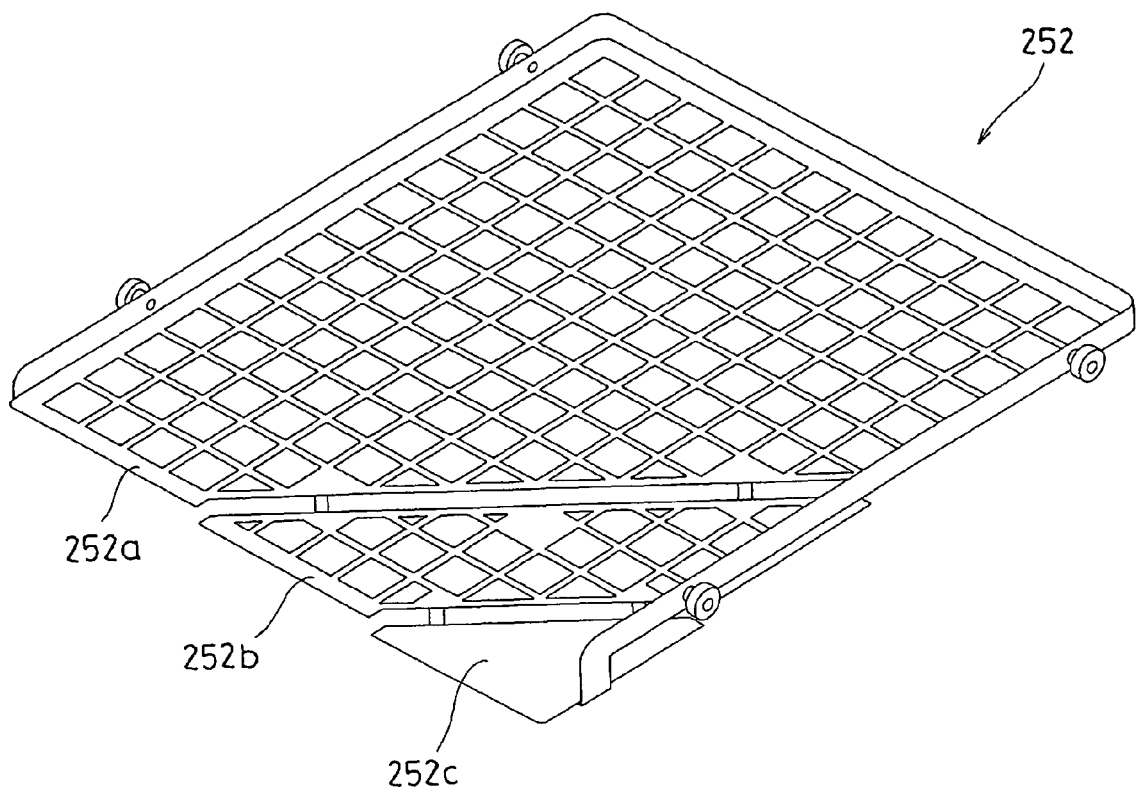
FIG. 28 is a perspective view showing a configuration of a platform in FIG. 27.

In this case, as shown in FIG. 27, the culture bag tray 241 is stored in the culture unit 212 and the culture bag tray 241 is supported by the frame 250 of the culture chamber 240. The platform 252 for directly placing the culture bag 242 on the culture bag tray 241 includes a non-elevating part 252*a*, and a plurality of area-changing parts 252*b* and 252*c* which are able to move upward and downward. The culture area of the culture bag 242 is controlled by the area-changing parts 252*b* and 252*c*. Installed below the portion of the culture tray 241 where the area-changing parts 252*b* and 252*c* are arranged are an inclined motor (elevating mechanism 280), a cam mechanism 281 and a positioning sensor (not shown). The inclined motor 280 rotates the cam mechanism 281 and moves upward and downward the area-changing parts 252*b* and 252*c* of the platform 252 separately and independently from each other. The positions of the elevating units are detected by the positioning sensor, and transmitted to the operation control PLC 223. The inclined motor 280 is controlled by the operation control PLC 223 so as to move the area-changing parts 252*b* and 252*c* of the platform 252 downward in the initial stage of culture in the culture bag 242. Accordingly, a liquid reservoir is formed at portions of the culture bag 242 corresponding to the area-changing parts 252*b* and 252*c*. For example, the culture area of the platform 252 shown in FIG. 28 is changed in three stages by moving the heights of the area-changing parts 252*b* and 252*c* upward and downward respectively. Three or more of the area-changing parts may be provided, whereby the finer adjustment of the culture area is achieved. FIG. 28 is a perspective view showing a configuration of the platform 252 in FIG. 27.

By the cells and the culture medium being stored in the liquid reservoirs in the initial stage of culture in the culture bag 242, a culture condition suitable for antibody stimulation, that is, the cell density in the culture bag 242 is maintained to a density which is preferable for the proliferation. In the middle stage or the later stage in which the culture medium and the cells in the culture bag 242 are increased to a value larger than the predetermined value, the inclined motor 280 moves the area-changing parts 252*b* and 252*c* of the platform 252 upward via the cam mechanism 281, and maintains only the parts having the predetermined area of the culture bag 242 in the horizontal state, so that the areas of the liquid reservoirs are changed. By changing the areas of the liquid reservoirs for the cells and the culture medium according to the progress of culture, the cell density per area in the culture bag 242 is maintained to a density preferable for the proliferation, so that the cells efficiently proliferate in the cell proliferation stage.

For example, when the platform 252 is able to form two stages of liquid reservoirs as shown in FIG. 28, first of all, the culture medium and the cells are retained in a portion of the area-changing part 252*c*, which is the lowest part, in FIG. 28 to avoid lowering of the density of the cells.

When the cells has started the proliferation and hence the amount of the culture medium is increased, the height of the area-changing part 252*c* in FIG. 28 is moved upward by one stage to align the area-changing part 252*b* and the area-changing part 252*c* at the same level, so that the area of the culture bag 242 which is usable for the culture is enlarged by a predetermined amount. Accordingly, the density of the cells which is preferable for the proliferation may be maintained for a certain time length again.

When the cells further proliferate and hence the amount of the culture medium is increased, the area-changing part 252b and the area-changing part 252c are moved upward by one stage to align with the part 252a, so that the culture is carried out in the entire part of the culture bag 242.

Furthermore, a shaking mechanism 291 of the shaking device 290 is installed above the culture bag tray 241 where the culture bag 242 is arranged as the pressing unit in the culture chamber 240 as shown in FIG. 27. The shaking device 290 includes the shaking mechanism 291, an operating motor 292, a cam mechanism 293 and the positioning sensor (not shown). As shown in FIG. 27, the shaking mechanism 291 includes an operating plate 291a as the pressing unit disposed to the apparatus frame 250 via the guide rod 250a so as to be capable of moving upward and downward, and a plurality of projections 291b projecting from the bottom surface of the operating plate 291a. When the operating plate 291a is moved upward and downward alternately on the basis of the action of the cam mechanism 293 by the operating motor 292, the projections 291b of the operating plate 291a presses the culture bag 242 positioned below the shaking mechanism 291 repeatedly, that is, repeats pressing and releasing with respect to the culture bag 242. Accordingly, the culture medium in the culture bag 242 is stirred, and the cells in the culture bag 242 floats and moves in the culture medium, so that the distribution of the cells and oxygen concentration distribution in the culture bag 242 are homogenized, and hence the proliferation of the cells is promoted.

Figure 29A:
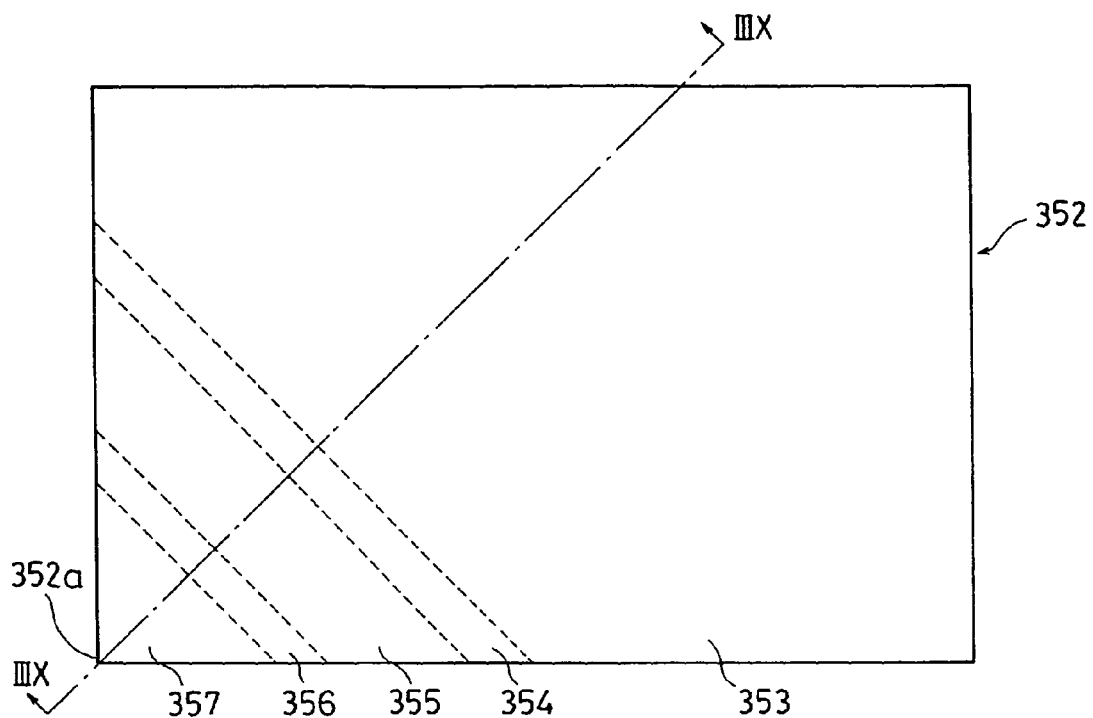
FIG. 29A is a plan view showing a configuration of the platform according to a modification of the fourth embodiment, showing a state in which a non-elevating part and all area-changing parts are aligned on the same plane.
Figure 29B:
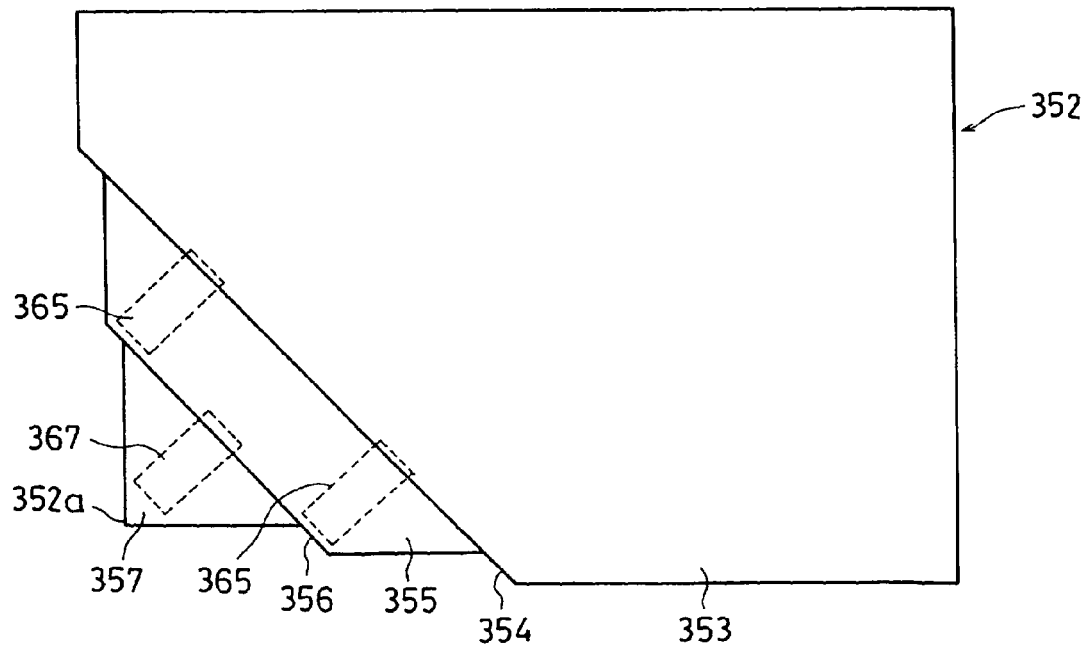
FIG. 29B is a plan view showing a configuration of the platform according to a modification of the fourth embodiment, showing a state in which the area-changing parts are moved downward.
Figure 30A:
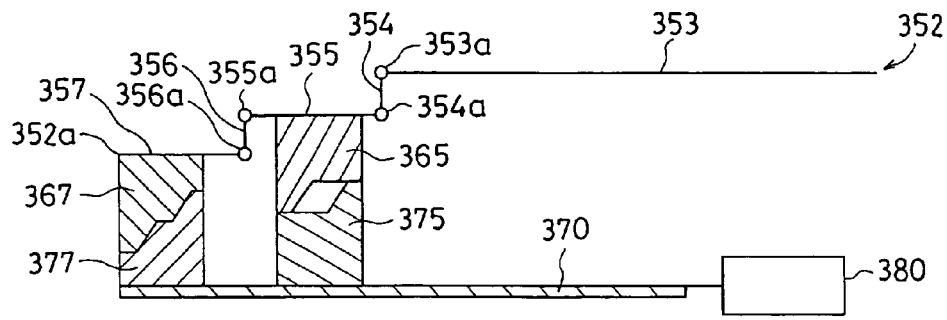
FIG. 30A is a partially cross-sectional view taken along the line IIIX-IIIX in FIG. 29A showing a state in which the area-changing parts are lowered to arrange the non-elevating part and the area-changing parts in a staircase pattern on different planes.
Figure 30B:
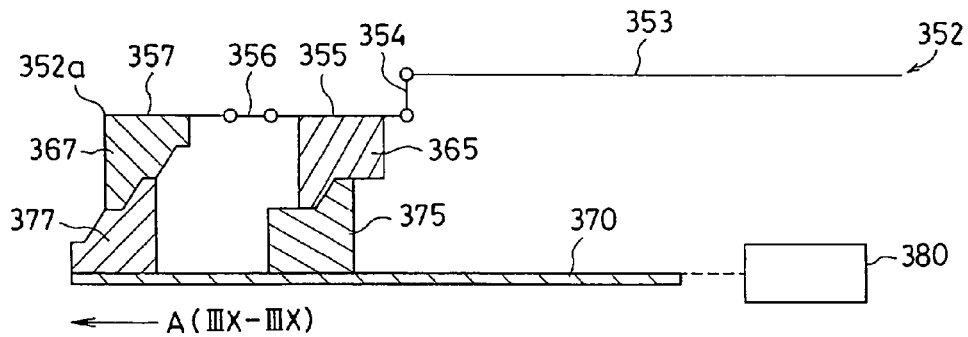
FIG. 30B is the partially cross-sectional view taken along the line IIIX-IIIX in FIG. 29A showing a state in which three area-changing parts from among the four area-changing parts are aligned on the same plane.
Figure 30C:
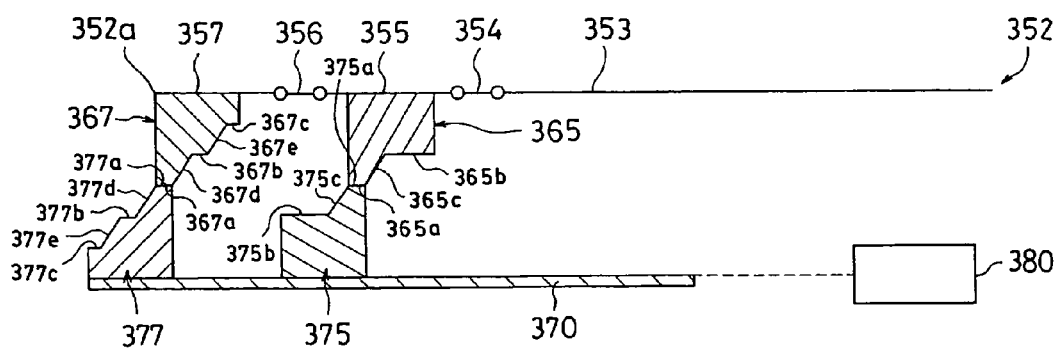
FIG. 30C is the partially cross-sectional view taken along the line IIIX-IIIX in FIG. 29A showing a state in which the non-elevating part and all the area-changing parts are aligned on the same plane.

It is also possible to use a platform 352 shown in FIG. 29 and FIG. 30 instead of the platform 252 described above to change the culture area in the culture bag 242 placed on the platform 352. FIGS. 29A and 29B are plan views showing a configuration of the platform 352 according to a modification of the fourth embodiment. FIG. 29A is a drawing showing a state in which a non-elevating part 353, and all area-changing parts 354, 355, 356 and 357 are aligned on the same plane, and FIG. 29B shows a state in which the area-changing parts are moved downward. FIGS. 30A to 30C are partly cross-sectional views taken along the line IIIX-IIIX in FIG. 29A. FIG. 30A is a drawing showing a state in which the area-changing parts are moved downward, and the non-elevating part 353, the area-changing part 355 and the area-changing part 357 are arranged in a staircase pattern on different planes. FIG. 30B is a drawing showing a state in which the three of the area-changing parts 355, 356 and 357 from among four area-changing parts are aligned on the same plane. FIG. 30C is a drawing showing a state in which the non-elevating part 353 and all the area-changing parts 354, 355, 356 and 357 are aligned on the same plane.

As shown in FIGS. 29A and 29B, the platform 352 includes area-changing parts 357, 356, 355 and 354 which are obtained by cutting a corner 352a of a rectangle in plan view in sequence in the shapes of isosceles triangles each having the corner as an apex, and a non-elevating part 353. The non-elevating part 353 is arranged on the horizontal plane. As shown in FIG. 30, the non-elevating part 353 is coupled to the variable area part 354 by a joint member 353a, the area-changing part 354 is coupled to the area-changing part 355 by a joint member 354a, the area-changing part 355 is coupled to the area-changing part 356 by a joint member 355a, and the variable area part 356 is coupled to the area-changing part 357 by a joint member 356a, so as to be rotatable with respect to each other. The joint members 353a, 354a, 355a and 356a may be, for example, hinges.

Although the platform 352 includes four area-changing parts, the number of the area-changing parts may be two to three, or may be five or more.

The area-changing parts 355 and 357 includes supporting legs 365 and 367 fixedly adhered on the lower surfaces thereof respectively.

As shown in FIG. 30C, the lower surface of the supporting leg 365 includes a plane 365a and a plane 365b arranged in sequence from the side of the corner 352a of the platform 352 on a horizontal plane, and an inclined plane 365c which connects the planes 365a and 365b, and the plane 365a is positioned at a lower level than the plane 365b. On the other hand, the lower surface of the supporting leg 367 includes planes 367a, 367b and 367c arranged in sequence from the side of the corner 352a of the platform 352 on a horizontal plane, an inclined plane 367d which connects the plane planes 367a and 367b, and an inclined plane 367e which connects the plane 367b and the plane 367c. The plane 367a is positioned at a lower level than the plane 367b, and the plane 367b is positioned at a lower level than the plane 367c. The distance between the plane 365a and the area-changing part 355 is the same as the distance between the plane 367a and the area-changing part 357, and the distance between the plane 365b and the area-changing part 355 is the same as the distance of the plane 367b from the area-changing part 357.

A height adjusting plate 370, which is movable along the line IIIX-IIIX in FIG. 29A (the direction indicated by an arrow A in FIG. 30B) by a motor 380 is arranged below the platform 352. Elevating members 375 and 377 for moving the area-changing parts upward and downward are fixedly adhered on the height adjusting plate 370.

As shown in FIG. 30C, the upper surface of the elevating member 375 includes a plane 375b and a plane 375a arranged in sequence from the side of the corner 352a of the platform 352 on a horizontal plane and an inclined surface 375c which connects the planes 375a and 375b, and the plane 375a is positioned at a level higher than the plane 375b. On the other hand, the upper surface of the elevating member 377 includes planes 377c, 377b and 377a arranged in sequence from the side of the corner 352a of the platform 352 on a horizontal plane, an inclined plane 377d which connects the plane 377a and the plane 377b, and an inclined plane 377e which connects the plane 377b and the plane 377c. The plane 377a is positioned at a level higher than the plane 377b, and the plane 377b is positioned at a level higher than the plane 377c. The upper surface of the elevating member 377 has a shape corresponding to the lower surface of the supporting leg 367 and, when the inclined planes 377d and 377e are brought into abutment with the inclined planes 367e and 367d of the supporting leg 367 respectively, the planes 377a, 377b and 377c comes into abutment with the planes 367c, 367b and 367a of the supporting leg 367, respectively. The distance between the plane 375a and the upper surface of the height adjusting plate 370 is the same as the distance of the plane 377a from the upper surface of the height adjusting plate 370, and the distance of the plane 375b from the upper surface of the height adjusting plate 370 is the same as the distance of the plane 377b from the upper surface of the height adjusting plate 370.

Subsequently, referring to FIGS. 30A to 30C, an example of operation to move the area-changing parts upward and downward by moving the height adjusting plate 370 in the direction indicated by the arrow A will be described.

As shown in FIG. 30A, when the planes 367a, 377b and 367c and the inclined planes 367d and 367e of the supporting leg 367 are brought into abutment respectively with the planes 377c, 377b and 377a of the elevating member 377, the planes 365a and 365b of the supporting leg 365 and the planes 375b and 375a of the elevating member 375 come into abutment with each other respectively in a state in which the inclined plane 365c and the inclined plane 375c are apart from each other. Consequently, the area-changing part 355 and the area-changing part 357 are arranged along the horizontal direction and, simultaneously, the area-changing part 354 and the area-changing part 356 are arranged in the vertical direction, so that the platform 352 exhibits a staircase pattern which increase in height in sequence from the side of the corner 352a of the platform 352.

When the height adjusting plate 370 is moved by the motor 380 in the direction indicated by the arrow A from the state shown in FIG. 30A, the supporting leg 367 moves upward along the shape of the upper surface of the elevating member 377 (FIG. 30B). Accordingly, the planes 367a and 367b and the inclined plane 367d of the supporting leg 367 come into abutment respectively with the planes 377b and 377a and the inclined plane 377d of the elevating member 377. On the other hand, the elevating member 375 moves relatively with the supporting leg 365 until the inclined plane 365c and the inclined plane 375c come into abutment with each other in a state in which the planes 365a and 365b are in abutment with the planes 375b and 375a. Consequently, as shown in FIG. 30B, the three area-changing parts 355, 356 and 357 from among the four area-changing parts are positioned in the same plane.

Then, when the height adjusting plate 370 is moved by the motor 380 in the direction indicated by the arrow A from the state shown in FIG. 30B, the supporting leg 367 is moved upward along the shape of the upper surface of the elevating member 377 (FIG. 30C). Accordingly, the plane 367a of the supporting leg 367 comes into abutment with the plane 377a of the elevating member 377. On the other hand, the supporting leg 365 moves upward along the shape of the upper surface of the elevating member 375, and hence the plane 365a of the supporting leg 365 and the plane 375a of the elevating member 375 come into abutment with each other. Accordingly, as shown in FIG. 30C, the non-elevating part 353 and all the area-changing parts 354, 355, 356 and 357 are arranged on the same plane.

As descried above, since the area-changing parts 354 to 357 may be controlled to move upward and downward by moving the height adjusting plate 370, the desired portion may be used as the liquid reservoir.

Furthermore, the shaking mechanism 291 of the shaking device 290 is installed above the culture bag tray 241 where the culture bag 242 is arranged as the pressing unit in the culture chamber 240 as shown in FIG. 27. The shaking device 290 includes the shaking mechanism 291, the operating motor 292, the cam mechanism 293 and the positioning sensor (not shown). As shown in FIG. 27, the shaking mechanism 291 includes the operating plate 291a as the pressing unit disposed to the apparatus frame 250 via the guide rod 250a so as to be capable of moving upward and downward, and the plurality of projections 291b projecting from the bottom surface of the operating plate 291a. When the operating plate 291a is moved upward and downward alternately on the basis of the action of the cam mechanism 293 by the operating motor 292, the projections 291b of the operating plate 291a presses the culture bag 242 positioned below the shaking mechanism 291 repeatedly, that is, repeats pressing and releasing with respect to the culture bag 242. Accordingly, the culture medium in the culture bag 242 is stirred, and the cells in the culture bag 242 floats and moves in the culture medium, so that the distribution of the cells and oxygen concentration distribution in the culture bag 242 are homogenized, and hence the proliferation of the cells is promoted.

As shown in FIG. 27, the position of the operating plate 291a is detected by the positioning sensor, and is transmitted to the operation control PLC 223, and the operating motor 292 is controlled by the operation control PLC 223 on the basis of the measured value by the weight meter 251. The cell culture (shaking culture) in the culture bag 242 using the shaking device 80 described above may be carried out before the culture medium and the cells are filled in the culture bag 242 to a maximum level, or may be carried out after having filled therein to the maximum level. The shaking device 290 is controlled by the operation control PLC 223 on the basis of the detected position of the operating panel and the measured value of the weight meter 251.

In the culture chamber 240, as shown in FIG. 27, an illuminating lamp 301 is installed at a position above the culture bag 242 where the antibody is immobilized and a CCD camera 302 as an image acquiring unit is installed below the same. The CCD camera 302 is added with optical equipment such as a lens, a prism, a barrel according to the observing mode or the like. The illuminating lamp 301 is adapted to illuminate the culture bag 242 from above. The CCD camera 302 is adapted to take images of the cells in the culture bag 242 from below and acquires the images thereof. The illuminating action of the illuminating lamp 301 and the shooting action of the CCD camera 302 are controlled by the operation control PLC 223, and the images of the cells in the culture bag 242 are acquired at predetermined time intervals (six hours, for example). The cell images taken at the predetermined time intervals are stored in an image memory circuit (not shown) of the image processing unit 221.

The image processing unit 221 carries out image processing, for example, binarization or multithresholding, for the cell images taken at the predetermined time intervals stored in the image memory circuit of the image processing unit 221, so that an average value of the projected areas of the single cells and the increasing rate of the non-single cell, which is a cell aggregate formed of a plurality of single cells are calculated as evaluation parameters of the cell culture. The average value of the projected areas of the single cells (the average projected area of the single cell) is calculated from the cell image taken when 24 hours, for example, has elapsed from the moment when the culture is started after having mounted the culture bag 242 on culture bag tray 241 and stored culture bag tray 241 in culture chamber 240.

Whether the above-described cells are the non-single cell or not is determined with reference to the projected area of 100 $\mu m^2$ in such a manner that the cells having a projected area at least equal to 100 $\mu m^2$ are determined as the non-single cells and the cells having projected are less than 100 $\mu m^2$ are determined as the single cells. It is because all the cells had projected areas less than 100 $\mu m^2$ when the projected areas of the single cells in the initial stage of culture were measured. The change of the ratio of the non-single cells with respect to all the cells is computed from follow-up images of the cells (for example, images of the cells after having elapsed 24 hours, 48 hours and 72 hours from the start of culture) to calculate the increasing rate of the non-single cells. The increasing rate of the non-single cells and the average projected area of the single cells are outputted from the image processing unit 221 to the operation control PLC 223.

The operation control PLC 223 calculates a lag time from the average projected area of a single cell and estimates the timing when the corresponding cell has started proliferation. In this specification, the lag time means a time length of an induction phase required from inoculation of cells in the portion of the immobilized antibody in the culture bag tray 241 until the proliferation is started. The operation control PLC 223 determines whether the culture state of the cells, that is, whether the cell has a capability to proliferate by the stimulation from the antibody or not, from the timing when the cells has started to proliferate, and evaluates the cells. The operation control PLC 223 stops the culture in the cell culture apparatus 200 for the cells which having a very low proliferation capability on the basis of the evaluation.

The operation control PLC 223 calculates a minimum doubling time of the cells from the increasing rate of the non-single cell. The minimum doubling time in this specification means a minimum time period required for the number of cells at a certain time instant to be increased to two times the number of cells. The operation control PLC 223 determines the culture state of the cells, that is, the proliferation ability of the cells from the minimum doubling time and decide the timing or the velocity of the feeding of the culture medium to the culture bag 242.

The operation control PLC 223 and the image processing unit 221 functioning as control units include, although not shown, a CPU for executing computation or control, a storage device (memory) for storing a processing program or data, and a input/output circuit for the connection with the input devices such as a keyboard, a mouse or a touch panel for supplying data or commands and the output devices such as the monitor. The image processing unit 221 further includes the image memory circuit for storing image data from the CCD camera 302.

The storage device of the image processing unit 221 stores a program for processing (for example, binarization of multithresholding) the images of the cells in the culture bag 242 shot at predetermined time intervals by the CCD camera 302 and calculating the evaluation parameters for the cell culture (the average projected area of the single cell, the increasing rate of the non-single cell).

The storage device of the operation control PLC 223 also stores a program for determining the culture state of the cells (the proliferation capability of the cells, the proliferation ability of the cells) from the evaluation parameters of the cell culture and a program for controlling the equipment relating to the cell culture apparatus 200 and the culture unit 212 (for example, the supply pump 261 and the exhaust pump 271) according to the culture state of the cell and executing the culture operation. The storage device of the operation control PLC 223 further stores an equipment controlling program for controlling the equipment relating to the culture device 210 and the culture unit 212 on the basis of the signals from various sensors of the cell culture apparatus 200 and the culture unit 212. The storage device of the image processing unit 221 also stores an equipment controlling program for controlling the CCD camera 302 at predetermined time intervals and acquiring the cell images.

Referring now to flowcharts shown in the process drawings in FIG. 31 to FIG. 40, a process of culturing cells carried out by the operation control PLC 223 and the image processing unit 221 by executing the above-described programs will be described.

Figure 31:
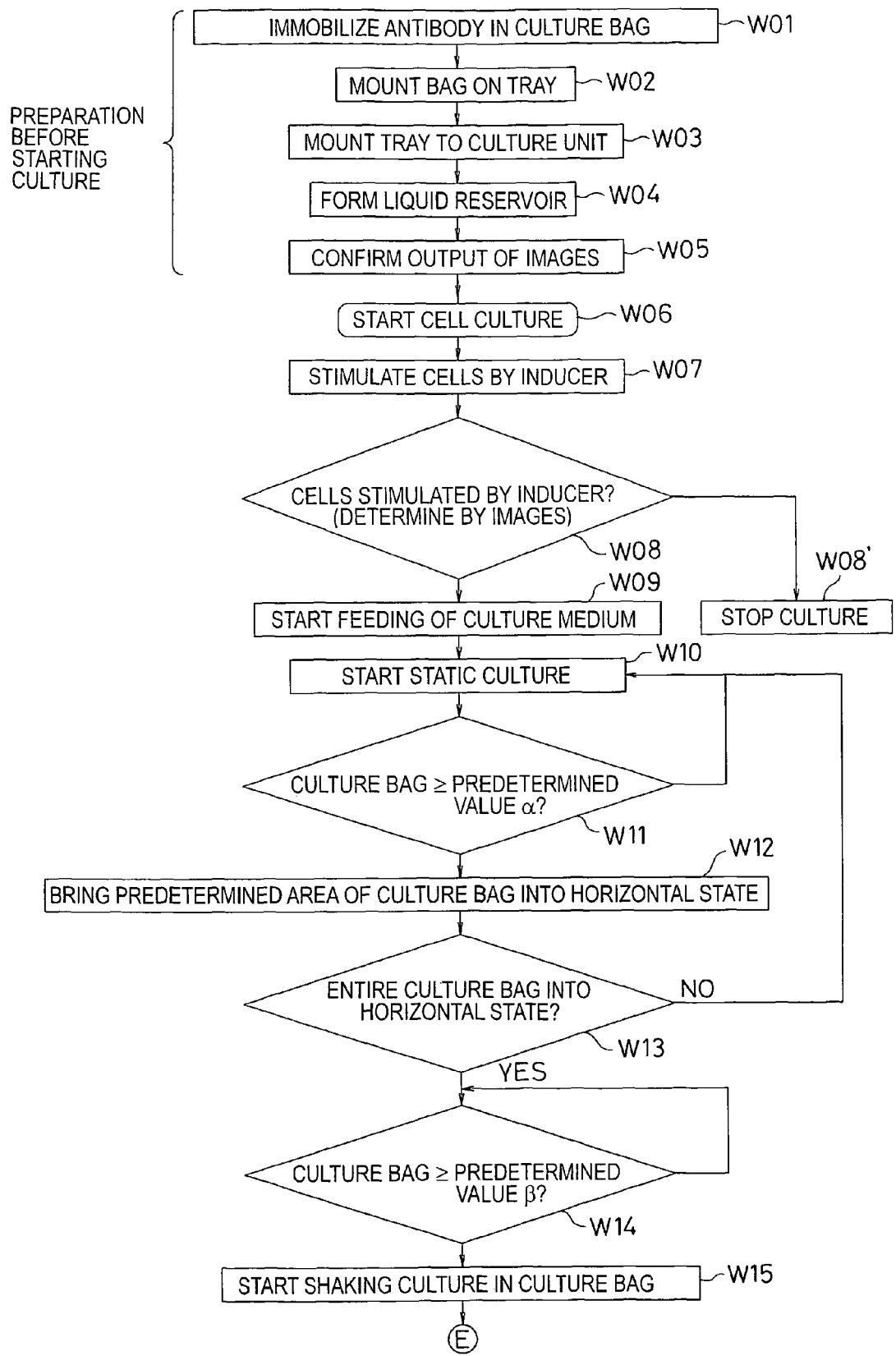
FIG. 31 is a flowchart showing process steps in an antibody stimulating intermittent perfusion culture process in the culture unit in FIG. 27 in a case in which a step of collecting the cells in the culture bag is included.
Figure 32:
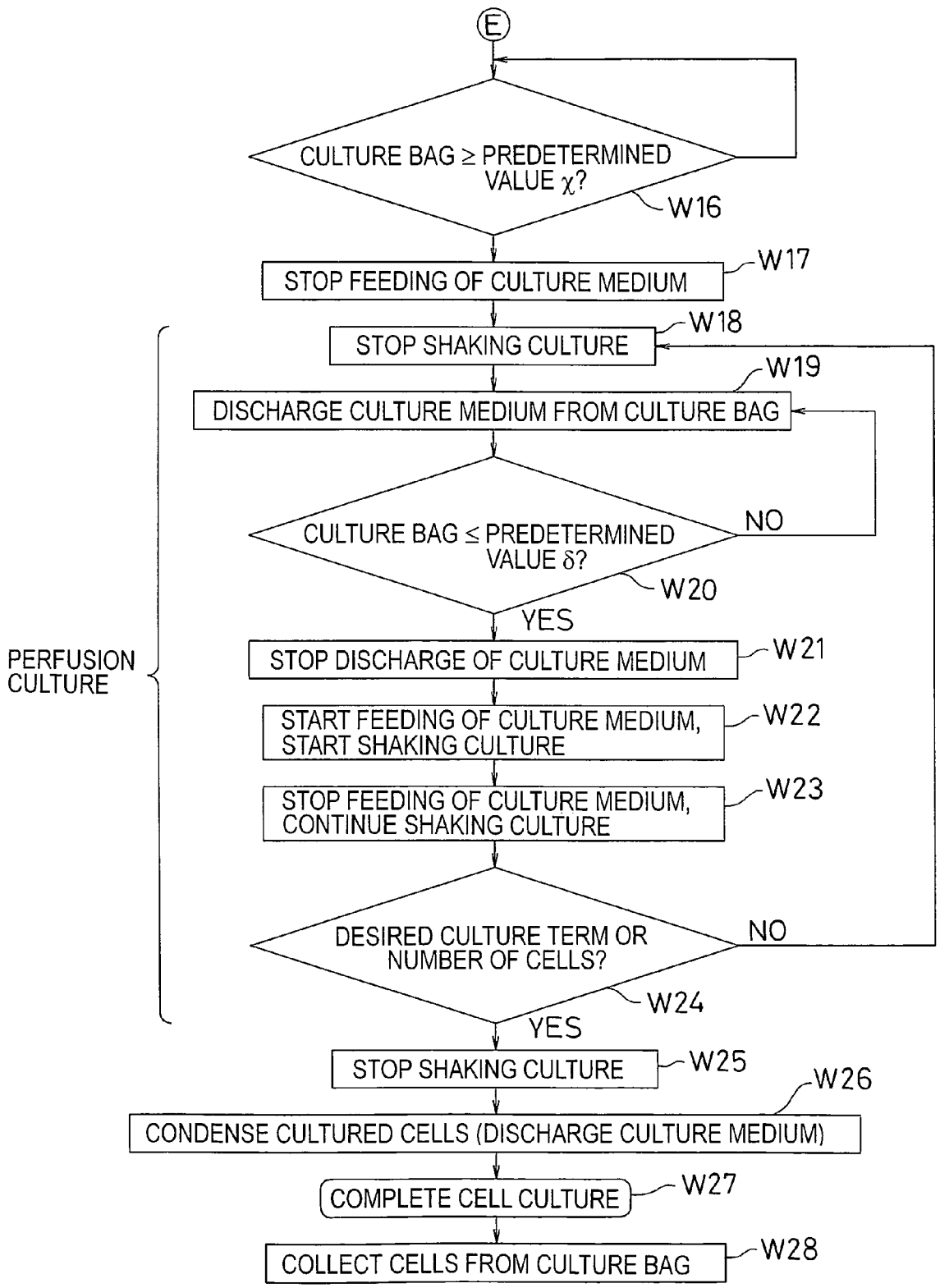
FIG. 32 is a flowchart showing steps following the process steps in FIG. 31.

FIG. 31 and FIG. 32 show an antibody stimulating intermittent perfusion culture process in a case of collecting the cells in the culture bag 242.

As shown in FIG. 31, the operator immobilizes an antibody in the culture bag 242 in the clean bench or the like (W01 in FIG. 31), adds the culture medium, and mounts the culture bag 242 having inoculated the cells on the culture medium bag tray 231. Then, the operator mounts the culture medium bag 233 in which the culture medium is added in the clean bench or the like onto the culture medium bag tray 231, mounts the waste water bag 234 on the waste water bag tray 232, and couples the culture bag 242 with the culture medium bag 233 and the waste water bag 234 using the coupling of a supply system 264 and the exhaust system coupling 274, respectively (W02 in FIG. 31).

Then, the operator carries the culture bag tray 241, the culture medium bag tray 231 and the waste water bag tray 232 in the single culture unit 212 of the cell culture apparatus 200, illuminated by an illumination lamp, for example, in green, causes the culture bag tray 241 to be supported by the frame 250 of the culture chamber 240 and installs the culture medium bag tray 231 and the waste water bag tray 232 in the low temperature chamber 230. Then, the operator connects the pump tubes 262 and 272 of the culture bag 242 to the supply pump 261 and the exhaust pump 271, respectively, (W03 in FIG. 31).

Then, the operator confirms images in the culture bag 242 stored in the culture unit 212, which are outputted from the CCD camera 302 (W05 in FIG. 31). Before confirming the outputted images, the operator activates the inclined motor 280 of the culture unit 212 to move the area-changing parts 252b and 252c of the platform 252 downward to form the liquid reservoirs in the culture bag 242 (W04 in FIG. 31). The operator then measures the weight of the installed culture bag 242 by the weight meter 251 of the culture unit 212.

Then, the operator closes the door of the culture unit and starts the cell culture in the culture unit 212 (W06 in FIG. 31). Accordingly, the cells are stimulated by the antibody for the proliferation in the liquid reservoirs in the culture bag 242 (W07 in FIG. 31). The CCD camera 302 of the culture unit 212 takes the images of the cells in the liquid reservoirs in the culture bag 242 at predetermined time intervals (every six hours, for example), the image processing unit 221 calculates the evaluation parameters of the cell culture from the picked-up image. The operation control PLC 223 calculates the lag time from the evaluation parameter, determines whether the cells has a capability to proliferate upon reception of stimulation from the antibody or not, calculates the minimum doubling time, and determines the proliferation ability of the cells (W08 in FIG. 31).

When the capability of proliferation cannot be seen even when a predetermined time period (24 hours, for example) has elapsed since the cells has stimulated by the antibody in the culture bag 242, the operation control PLC 223 cancels the culture of the cell in the cell culture apparatus 200 (W08' in FIG. 31). When it is determined that the cells in the culture bag 242 has a capability of proliferation, the operation control PLC 223 decides the velocity and timing of feeding of the culture medium into the culture bag 242 on the basis of the proliferation ability of the cells. The operation control PLC 223 activates the supply pump 261 on the basis of this decision, and feeds the culture medium in the culture medium bag 233 on the culture medium bag tray 231 to the culture bag 242 (W09 in FIG. 31).

With the activation of the supply pump 261, the static culture of the cells is started in the liquid reservoir having a predetermined area in the culture bag 242 (W10 in FIG. 31). The operation control PLC 223 determines whether the weight of the culture medium and the cells in the culture bag 242 measured by the weight meter 251 is increased to a value at least equal to the predetermined value $\alpha$ or not (W11 in FIG. 31). At a timing when the value at least equal to the predetermined value $\alpha$ is reached, the operation control PLC 223 activates the inclined motor 280, moves the area-changing parts 252b and 252c of the platform 252 upward via the cam mechanism 281 and brings a predetermined area of the culture bag 242 into a horizontal state to change the liquid reservoir (W12 in FIG. 31). This process is repeated until all the steps formed on the platform 252 are eliminated and the culture bag 242 is brought into a horizontal state (W13 in FIG. 31).

Then, the operation control PLC 223 determines whether the weight of the culture medium and the cells in the culture bag 242 measured by the weight meter 251 is increased to a value at least equal to the predetermined value β or not (W14 in FIG. 31). At the timing when the value at least equal to the predetermined value β is reached, the operation control PLC 223 activates the operating motor 292. Accordingly, the shaking device 290 is activated, and the shaking culture in which the shaking mechanism 291 of the shaking device 290 presses the culture bag 242 repeatedly is started (W15 in FIG. 31). The operation control PLC 223 continues to determine whether the weight of the culture medium and the cells in the culture bag 242 measured by the weight meter 251 is increased to a value at least equal to the predetermined value χ or not (W16 in FIG. 32). At a timing when the value at least equal to the predetermined value χ is reached, the operation control PLC 223 stops the supply pump 261 to stop the feeding of the culture medium from the culture medium bag 233 on the culture medium bag tray 231 to the culture bag 242 (W17 in FIG. 32), stops the operating motor 292 to stop the shaking culture in the culture bag 242 (W18 in FIG. 32).

The operation control PLC 223 activates the exhaust pump 271 after having settled the cells in the culture bag 242 to discharge the used culture medium (supernatant in the culture bag 242) in the culture bag 242 to the used waste water bag 234 on the waste water bag tray 232 (W19 in FIG. 32). Then, the operation control PLC 223 determines whether the weight of the culture medium and the cells in the culture bag 242 measured by the weight meter 251 is reduced to a value at most equal to a predetermined value δ or not (W20 in FIG. 32). At a timing when the value at most equal to the predetermined value δ is reached, the operation control PLC 223 stops the exhaust pump 271 to stop the discharge of the used culture medium from the culture bag 242 (W21 in FIG. 32). Then, the operation control PLC 223 activates the supply pump 261 to feed the culture medium from the culture medium bag 233 on the culture medium bag tray 231 to the culture bag 242, and activates the operating motor 292 to carry out the shaking culture in the culture bag 242 by the shaking device 290 (W22 in FIG. 32). The operation control PLC 223 stops the supply pump 261 after having elapsed a predetermined time to stop the feeding of the culture medium from the culture medium bag 233 on the culture medium bag tray 231 to the culture bag 242 and continue the shaking culture in a state in which the operating motor 292 is activated (W23 in FIG. 32).

The operation control PLC 223 determined whether the desired culture term depending on the date and time of usage of the cells to proliferate is reached or not, or the image processing unit 221 determines whether the desired number of cells is reached in the culture bag 242 or not (W24 in FIG. 32). When the desired culture term or the desired number of cells is not reached, the process steps in Steps W18 to W23 are repeated. When counting the number of cells, the shaking device 290 is stopped once to wait until the cells are settled. Then, the images of the interior of the culture bag 242 are taken by the CCD camera 302. The image processing unit 221 estimates and calculates the number of cells existing in the bag from the acquired images.

Steps W18 to W23 are steps of intermittent perfusion culture in which discharge of the used culture medium in the culture bag 242 and supply (feed) of new culture medium into the culture bag 242 are carried out alternately.

At the time point where the desired culture term or the number of cells are reached in Step W24, the operation control PLC 223 stops the operating motor 292 as shown in FIG. 32 to stop the shaking culture in the culture bag 242 (W25 in FIG. 32). Then, the operation control PLC 223 activates the exhaust pump 271 after having settled the cells in the culture bag 242 to discharge the used culture medium in the culture bag 242 to the waste water bag 234 on the waste water bag tray 232, and condense the cells until the culture medium and the cells in the culture bag 242 are reduced to about ½ to ⅓ on the basis of the measured value by the weight meter 251 (W26 in FIG. 32)

The operation control PLC 223 then stops the exhaust pump 271 to complete the cell culture (W27 in FIG. 32). After having completed the culture, the operator transfers the cells in the culture bag 242 to a vessel for the centrifugation in the clean bench or the like, and then, the cells are collected by the centrifugation (W28 in FIG. 32).

Figure 33:
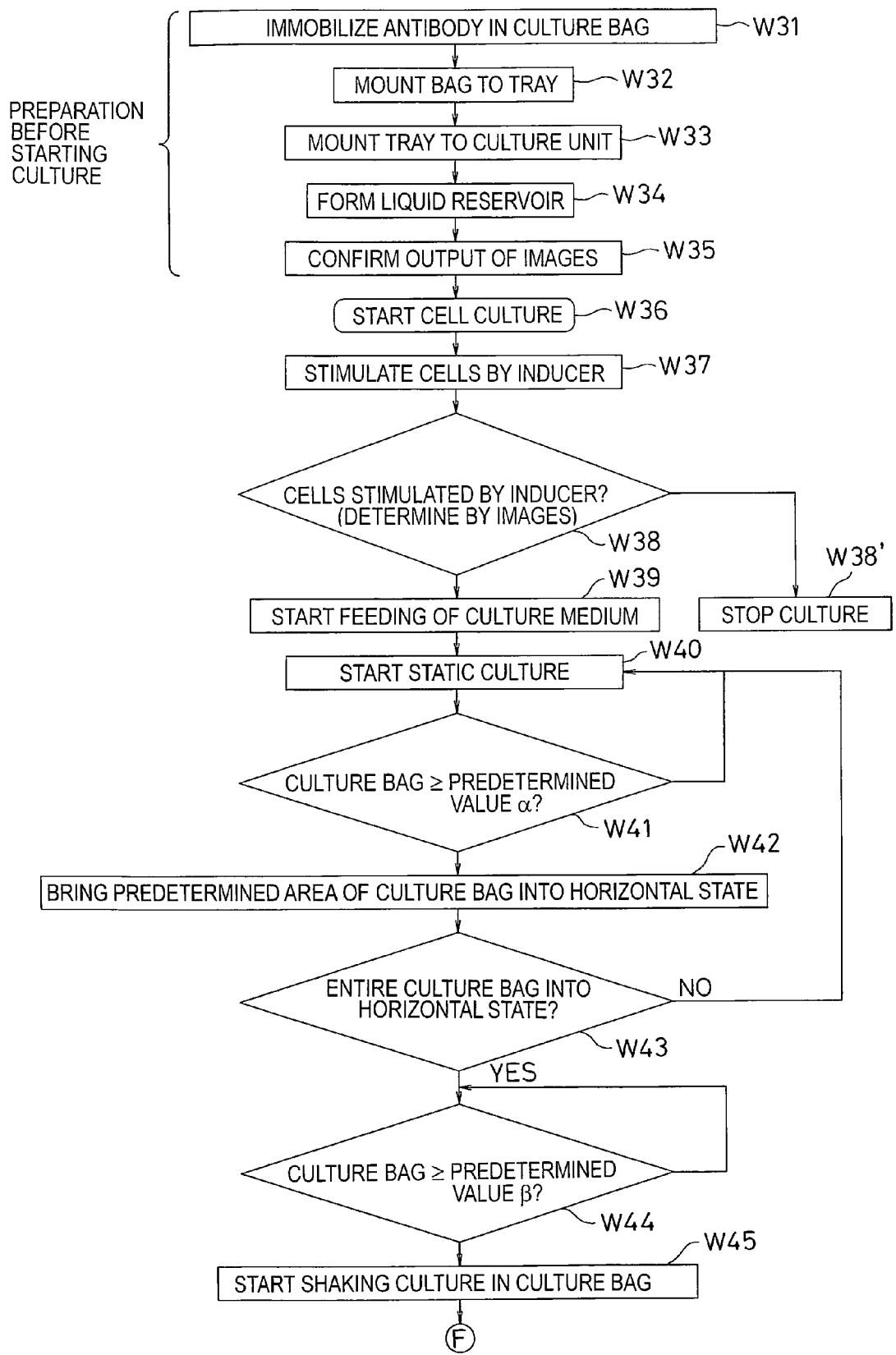
FIG. 33 is a flowchart showing process steps of the antibody stimulating intermittent perfusion culture process in the culture unit in FIG. 27 in a case in which a step of collecting the cells in the cell collecting bag is included.
Figure 34:
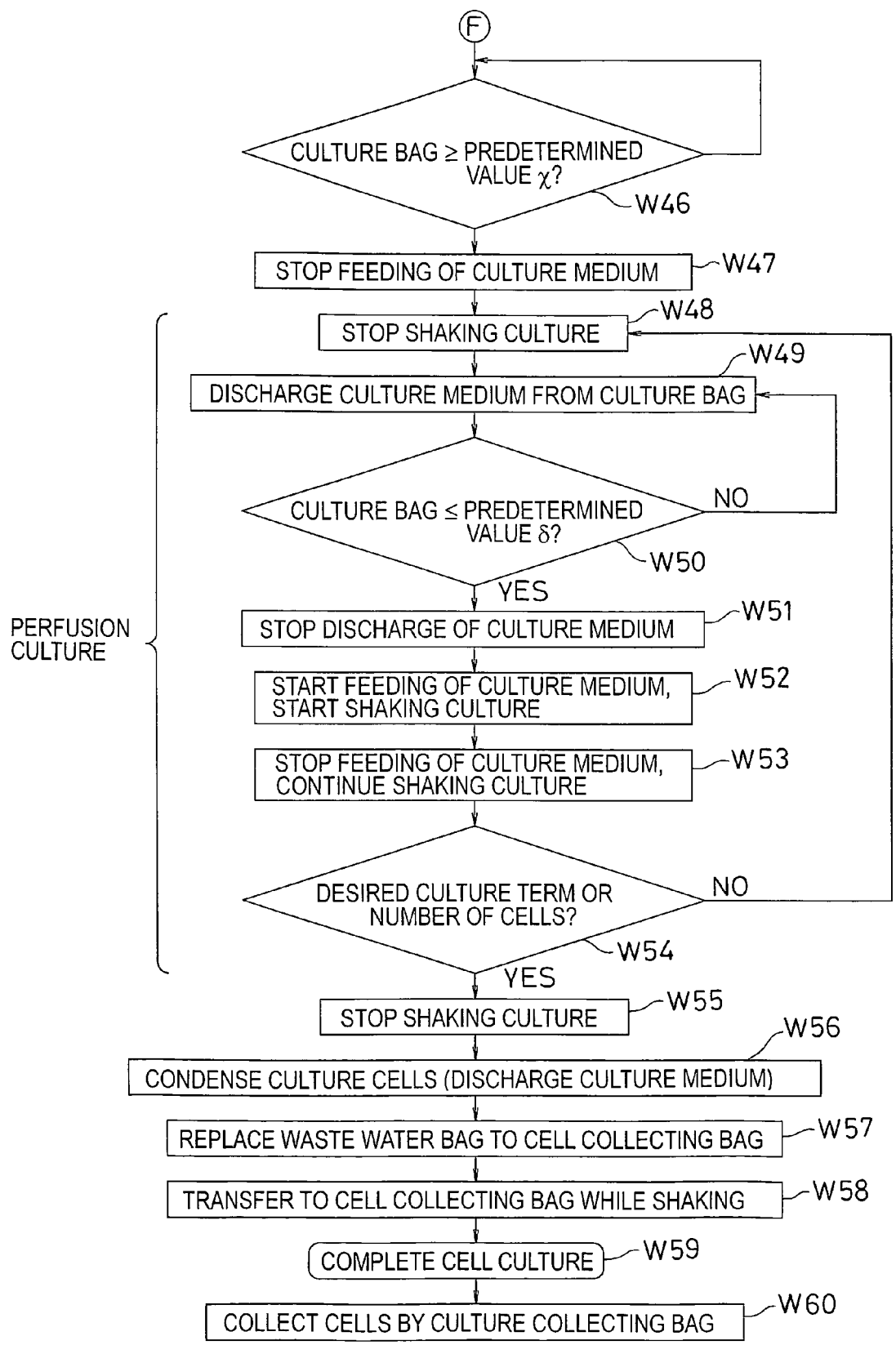
FIG. 34 is a flowchart showing steps following the process steps in FIG. 33.

In the similar antibody stimulating intermittent perfusion culture process, the case in which the process of collecting the cells by the cell collecting bag is included is shown in FIG. 33 and FIG. 34. Therefore, since Steps W31 to W56 of the process shown in FIG. 33 and FIG. 34 are the same as Steps W01 to W26 shown in FIG. 31 and FIG. 32, description is omitted.

In Step W56 shown in FIG. 34, after having condensed the cells in the culture bag 242 by the activation of the exhaust pump 271, the operation control PLC 223 stops the exhaust pump 271 and prompts the operator to replace the waste water bag 234 on the waste water bag tray 232 by the cell collecting bag (W57 in FIG. 34). The cell collecting bag is a bag to be mounted to the centrifuge and used for the centrifugation.

After having replaced the waste water bag 234 on the waste water bag tray 232 by the cell collecting bag, the operation control PLC 223 activates the exhaust pump 271 and the operating motor 292. Then, the operation control PLC 223 shakes the interior of the culture bag 242 by the shaking device 290 to transfer the cells in the culture bag 242 to the cell collecting bag mounted on the waste water bag tray 232 together with the culture medium (W58 in FIG. 34). Then, the operation control PLC 223 stops the exhaust pump 271 and the operating motor 292 to stop the collection of the cells from the culture bag 242 to complete the cell culture (W59 in FIG. 34). After having completed the cell collection, the operator mounts the cell collecting bag to the centrifuge, so that the cells are collected by the centrifugation (W60 in FIG. 34).

Figure 35:
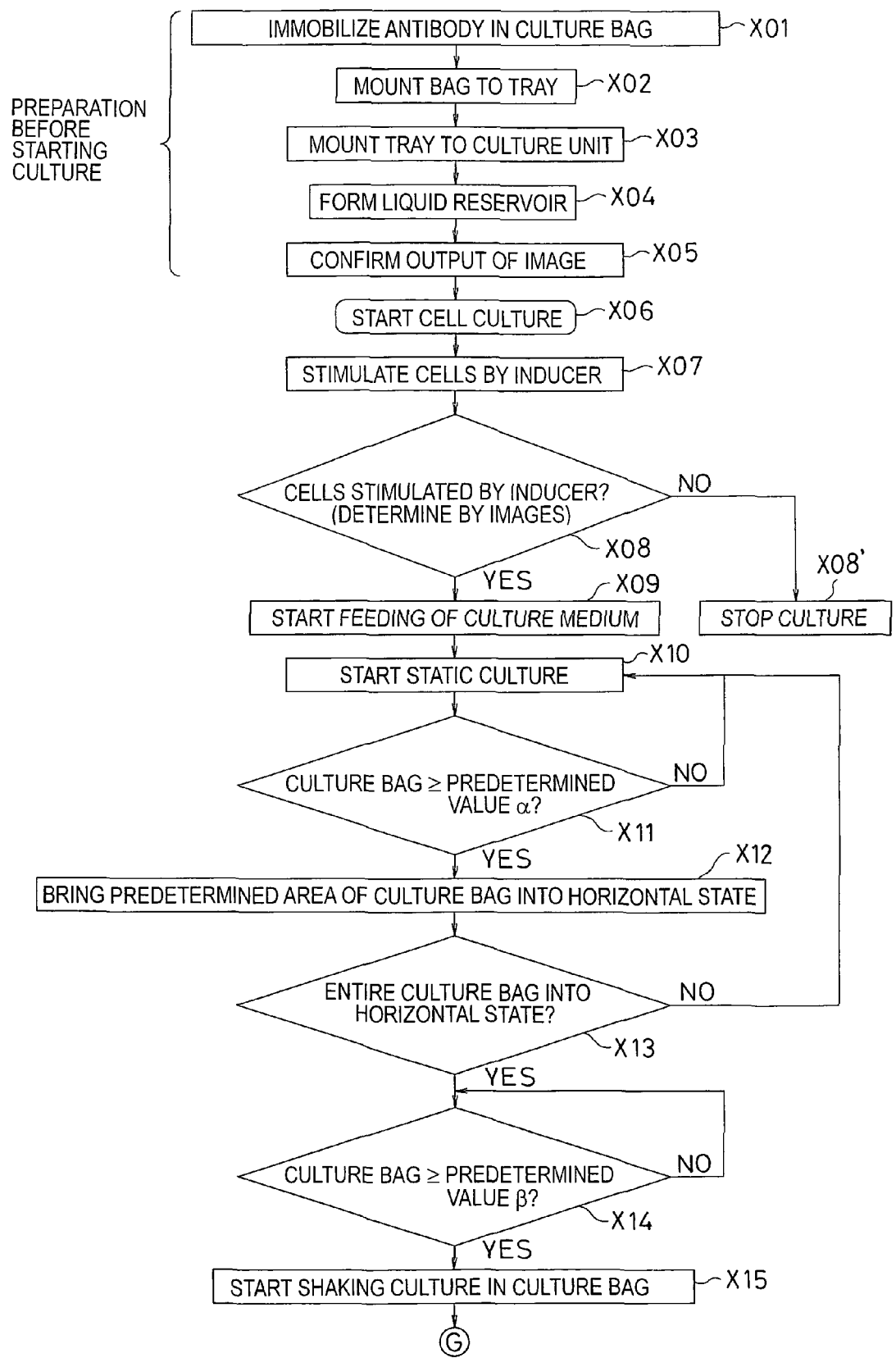
FIG. 35 is a flowchart showing process steps of an antibody stimulating consecutive perfusion culture process in the culture unit in FIG. 27.
Figure 36:
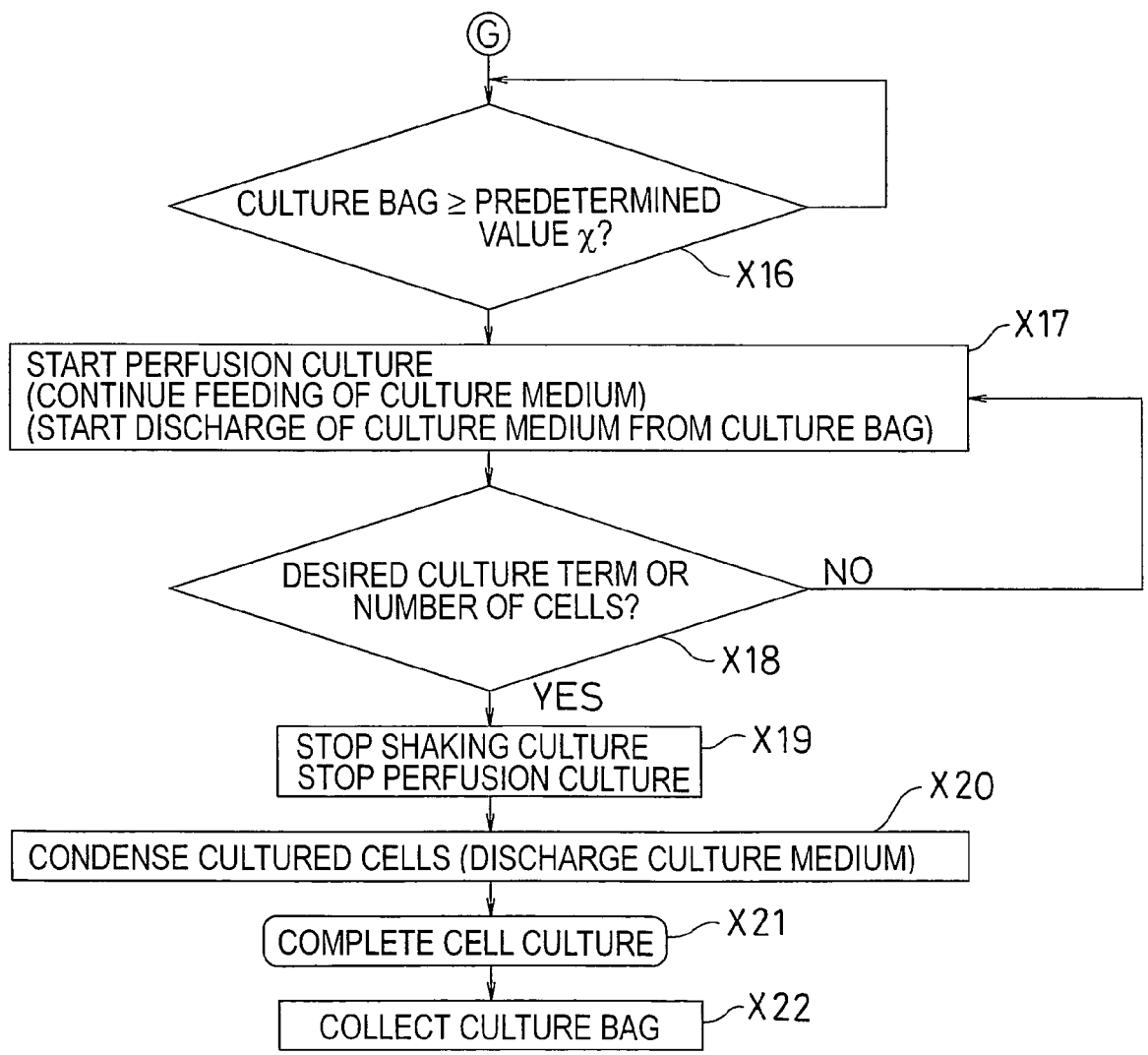
FIG. 36 is a flowchart showing steps following the process steps in FIG. 35.

Referring now to FIG. 35 and FIG. 36, process steps in an antibody stimulating consecutive perfusion culture process will be described. Since Steps X01 to X15 in the antibody stimulating consecutive perfusion culture process shown in FIG. 35 and FIG. 36 are the same as Steps W01 to W15 in the antibody stimulating intermittent perfusion culture process shown in FIG. 31 and FIG. 32, description is omitted.

In the antibody stimulating consecutive perfusion culture process, a filter (not shown) is disposed between the culture bag 242 and the exhaust pump 271.

The operation control PLC 223 activates the exhaust pump 271 at a timing when the weight of the culture medium and the cells in the culture bag 242 is increased to a value at least equal to the predetermined value χ (X16 in FIG. 36) to discharge the used culture medium in the culture bag 242 to the waste water bag 234 on the waste water bag tray 232 while the culture medium is fed from the culture medium bag 233 on the culture medium bag tray 231 into the culture bag 242 and the shaking culture by the shaking device 290 is carried out in the culture bag 242. Accordingly, the consecutive perfusion culture in which the feeding of the culture medium to the culture bag 242 and the discharge of the culture medium from the culture bag 242 are carried out simultaneously is started in the culture bag 242 (X17 in FIG. 36). At this time, the cells in the culture bag 242 are prevented from flowing by the filter and hence do not flow into the waste water bag 234. During the consecutive perfusion culture, the shaking culture by the shaking device 290 is simultaneously carried out.

The operation control PLC 223 determines whether a desired culture term depending on the date and time of usage of the cells to proliferate is reached or not, or the image processing unit 221 determines whether the desired number of cells is reached in the culture bag 242 or not (X18 in FIG. 36). When the desired culture term or the desired number of cells is not reached, the consecutive perfusion culture in Step X17 is repeated. When counting the number of cells, the shaking device 290 is stopped once to wait until the cells are settled. Then, the images of the interior of the culture bag 242 are taken by the CCD camera 302. The image processing unit 221 estimates and calculates the number of cells existing in the bag from the acquired images.

At the time point where the desired culture term or the number of cells are reached in the Step X18, the operation control PLC 223 stops the supply pump 261, the exhaust pump 271 and the operating motor 292 to stop the perfusion culture and the shaking culture (X19 in FIG. 36). Then, the operation control PLC 223 activates the exhaust pump 271 after having settled the cells in the culture bag 242 to discharge the used culture medium in the culture bag 242 to the waste water bag 234 on the waste water bag tray 232 and condense the cells until the culture medium and the cells in the culture bag 242 are reduced to about ½ to ⅓ on the basis of the measured value by the weight meter 251 (X20 in FIG. 36). To stop the shaking device in the condensing process is to prevent a large amount of cells from flowing into the tube and from clogging the filter.

The operation control PLC 223 then stops the exhaust pump 271 to complete the cell culture (X21 in FIG. 36). After having completed the culture, the operator transfers the cells in the culture bag 242 to a vessel for the centrifuge in the clean bench or the like, and then, the cells are collected by the centrifugation (X22 in FIG. 36).

Figure 37:
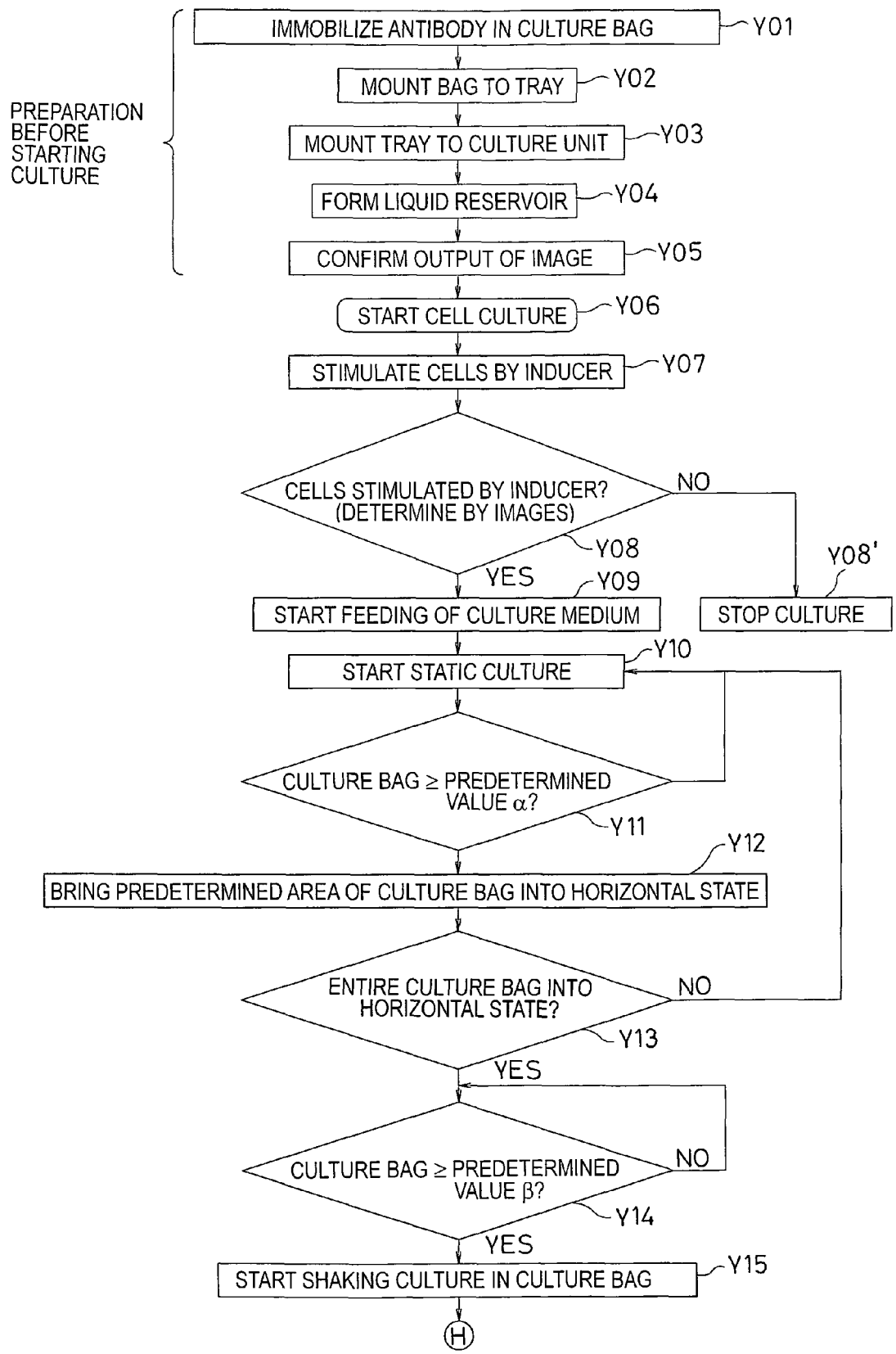
FIG. 37 is a flowchart showing process steps in an antibody stimulating simple feeding culture process in the culture unit in FIG. 27.
Figure 38:
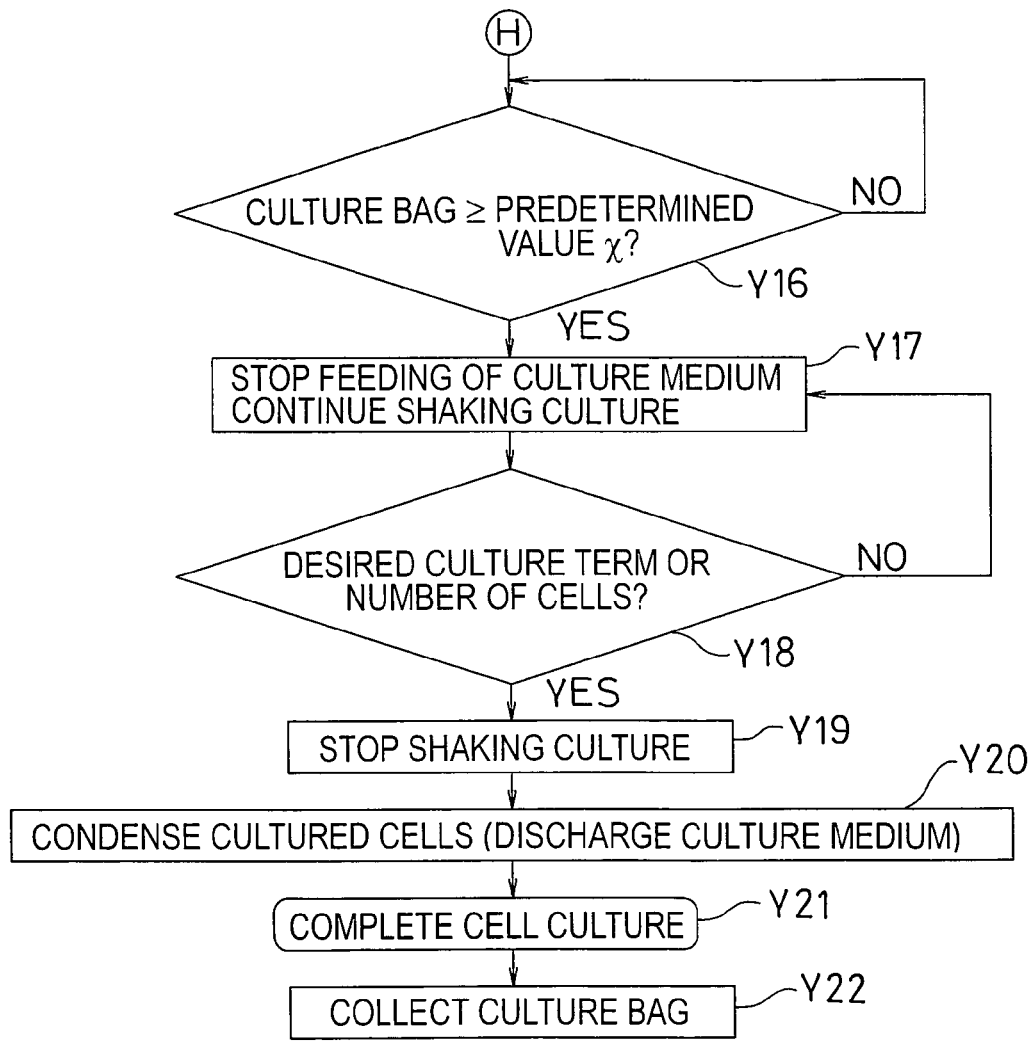
FIG. 38 is a flowchart showing steps following the process steps in FIG. 37.

Referring now to FIG. 37 and FIG. 38, processing steps in an antibody stimulating simple feeding culture process will be described. Since Steps Y01 to Y15 in the antibody stimulating simple feeding culture process in FIG. 37 and FIG. 38 are the same as Steps in W01 to W15 in the antibody stimulating intermittent perfusion culture process in FIG. 31 and FIG. 32, description is omitted.

The operation control PLC 223 determines whether the weight of the culture medium and the cells in the culture bag 242 measured by the weight meter 251 is increased to a value at least equal to the predetermined value χ or not (Y16 in FIG. 38). At a timing when a value at least equal to or larger than the predetermined value χ is reached, the operation control PLC 223 stops the supply pump 261 to stop the feeding of the culture medium from the culture medium bag 233 on the culture medium bag tray 231 to the culture bag 242 and to continue the shaking culture while activating the operating motor 292 (Y17 in FIG. 38).

The operation control PLC 223 determines whether a desired culture term depending on the date and time of usage of the cells to proliferate is reached or not, or the image processing unit 221 determines whether the desired number of cells is reached in the culture bag 242 or not (Y18 in FIG. 38). When the desired culture term or the desired number of cells is not reached, the shaking culture is continued (No in Y18).

When counting the number of cells, the shaking device 290 is stopped once to wait until the cells are settled. Then, the images of the interior of the culture bag 242 are taken by the CCD camera 302. The image processing unit 221 estimates and calculates the number of cells existing in the bag from the acquired images.

At a timing when the desired culture term or the number of cells is reached in Step Y18, the operation control PLC 223 stops the operating motor 292 as shown in FIG. 38 to stop the shaking culture in the culture bag 242 (Y19 in FIG. 38). After having settled the cells in the culture bag 242, the exhaust pump 271 is activated to discharge the used culture medium in the culture bag 242 to the waste water bag 234 on the waste water bag tray 232 and condense the cells until the culture medium and the cells in the culture bag 242 are reduced to about ½ to ⅓ on the basis by the measured value of the weight meter 251 (Y20 in FIG. 38).

The operation control PLC 223 then stops the exhaust pump 271 to complete the cell culture (Y21 in FIG. 38). After having completed the culture, the operator transfers the cells in the culture bag 242 to the vessel for the centrifuge in the clean bench or the like, and then the cells are collected by the centrifugation (Y22 in FIG. 38).

Figure 39:
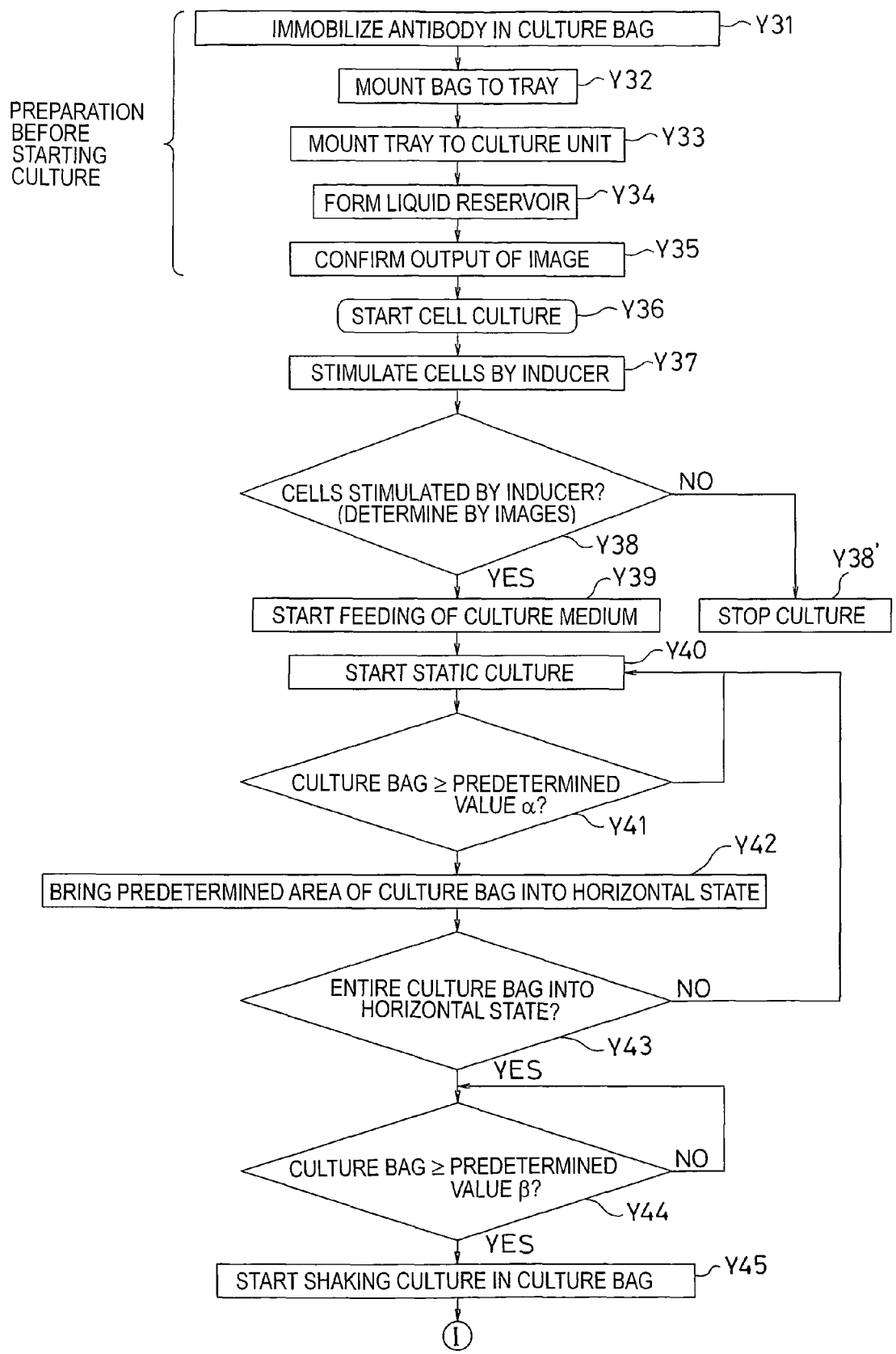
FIG. 39 is a flowchart showing process steps in the antibody stimulating simple feeding culture process in the culture unit in FIG. 27 in a case in which a step of collecting the cells using the cell collecting bag is included.
Figure 40:
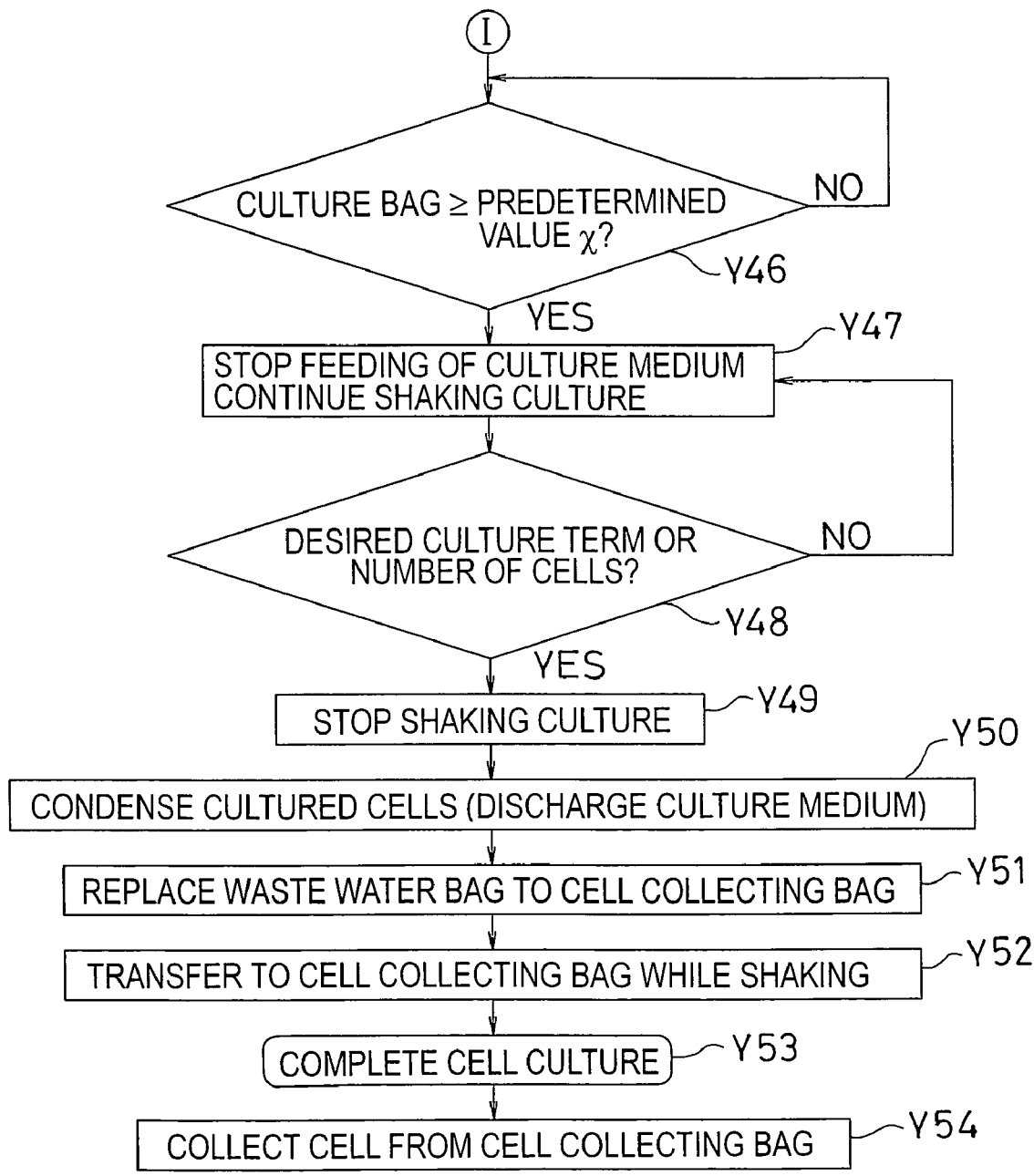
FIG. 40 is a flowchart showing steps following the process steps in FIG. 39.

Subsequently, in the similar antibody stimulating simple feeding culture process, the case in which the step of collecting the cells by the cell collecting bag is included is shown in FIG. 39 and FIG. 40. Therefore, since Steps Y31 to Y50 in the process shown in FIG. 39 and FIG. 40 are the same as Steps Y01 to Y20 in FIG. 37 and FIG. 38, description is omitted.

In Step Y50 shown in FIG. 40, after having condensed the cells in the culture bag 242 by the activation of the exhaust pump 271, the operation control PLC 223 stops the exhaust pump 271 and prompts the operator to replace the waste water bag 234 on the waste water bag tray 232 by the cell collecting bag (Y51 in FIG. 40). The cell collecting bag is a bag to be mounted to the centrifuge and used for the centrifugation.

After having replaced the waste water bag 234 on the waste water bag tray 232 by the cell collecting bag, the operation control PLC 223 activates the exhaust pump 271 and the operating motor 292. Then, the shaking device 290 shakes the interior of the culture bag 242 to transfer the cells in the culture bag 242 to the cell collecting bag mounted on the waste water bag tray 232 together with the culture medium (Y52 in FIG. 40). The operation control PLC 223 then stops the exhaust pump 271 and the operating motor 292 to stop the collection of the cells from the culture bag 242 and complete the cell culture (Y53 in FIG. 40). After having completed the cell collection, the operator mounts the cell collecting bag to the centrifuge, so that the cells are collected by the centrifugation (Y54 in FIG. 40).

In this configuration, according to the embodiments shown above, the following effects (1) to (7) are achieved.

(1) The image processing unit 221 processes the images of the cells in the culture bag 242 taken by the CCD camera 302 to acquire the evaluation parameters of the cell culture (the average projected area of the single-cell, the increasing rate of the non-single cell), the operation control PLC 223 determines and evaluates the culture state of the cells (the proliferation capability and the proliferation ability) to carry out the culture operation according to the culture state (the culture medium feeding at the predetermined feeding velocity or the timing from the culture medium bag 233 to the culture bag 242). Consequently, since the culture state of the cells is determined in a non-contact state, the cells are prevented from getting damaged, and the operator needs not carry out the culture operation one by one, the labor of the operator is alleviated. Since the cells of one patient may be inoculated to the single culture bag 242 stored in the culture unit 212, and the culture operation according to the culture state of the cells may be carried out on the individual basis, so that the adequate culture operation is achieved. Since the culture operation suitable for the culture state of the cells is achieved, the culture operation by the hour is enabled, and the culture is accelerated to shorten the culture term.

(2) The culture medium bag 233, the waste water bag 234 and the culture bag 242 are coupled in the clean bench or the like and are configured into a closed loop to install in the culture unit 212. Therefore, aseptic conditions in a completely closed system are maintained.

(3) The culture process is carried out automatically since the culture bag tray 241, the culture medium bag tray 231 and the waste water bag tray 232 are installed in the culture unit 212 at the time of starting the culture until the culture is completed. Therefore, the cells in the culture bag 242 is prevented from getting damaged due to the change of environment, and the aseptic operation for supplying the culture medium to the culture bag 242 in the clean bench or the like may be omitted.

(4) The antibody stimulation and the cell proliferation in the initial state of culture in culture bag 242 may be carried out in the same culture bag 242, and the liquid reservoirs where the cells and the culture medium are stored in the culture bag 242 may be changed into the predetermined areas. Therefore, the cell density per area during the culture is maintained at a density preferable to the proliferation, so that the cells proliferate efficiently.

(5) The used culture medium in the culture bag 242 is discharged and stored in the waste water bag 234 on the waste water bag tray 232, the cell density in the culture bag 242 may be increased and hence condensed. Therefore, the number of times of operation of the centrifugation for collecting the cells is reduced. Consequently, the labor for collecting the cells is saved, and the damage of the cells in association with the centrifugation is reduced.

(6) When all the cells condensed in the culture bag 242 are to be collected into the cell collecting bag mounted to the waste water bag tray 232, the cells may be collected by mounting the cell collecting bag directly to the centrifuge. Therefore, the labor for collecting the cells is saved.

(7) The culture medium in the culture bag 242 is stirred by repeatedly pressing the flexible culture bag 242 having the culture medium to which the cells are inoculated stored therein by the projections 291*b* of the operating plate 291*a* in the shaking mechanism 291 of the shaking device 290. Therefore, the distribution of cells and the oxygen concentration distribution in the culture bag 242 are homogenized, so that the proliferation of the cells is accelerated and the efficiency of the cell culture is improved.

The cells only float in the culture medium stirred by being pressed repeatedly by the operating plate 291*a* of the shaking device 290. Therefore, the cells are prevented from getting damaged.

What is claimed is:

1. A cell culture apparatus comprising:
a culture vessel which cultures cells;
a culture medium storage unit which stores a culture medium supplied to the culture vessel;
a platform on which the culture vessel is placed, wherein the platform includes a non-elevating part which is a portion of the platform on which the culture vessel is placed, and at least one area-changing part which is another portion of the platform on which the culture vessel is placed, wherein the at least one area-changing part is movable upward and downward such that the non-elevating part of the platform and the at least one area-changing part of the platform are arrangeable on different planes, and wherein a culture area of the culture vessel is changed by moving the at least one area-changing part;
an image acquiring unit which acquires images of the cells in the culture vessel; and
a control unit which determines a culture state of the cells from the images of the cells acquired by the image acquiring unit and controls a culture operation to be carried out based on the determination,
wherein the control unit controls the platform to change the culture area of the culture vessel.

2. The cell culture apparatus according to claim 1, wherein the culture vessel includes a proliferation culture vessel for causing the cells to proliferate and a function expressing culture vessel for causing the cells to express the functions, and the image acquiring unit acquires the images of the cells in the function expressing culture vessel.

3. The cell culture apparatus according to claim 2, wherein the function expressing culture vessel is an inducer stimulating culture vessel for stimulating cells by an inducer for the proliferation, and the control unit determines the proliferation capability of the cells and the proliferation ability of the cells on the basis of the images of the cells in the inducer stimulating culture vessel and controls timing of transferring the cells from the inducer stimulating culture vessel to the proliferation culture vessel and the culture operation, wherein the culture operation includes supply of the culture medium from the culture medium storage unit to the proliferation culture vessel.

4. The cell culture apparatus according to claim 2, wherein the function expressing culture vessel is a differentiation-inducing culture vessel for causing the cells to differentiate, and the control unit controls a differentiation-inducing operation based on the images of the cells in the differentiation-inducing culture vessel.

5. The cell culture apparatus according to claim 1, wherein the culture medium storage unit comprises a cassette structure and is connected to the culture vessel.

6. The cell culture apparatus according to claim 2, wherein the function expressing culture vessel comprises a cassette structure, and is connected to the proliferation culture vessel and the culture medium storage unit.

7. The cell culture apparatus according to claim 2, wherein the culture medium storage unit, the function expressing culture vessel and the proliferation culture vessel make up a closed system.

8. The cell culture apparatus according to claim 2, wherein a liquid reservoir is selectively formed in the proliferation culture vessel, and the cell and the culture medium are stored in the liquid reservoir in an initial stage of culture in the proliferation culture vessel.

9. The cell culture apparatus according to claim 2, wherein the control unit causes cells proliferated in the proliferation culture vessel to be introduced into the function expressing culture vessel, and the image acquiring unit acquires images of the introduced cells.

10. The cell culture apparatus according to claim 2, wherein the culture medium storage unit includes a used culture medium storage vessel which is adapted to store a used culture medium installed therein together with a culture medium storage vessel which is able to store a culture medium to be supplied to the culture vessel, and the used culture medium in the proliferation culture vessel is discharged to the used culture medium storage vessel and is stored therein.

11. The cell culture apparatus according to claim 2, wherein the culture medium storage unit is adapted to mount a cell collecting vessel for collecting the cells mounted thereto, and the cells condensed in the proliferation culture vessel are collected in the cell collecting vessel.

* * * * *